US010941108B2

(12) United States Patent
Jeong et al.

(10) Patent No.: US 10,941,108 B2
(45) Date of Patent: Mar. 9, 2021

(54) ORGANIC COMPOUND AND ORGANIC ELECTROLUMINESCENT ELEMENT COMPRISING SAME

(71) Applicant: MATERIAL SCIENCE CO., LTD., Seoul (KR)

(72) Inventors: Jae Ho Jeong, Incheon (KR); Tae Wan Lee, Seoul (KR); Kwang Seok Do, Seoul (KR); Dong Hun Lee, Seoul (KR); Jin Sung Kim, Chungcheongnam-do (KR)

(73) Assignee: Material Science Co., Ltd.

( * ) Notice: Subject to any disclaimer, the term of this patent is extended or adjusted under 35 U.S.C. 154(b) by 288 days.

(21) Appl. No.: 16/067,069

(22) PCT Filed: Dec. 29, 2016

(86) PCT No.: PCT/KR2016/015485
§ 371 (c)(1),
(2) Date: Jun. 28, 2018

(87) PCT Pub. No.: WO2017/116167
PCT Pub. Date: Jul. 6, 2017

(65) Prior Publication Data
US 2019/0016666 A1  Jan. 17, 2019

(30) Foreign Application Priority Data

Dec. 31, 2015 (KR) .................. 10-2015-0191316
Sep. 29, 2016 (KR) .................. 10-2016-0125568

(51) Int. Cl.
| | |
|---|---|
| *H01L 51/50* | (2006.01) |
| *C07C 211/54* | (2006.01) |
| *H01L 51/00* | (2006.01) |
| *H01L 51/52* | (2006.01) |
| *C07D 209/88* | (2006.01) |
| *C07D 213/74* | (2006.01) |
| *C07C 255/58* | (2006.01) |
| *C09K 11/06* | (2006.01) |
| *C07C 211/61* | (2006.01) |
| *C07C 217/80* | (2006.01) |
| *C07D 307/91* | (2006.01) |
| *H05B 33/14* | (2006.01) |
| *C07F 7/08* | (2006.01) |
| *C07D 471/04* | (2006.01) |
| *C07F 7/00* | (2006.01) |

(52) U.S. Cl.
CPC .......... *C07C 211/54* (2013.01); *C07C 211/61* (2013.01); *C07C 217/80* (2013.01); *C07C 255/58* (2013.01); *C07D 209/88* (2013.01); *C07D 213/74* (2013.01); *C07D 307/91* (2013.01); *C07D 471/04* (2013.01); *C07F 7/00* (2013.01); *C07F 7/081* (2013.01); *C07F 7/0805* (2013.01); *C09K 11/06* (2013.01); *H01L 51/006* (2013.01); *H01L 51/0058* (2013.01); *H01L 51/0067* (2013.01); *H01L 51/0072* (2013.01); *H01L 51/0073* (2013.01); *H01L 51/5012* (2013.01); *H01L 51/5092* (2013.01); *H01L 51/5096* (2013.01); *H01L 51/5203* (2013.01); *H05B 33/14* (2013.01); *C07B 2200/05* (2013.01); *C07C 2601/14* (2017.05); *C07C 2602/10* (2017.05); *C07C 2603/12* (2017.05); *C07C 2603/18* (2017.05); *C07C 2603/24* (2017.05); *C07C 2603/42* (2017.05); *C07C 2603/74* (2017.05); *C07C 2603/94* (2017.05); *H01L 51/0061* (2013.01); *H01L 51/5056* (2013.01); *H01L 51/5072* (2013.01)

(58) Field of Classification Search
None
See application file for complete search history.

(56) References Cited

U.S. PATENT DOCUMENTS

2009/0200926 A1*  8/2009  Lee .................. C07C 211/61
                                                    313/504
2016/0181535 A1   6/2016  Tsuji et al.

FOREIGN PATENT DOCUMENTS

| CN | 101531599 | 9/2009 |
|---|---|---|
| CN | 101575259 | 11/2009 |
| CN | 102224217 | 10/2011 |
| CN | 102574871 | 7/2012 |
| CN | 103298800 | 9/2013 |
| JP | H07-145116 | 6/1995 |
| JP | H09-509156 | 9/1997 |
| JP | 2002-124385 | 4/2002 |
| JP | 2007-077064 | 3/2007 |
| JP | 2009-149638 | 7/2009 |
| JP | 2009-185024 | 8/2009 |
| JP | 4470508 | 6/2010 |
| JP | 4649752 | 3/2011 |
| JP | 2013-539205 | 10/2013 |
| JP | 5551369 | 7/2014 |
| JP | 2015-529970 | 10/2015 |
| JP | 2015-530735 | 10/2015 |
| JP | 2016-119340 | 6/2016 |
| KR | 10-2008-0104996 | 12/2008 |
| KR | 10-2009-0051647 | 5/2009 |
| KR | 10-2009-0058063 | 6/2009 |

(Continued)

OTHER PUBLICATIONS

International Search Report prepared by the Korean Intellectual Property Office dated Apr. 14, 2017, for International Application No. PCT/KR2016/015485.

*Primary Examiner* — Gregory D Clark
(74) *Attorney, Agent, or Firm* — Sheridan Ross P.C.

(57) ABSTRACT

The present invention relates to an adamantane derivative compound and an organic light-emitting diode (OLED) including the same, and more particularly, to an adamantane derivative compound capable of being used in an OLED and an OLED having excellent properties such as low voltage and high efficiency using the compound.

11 Claims, No Drawings

(56) References Cited

FOREIGN PATENT DOCUMENTS

KR     10-2012-0011445     2/2012
KR     10-2016-0074382     6/2016

* cited by examiner

ORGANIC COMPOUND AND ORGANIC ELECTROLUMINESCENT ELEMENT COMPRISING SAME

CROSS REFERENCE TO RELATED APPLICATIONS

This application is a national stage application under 35 U.S.C. 371 and claims the benefit of PCT Application No. PCT/KR2016/015485 having an international filing date of 29 Dec. 2016, which designated the United States, which PCT application claimed the benefit of the Republic of Korea Application No. 10-2015-0191316 filed 31 Dec. 2015, and the Republic of Korea Application No. 10-2016-0125568 filed 29 Sep. 2016, the disclosure of each of which are incorporated herein by reference.

TECHNICAL FIELD

The present invention relates to a novel organic compound and an organic light-emitting diode (OLED) including the same, and more particularly, to an adamantane derivative compound with high thermal resistance, and excellent chemical stability, excellent charge mobility and an excellent interfacial property with an electrode or an adjacent layer, and an OLED which includes the adamantane derivative compound as a material for one or more organic material layers, thereby exhibiting excellent properties such as a low driving voltage, excellent light emitting efficiency, excellent external quantum efficiency (EQE) and excellent thermal stability.

BACKGROUND ART

An OLED is being actively developed to be used as a backlight for flat panel displays such as a wall-mounted TV or other displays, a light source for lighting equipment or advertising boards, etc. due to a simple structure, various advantages in a manufacturing process, high brightness, a wide viewing angle, a fast response speed, and a low driving voltage, compared with the existing other flat panel displays, such as a liquid crystal display (LCD), a plasma display panel (PDP) and a field emission display (FED).

Generally, when a voltage is supplied to an OLED, an exciton, which is an electron-hole pair, is formed through recombination of holes injected from an anode and electrons injected from a cathode, and energy of the exciton is transferred to a light emitting material and converted into light.

To increase the efficiency and stability of an OLED, since a low-voltage-driven OLED consisting of an organic multilayer thin film between two counter electrodes was reported at Eastman Kodak (C. W. Tang, S. A. Vanslyke, Applied Physics Letters, Vol. 51, 1987, 913), a variety of studies on organic materials for a multilayer thin film-type OLED have been actively conducted.

Generally, an OLED has a structure including a cathode (electron injection electrode), an anode (hole injection electrode), and one or more organic layers between these two electrodes. Here, in the OLED, a hole injection layer (HIL), a hole transport layer (HTL), a light emitting layer (EML), an electron transport layer (ETL), and an electron injection layer (EIL) are sequentially laminated from the anode, and in order to increase the efficiency of an EML, an electron blocking layer (EBL) or a hole blocking layer (HBL) may be further included before and after the EML.

Most of the materials used in an OLED are pure organic materials or complex compounds made of a complex between an organic material and a metal, and may be classified into a hole injection material, a hole transport material, a light emitting material, an electron transport material, and an electron injection material according to its intended use. Here, as a hole injection material or a hole transport material, an organic material that is easily oxidized and electrochemically stable in oxidation is usually used. Meanwhile, as an electron injection material or an electron transport material, an organic material that is easily reduced and electrochemically stable in reduction is usually used. An EML material is preferably a material that is stable in both oxidation and reduction, and has high light emitting efficiency, which is the efficiency of converting a formed exciton into light.

In addition to these properties, it is preferable that the materials used in an OLED have the following properties.

First, the materials used in an OLED need to have a high glass transition temperature (Tg). During driving, localized heat generation in the diode caused by Joule heating leads to changes in the properties of the diode. In addition, the OLED that has undergone a deposition process is subjected to a thermal treatment process at 100 to 120° C., resulting in crystallization of a material having a low glass transition temperature. A conventionally-used hole transport material, for example, TPD or NPB, has a low glass transition temperature (Tg), such as 60 or 96° C., respectively, and therefore it experiences the same phenomenon as described above during driving or a post-process. The crystallization breaks a charge balance, leading to a reduction in current efficiency.

Second, the organic material used in an OLED should not have absorption in the visible light region. Particularly, the light absorption should not occur at 450 nm or more. This is because, when light generated from an EML is absorbed, light emitting efficiency is reduced.

Third, the organic material used in an OLED requires considerably high thermal stability in deposition. Generally, in a process of manufacturing an OLED panel, an organic material is used for at least a week (approximately 144 hours) with one filling. Since the filling amount of the organic material is reduced over time, a deposition temperature needs to be raised to constantly maintain a deposition speed. Here, if there is a problem in diode performance due to decomposition of the organic material, such a material cannot be used even though it has a high glass transition temperature and no absorption in a visible light region.

There is a continuing demand for the development of a novel material suitable for mass production, having excellent thermal and electro-optical properties described above, high efficiency and a long lifespan in the art.

PRIOR ART DOCUMENTS

Japanese Patent Nos. 4649752, 4470508 and 5551369, and Korean Unexamined Patent Application Publication No. 2008-0104996

DISCLOSURE

Technical Problem

The present invention is directed to providing a novel compound which has low crystallinity, high thermal resistance and excellent chemical stability and thus can be used as a HIL, HTL or EBL material.

The present invention is also directed to providing an OLED which includes the novel compound, and thus exhibits a low driving voltage, excellent light emitting efficiency, excellent external quantum efficiency (EQE) and excellent thermal stability.

Technical Solution

To achieve the above-mentioned objects, the present invention provides a compound represented by Formula 1 below:

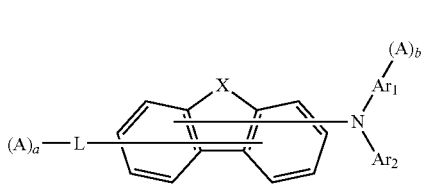

[Formula 1]

Here,
each of a and b is an integer of 0 or 1 (a+b≥1),
A is a substituted or unsubstituted adamantyl group,
X is selected from the group consisting of $N(R_1)$, S, O, $C(R_1)(R_2)$ and $Si(R_1)(R_2)$,
$R_1$ and $R_2$ are the same or different, and each independently selected from the group consisting of hydrogen, deuterium, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, and a substituted or unsubstituted heteroarylalkyl group having 3 to 30 carbon atoms,
$R_1$ and $R_2$ may be connected to each other, forming a saturated or unsaturated ring compound,
L is selected from the group consisting of a single bond, a substituted or unsubstituted arylene group having 6 to 30 carbon atoms, a substituted or unsubstituted heteroarylene group having 6 to 30 nuclear carbon atoms, a substituted or unsubstituted alkylene group having 2 to 10 carbon atoms, a substituted or unsubstituted cycloalkylene group having 2 to 10 carbon atoms, a substituted or unsubstituted alkenylene group having 2 to 10 carbon atoms, a substituted or unsubstituted cycloalkenylene group having 2 to 10 carbon atoms substituted or unsubstituted heteroalkylene group having 2 to 10 carbon atoms, a substituted or unsubstituted heterocycloalkylene group having 2 to 10 carbon atoms, a substituted or unsubstituted heteroalkenylene group having 2 to 10 carbon atoms, and substituted or unsubstituted heterocycloalkenylene group having 2 to 10 carbon atoms,
$Ar_1$ and $Ar_2$ are the same or different, and each independently selected from the group consisting of a substituted or unsubstituted aryl group having 6 to 30 carbon atoms, a substituted or unsubstituted heteroaryl group having 3 to 30 carbon atoms, a substituted or unsubstituted alkyl group having 1 to 20 carbon atoms, a substituted or unsubstituted cycloalkyl group having 1 to 20 carbon atoms, a substituted or unsubstituted heteroalkyl group having 1 to 20 carbon atoms, a substituted or unsubstituted heterocycloalkyl group having 1 to 20 carbon atoms, a substituted or unsubstituted alkenyl group having 1 to 20 carbon atoms, a substituted or unsubstituted cycloalkenyl group having 1 to 20 carbon atoms and a substituted or unsubstituted heteroalkenyl group having 1 to 20 carbon atoms, and
the substituents of $R_1$ to $R_2$, A, L and $Ar_1$ to $Ar_2$ are the same or different, and each independently selected from the group consisting of deuterium, a cyano group, a nitrile group, a halogen group, a hydroxyl group, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, a substituted or unsubstituted heteroarylalkyl group having 3 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl group having 6 to 30 carbon atoms and a substituted or unsubstituted aryloxy group having 6 to 30 carbon atoms.

More preferably, A is a compound represented by Formula 2 below, or a compound represented by Formula 3 below:

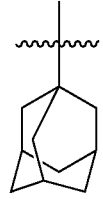

[Formula 2]

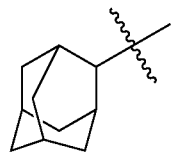

[Formula 3]

In addition, the present invention provides an OLED including a first electrode; a second electrode placed opposite to the first electrode; and one or more organic material layers placed between the first electrode and the second electrode, and more particularly, an OLED in which at least one of the one or more organic material layers includes the compound represented by Formula 1.

For example, the OLED may have a structure including a HIL, a HTL, an EBL, an EML, a HBL, an ETL, an EIL, etc. However, the structure of the OLED is not limited thereto, and thus may include a smaller number of organic layers.

According to an exemplary embodiment of the present invention, the organic material layer including the compound represented by Formula 1 is a HIL, HTL or EBL.

The "alkyl" used herein refers to a monovalent substituent derived from a linear or branched saturated hydrocarbon having 1 to 40 carbon atoms. As an example, the alkyl may be, but is not limited to, methyl, ethyl, propyl, isobutyl, sec-butyl, pentyl, iso-amyl or hexyl.

The "alkenyl" used herein refers to a monovalent substituent derived from a linear or branched unsaturated hydrocarbon having 2 to 40 carbon atoms and one or more carbon-carbon double bonds. As an example, the alkenyl may be, but is not limited to, vinyl, allyl, isopropenyl or 2-butenyl.

The "alkynyl" used herein refers to a monovalent substituent derived from a linear or branched unsaturated hydrocarbon having 2 to 40 carbon atoms and one or more carbon-carbon triple bonds. As an example, the alkynyl may be, but is not limited to, ethynyl or 2-propynyl.

The "aryl" used herein refers to a monovalent substituent derived from an aromatic hydrocarbon having 6 to 60 carbon atoms and a single ring or a combination of two or more rings. In addition, the aryl may be a monovalent substituent derived from an aromatic hydrocarbon in which two or more rings are simply pendant to or condensed with each other. As an example, the aryl may be, but is not limited to, phenyl, naphthyl, phenanthryl, anthryl or dimethylfluorenyl.

The "heteroaryl" used herein refers to a monovalent substituent derived from a monoheterocyclic or polyheterocyclic aromatic hydrocarbon having 5 to 60 nuclear carbon atoms. Here, one or more, preferably, 1 to 3 carbon atoms of the ring are substituted with heteroatoms such as N, O, S or Se. In addition, 2 or more rings may be simply pendant to or condensed with each other, or a ring may be condensed with an aryl group. An example of the heteroaryl may be, but is not limited to, a 6-membered monocyclic ring such as pyridyl, pyrazinyl, pyrimidinyl, pyridazinyl or triazinyl, a polycyclic ring such as phenoxathienyl, indolizinyl, indolyl, purinyl, quinolyl, benzothiazole or carbazolyl, 2-furanyl, N-imidazolyl, 2-isoxazolyl, 2-pyridinyl, or 2-pyrimidinyl.

The "aryloxy" used herein refers to a monovalent substituent represented by RO—, in which R represents an aryl having 6 to 60 carbon atoms. An example of the aryloxy may be, but is not limited to, phenyloxy, naphthyloxy, or diphenyloxy.

The "alkyloxy" used herein refers to a monovalent substituent represented by R'O—, in which R' represents an alkyl having 1 to 40 carbon atoms, and may include a linear, branched or cyclic structure. An example of the alkyloxy may be, but is not limited to, methoxy, ethoxy, n-propoxy, 1-propoxy, t-butoxy, n-butoxy, or pentoxy.

The "arylamine" used herein refers to an amine substituted with an aryl having 6 to 60 carbon atoms.

The "cycloalkyl" used herein refers to a monovalent substituent derived from a monocyclic or polycyclic non-aromatic hydrocarbon having 3 to 40 carbon atoms. An example of the cycloalkyl may be, but is not limited to, cyclopropyl, cyclobutyl, cyclopentyl, cyclohexyl, norbornyl, or adamantine.

The "heterocycloalkyl" used herein refers to a monovalent substituent derived from a non-aromatic hydrocarbon having 3 to 40 nuclear carbon atoms, and one or more carbons, preferably, 1 to 3 carbon atoms of the ring are substituted with heteroatoms such as N, O, S or Se. An example of the heterocycloalkyl may be, but is not limited to, morpholine or piperazine.

The "alkylsilyl" used herein refers to silyl substituted with alkyl having 1 to 40 carbon atoms, and the "arylsilyl" used herein refers to silyl substituted with an aryl having 6 to 60 carbon atoms.

The "condensed ring" used herein refers to a condensed aliphatic ring, a condensed aromatic ring, a condensed heteroaliphatic ring, a condensed heteroaromatic ring or a combination thereof.

Advantageous Effects

A compound provided in the present invention has low crystallinity, high thermal resistance, excellent chemical stability, a suitable bandgap and a suitable HOMO or LUMO energy level, and thus can be effectively used as an organic material layer material of an OLED.

In addition, the OLED including the novel compound according to the present invention has a low driving voltage, excellent light emitting efficiency, excellent external quantum efficiency (EQE) and excellent thermal stability.

MODES OF THE INVENTION

Hereinafter, the present invention will be described in detail.

An adamantane derivative compound according to the present invention has adamantane and a triple-substituted amine structure in an entire compound structure. The adamantane derivative compound of the present invention is prepared by forming each functional molecule having a hole injection or hole transport characteristic as an adamantane derivative, and has preferably low crystallinity and high thermal resistance as an OLED material. The feature of the adamantane structure is that a single molecular structure thereof is highly non-planar compared to a cycloalkyl or aryl structure. Generally, a non-planar structure like a long-chain alkyl group has energy loss due to mobility caused by the rotation or vibration of a molecule. In contrast, since the adamantane has stereoscopically rigid condensed rings despite its characteristic of low crystallinity, the molecular mobility may be reduced. Due to such characteristics, the adamantane may have high thermal resistance, and energy loss caused by mobility may be reduced. In addition, while an aryl structure such as a phenyl structure affects an energy level due to a delocalized structure, the adamantane structure does not have an influence on an energy level according to delocalization and has more carbon atoms and thus has a larger molecular weight than the phenyl structure. Accordingly, the adamantane structure has a higher melting point and a higher glass transition temperature than the phenyl structure, and thus thin film stability may also be enhanced.

Particularly, the compound represented by Formula 1 below is as follows:

[Formula 1]

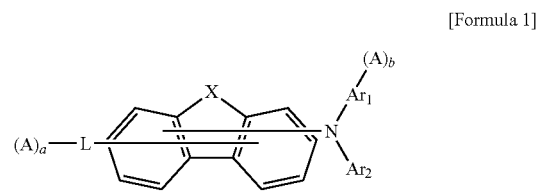

Here, each of a and b is an integer of 0 or 1 (a+b≥1),

A is a substituted or unsubstituted adamantyl group,

X is selected from the group consisting of $N(R_1)$, S, O, $C(R_1)(R_2)$ and $Si(R_1)(R_2)$, $R_1$ and $R_2$ are the same or different, and each independently selected from the group consisting of hydrogen, deuterium, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, and a substituted or unsubstituted heteroarylalkyl group having 3 to 30 carbon atoms, $R_1$ and $R_2$ may be connected to each other, forming a saturated or unsaturated ring compound, L is selected from the group consisting of a single bond, a substituted or unsubstituted arylene group having 6 to 30 carbon atoms, a substituted or unsubstituted a heteroarylene group having 6 to 30 nuclear carbon atoms, a substituted or unsubstituted alkylene group having 2 to 10 carbon atoms, a substituted or unsubstituted cycloalkylene group having 2 to 10 carbon atoms, a substituted or unsubstituted alkenylene group having 2 to 10 carbon atoms, a substituted or unsubstituted cycloalkenylene group having 2 to 10 carbon atoms substituted or unsubstituted heteroalkylene group having 2 to 10 carbon atoms, a substituted or unsubstituted heterocycloalkylene group having 2 to 10 carbon atoms, a substituted or unsubstituted heteroalkenylene group having 2 to 10 carbon atoms, and a substituted or unsubstituted heterocycloalkenylene group having 2 to 10 carbon atoms, $Ar_1$ and $Ar_2$ are the same or different, and each independently selected from the group consisting of a substituted or unsubstituted aryl group having 6 to 30 carbon atoms, a substituted or unsubstituted heteroaryl group having 3 to 30 carbon atoms, a substituted or unsubstituted alkyl group having 1 to 20 carbon atoms, a substituted or unsubstituted cycloalkyl group having 1 to 20 carbon atoms, a substituted or unsubstituted heteroalkyl group having 1 to 20 carbon atoms, a substituted or unsubstituted heterocycloalkyl group having 1 to 20 carbon atoms, a substituted or unsubstituted alkenyl group having 1 to 20 carbon atoms, a substituted or unsubstituted cycloalkenyl group having 1 to 20 carbon atoms, and a substituted or unsubstituted heteroalkenyl group having 1 to 20 carbon atoms, and.

the substituents of $R_1$ to $R_2$, A, L and $Ar_1$ to $Ar_2$ are the same or different, and each independently selected from the group consisting of deuterium, a cyano group, a nitro group, a halogen group, a hydroxyl group, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, a substituted or unsubstituted heteroarylalkyl group having 3 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl group having 6 to 30 carbon atoms, and a substituted or unsubstituted aryloxy group having 6 to 30 carbon atoms.

More preferably, A is a compound represented by Formula 2 below, or a compound represented by Formula 3 below:

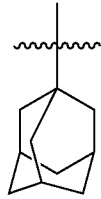

[Formula 2]

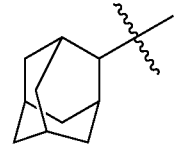

[Formula 3]

In the OLED, since the diffusion distance of triplet excitons in the formation of an EML is long, for example, 100 nm or more, the excitons may depart from the EML having a thickness of 20 to 30 nm, resulting in a significantly decrease in light emitting efficiency. Therefore, it is preferable that the triplet excitons are captured in the EML using a suitable exciton blocking layer. In addition, there is a limitation to the development of a display material because of the thermal stability of the material, and therefore, the material needs to have a glass transition temperature of at least 100° C. or more. The adamantane derivative compound according to the present invention is prepared by forming each functional molecule having a hole injection, hole transport, or electron blocking property as an adamantane derivative, and has low crystallinity and high thermal resistance, which are preferable properties of an OLED material.

According to an exemplary embodiment of the present invention, the compound represented by Formula 1 may be a compound represented by Formula 4 or 5 below:

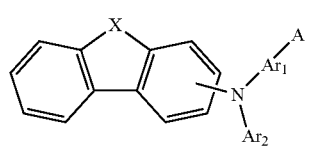

[Formula 4]

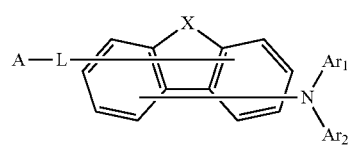

[Formula 5]

Here, each of X, A, L, $Ar_1$ and $Ar_2$ is the same as defined in Formula 1.

According to an exemplary embodiment of the present invention, X is selected from the group consisting of $N(R_1)$, S, O, $Si(R_1)(R_2)$ and $C(R_1)(R_2)$, and is preferably $C(R_1)(R_2)$. However, the present invention is not limited thereto.

In addition, according to an exemplary embodiment of the present invention, when X is $C(R_1)(R_2)$, it has a structural feature that enables a fluorene neighboring an amine in the structure of a trisubstituted arylamine to have a high electron density, and thus a HOMO energy level may be raised to a level suitable for a HTL, and an excellent electrical property may be exhibited.

According to an exemplary embodiment of the present invention, A₁ and Ar₂ are the same or different, and each independently selected from the group consisting of a substituted or unsubstituted aryl group having 6 to 30 carbon atoms, a substituted or unsubstituted heteroaryl group having 3 to 30 carbon atoms, a substituted or unsubstituted alkyl group having 1 to 20 carbon atoms, a substituted or unsubstituted cycloalkyl group having 1 to 20 carbon atoms, a substituted or unsubstituted heteroalkyl group having 1 to 20 carbon atoms, a substituted or unsubstituted heterocycloalkyl group having 1 to 20 carbon atoms, a substituted or unsubstituted alkenyl group having 1 to 20 carbon atoms, a substituted or unsubstituted cycloalkenyl group having 1 to 20 carbon atoms and a substituted or unsubstituted heteroalkenyl group having 1 to 20 carbon atoms, and are preferably a substituted or unsubstituted aryl group having 6 to 30 carbon atoms or a substituted or unsubstituted heteroaryl group having 3 to 30 carbon atoms. However, the present invention is not limited thereto.

According to an exemplary embodiment of the present invention, R₁ and R₂ are the same or different, and are each independently selected from the group consisting of hydrogen, deuterium, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, and a substituted or unsubstituted heteroarylalkyl group having 3 to 30 carbon atoms, and are preferably a substituted or unsubstituted alkyl group having 1 to 30 carbon atoms or a substituted or unsubstituted aryl group having 6 to 30 carbon atoms. R₁ and R₂ may be connected to each other, forming a saturated or unsaturated ring compound, but the present invention is not limited thereto.

According to an exemplary embodiment of the present invention, L is a single bond, a substituted or unsubstituted arylene group having 6 to 30 carbon atoms, a substituted or unsubstituted heteroarylene group having 6 to 30 nuclear carbon atoms, a substituted or unsubstituted alkylene group having 2 to 10 carbon atoms, a substituted or unsubstituted cycloalkylene group having 2 to 10 carbon atoms, a substituted or unsubstituted alkenylene group having 2 to 10 carbon atoms, a substituted or unsubstituted cycloalkenylene group having 2 to 10 carbon atoms substituted or unsubstituted heteroalkylene group having 2 to 10 carbon atoms, a substituted or unsubstituted heterocycloalkylene group having 2 to 10 carbon atoms, a substituted or unsubstituted heteroalkenylene group having 2 to 10 carbon atoms and a substituted or unsubstituted heterocycloalkenylene group having 2 to 10 carbon atoms, and preferably, L is selected from the group consisting of a single bond, a substituted or unsubstituted arylene group having 6 to 30 carbon atoms and a substituted or unsubstituted heteroarylene group having 6 to 30 nuclear carbon atoms, but the present invention is not limited thereto.

The compound represented by Formula 1 according to the present invention may be selected from the group consisting of the following compounds, but the present invention is not limited thereto:

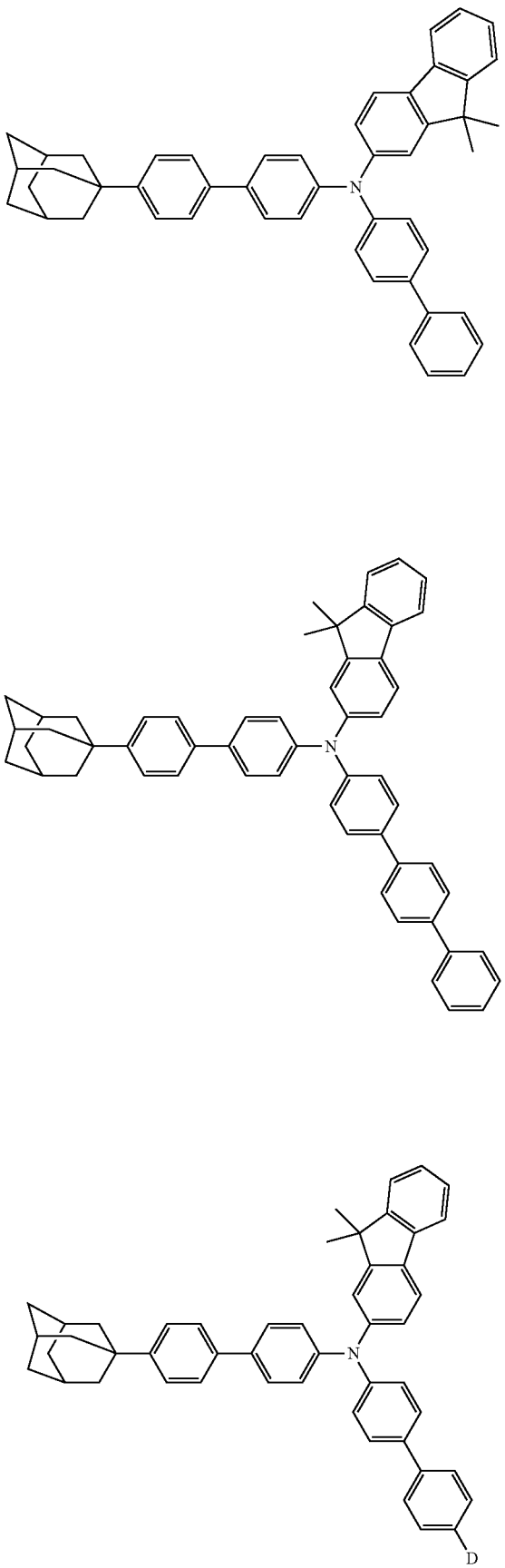

11
-continued
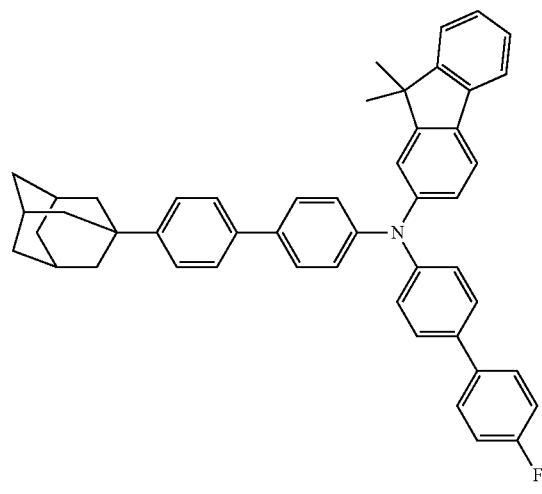
12
-continued
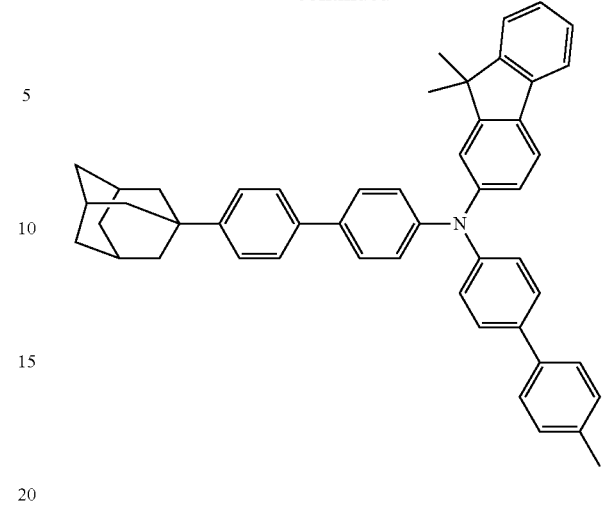
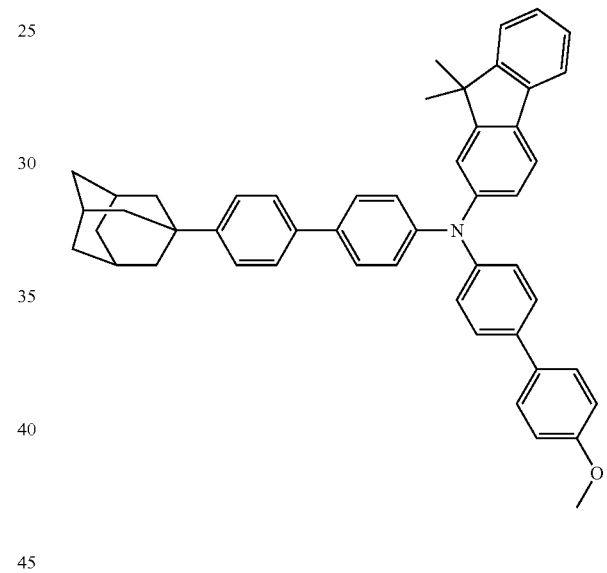
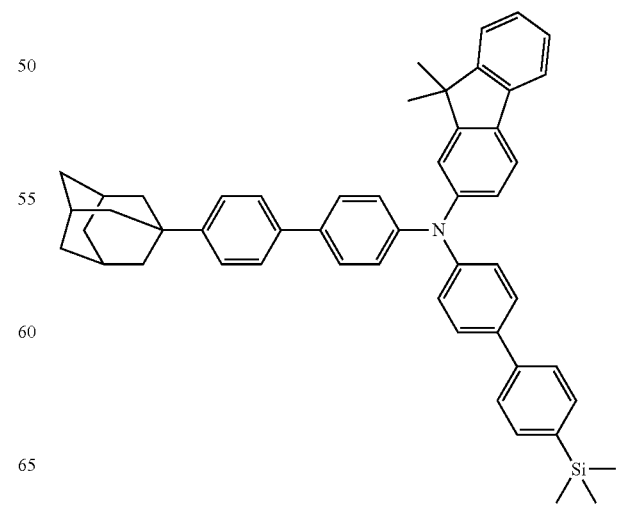

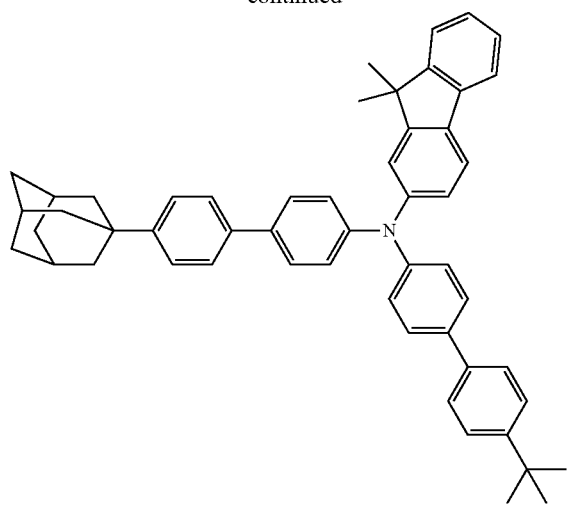
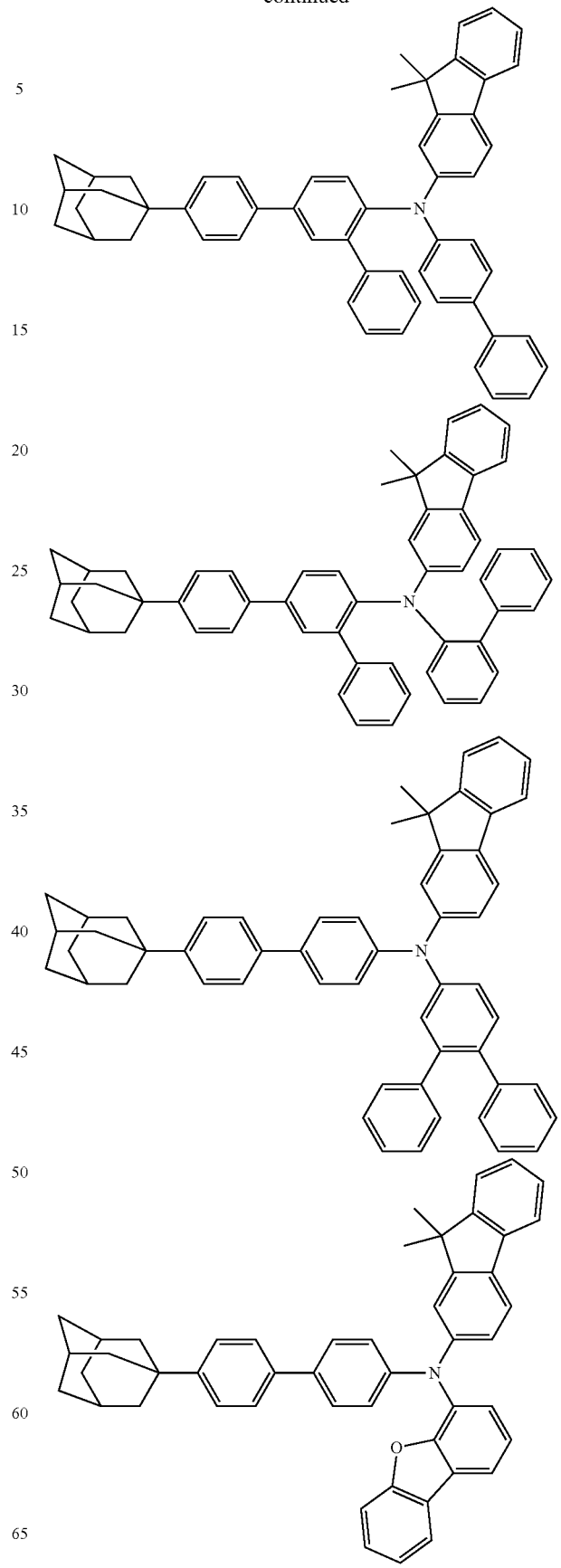

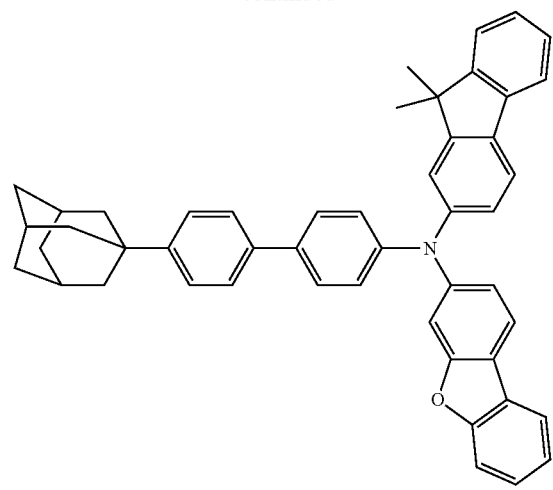
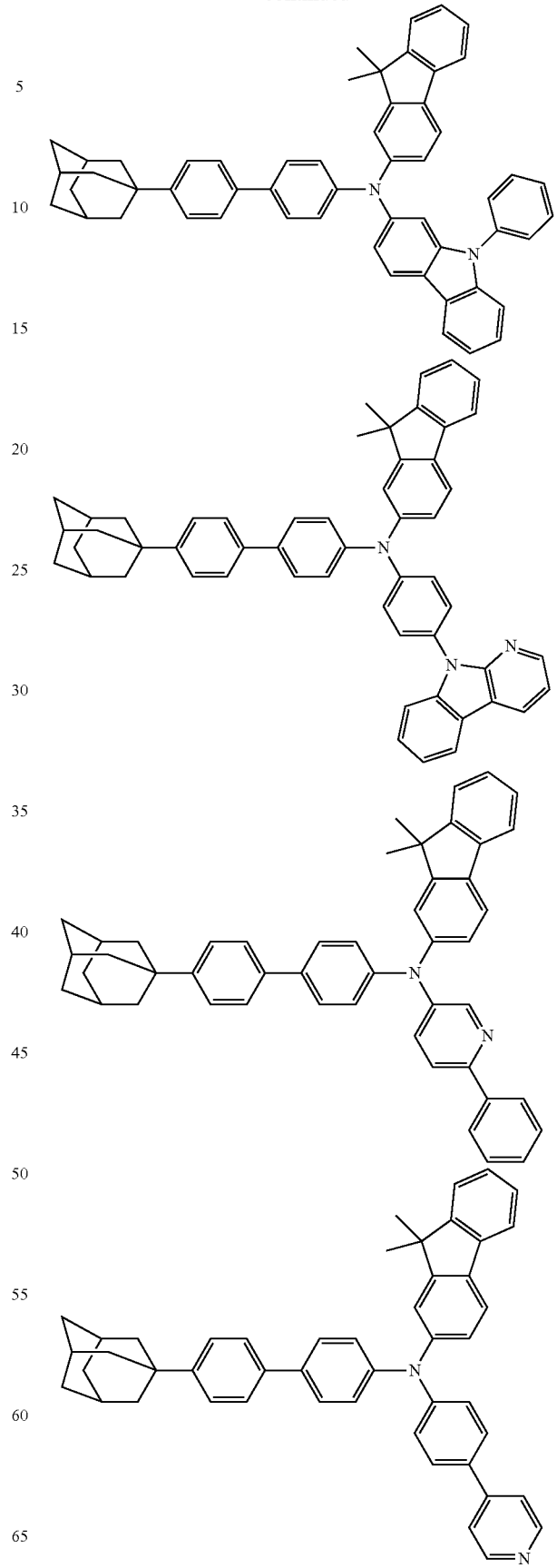

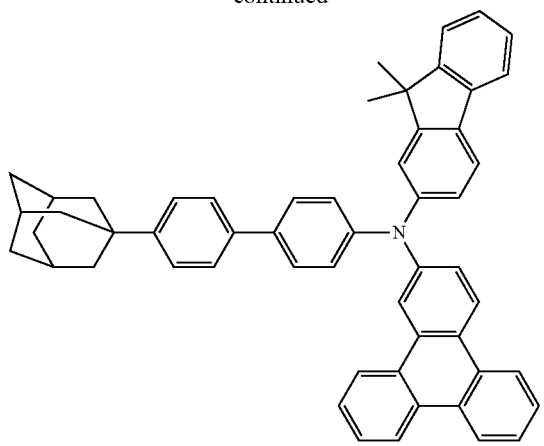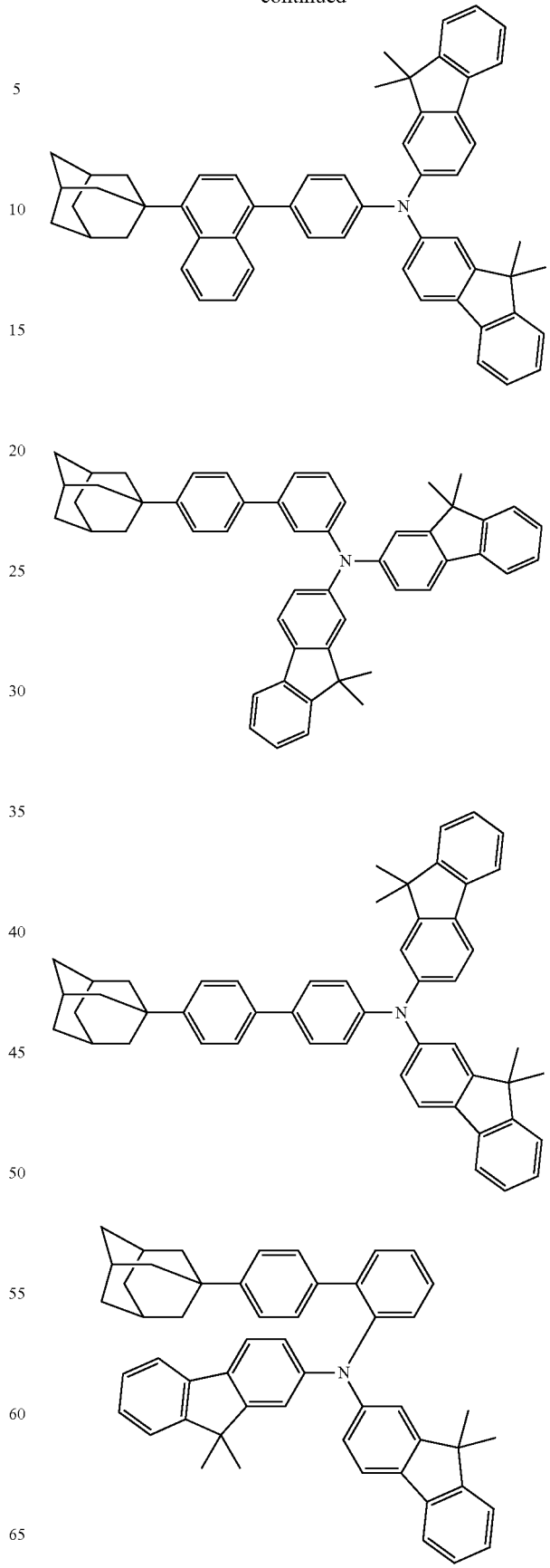

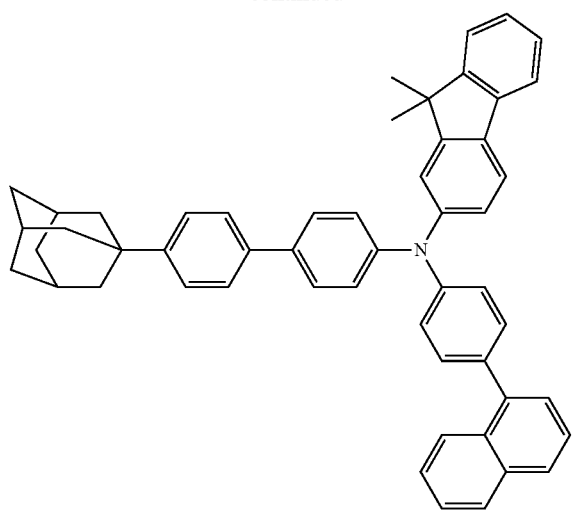
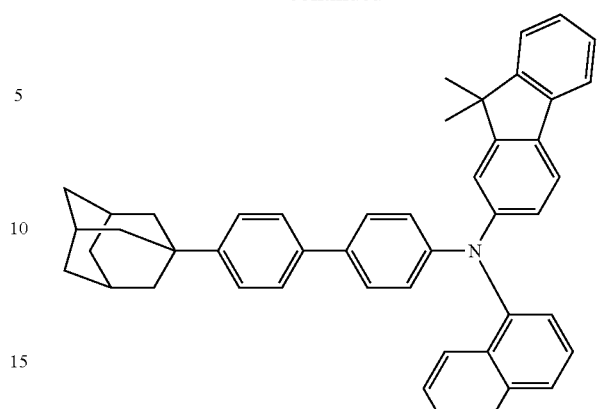
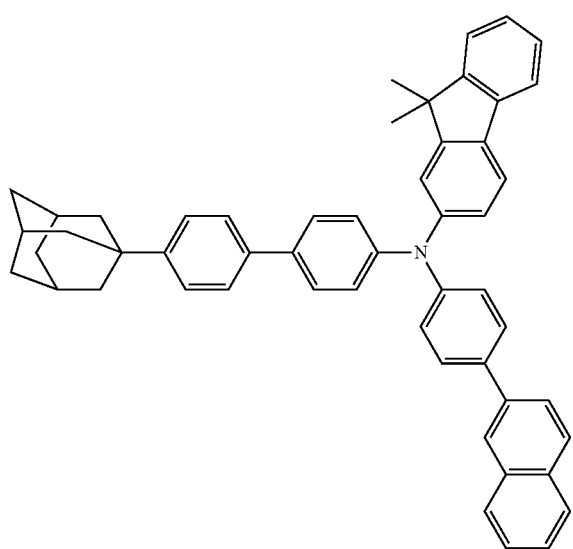
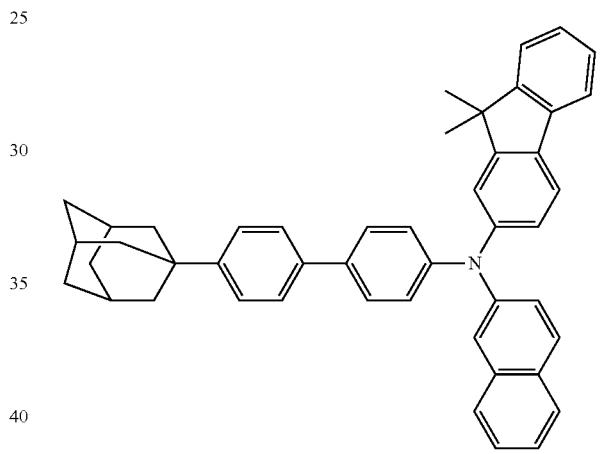
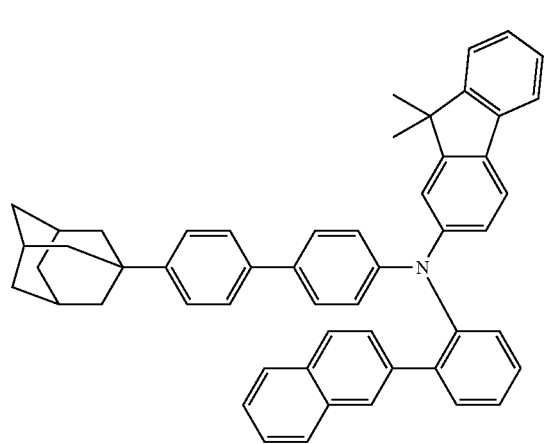
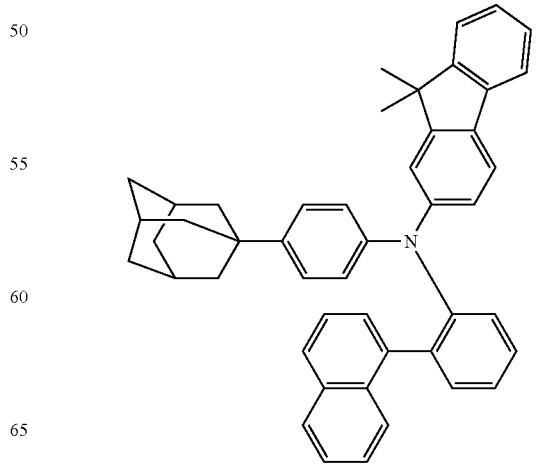

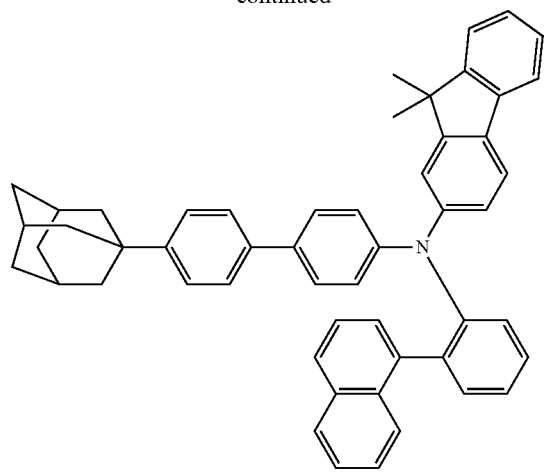
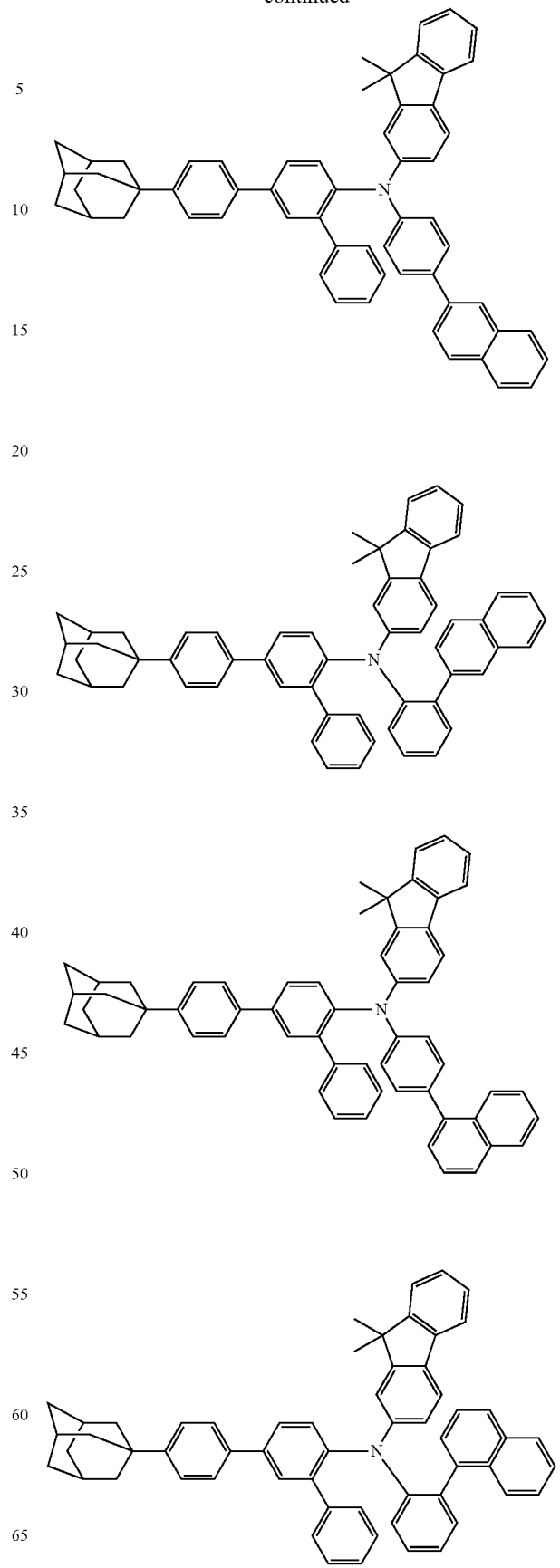

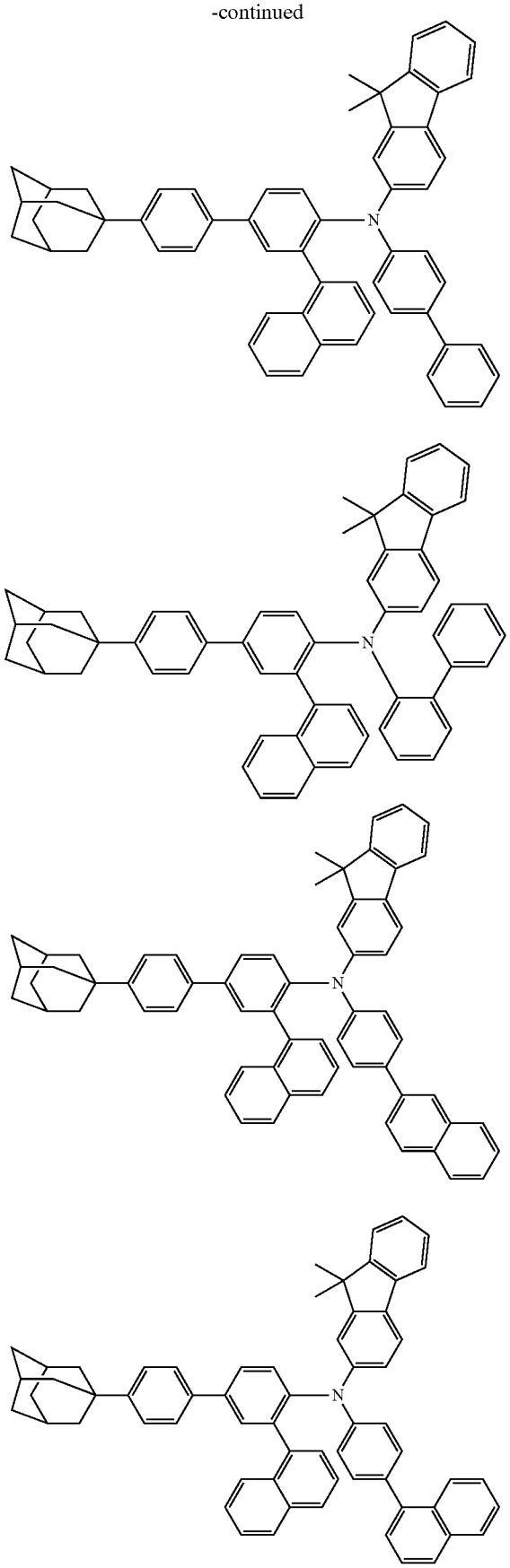
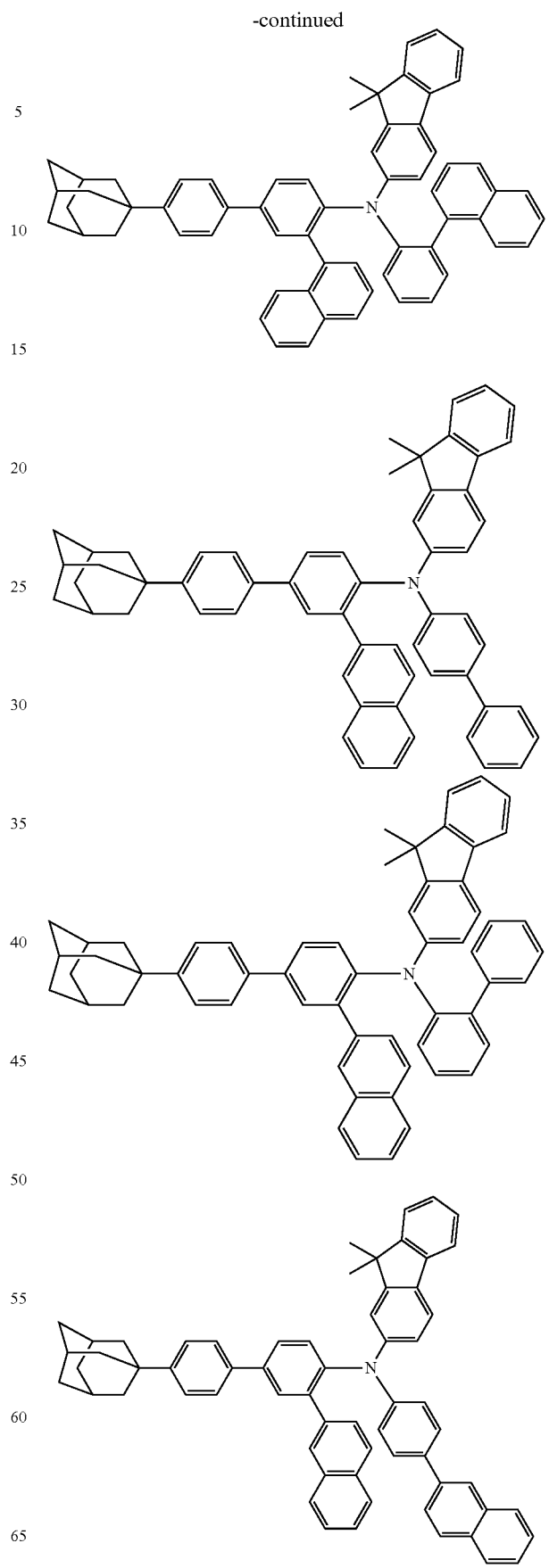

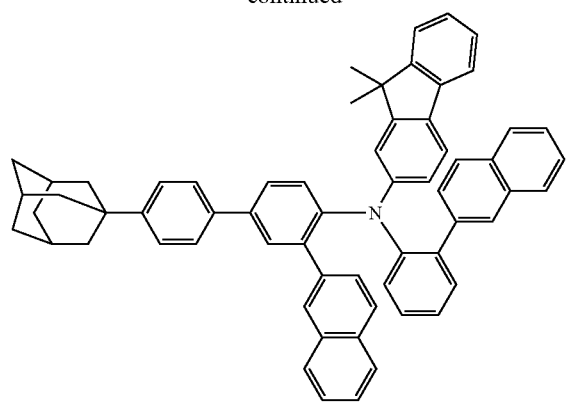
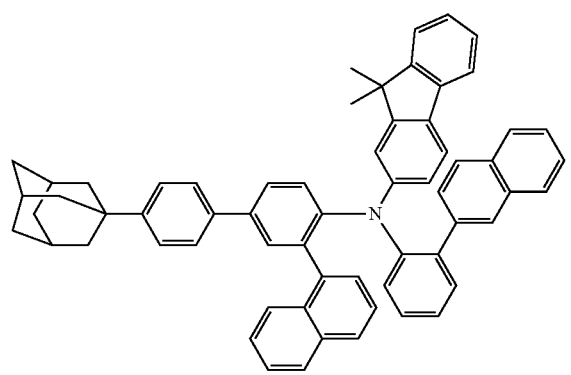
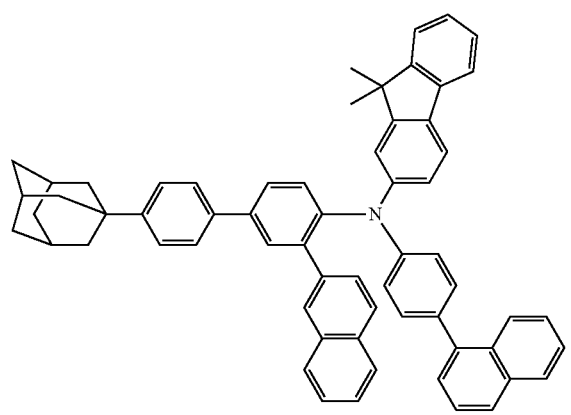
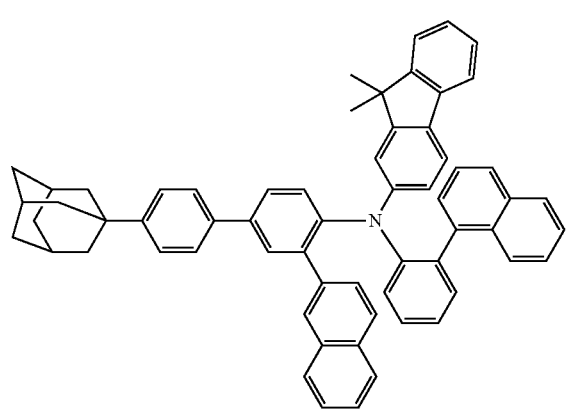
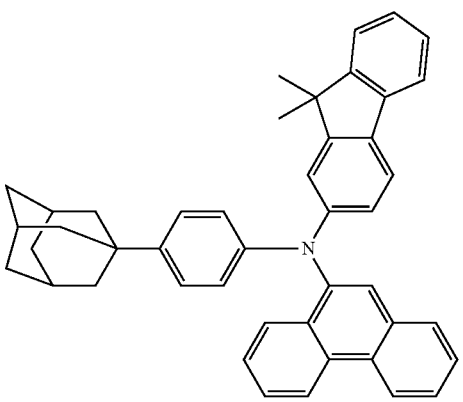
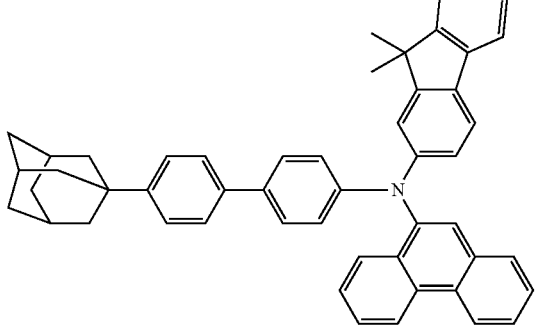
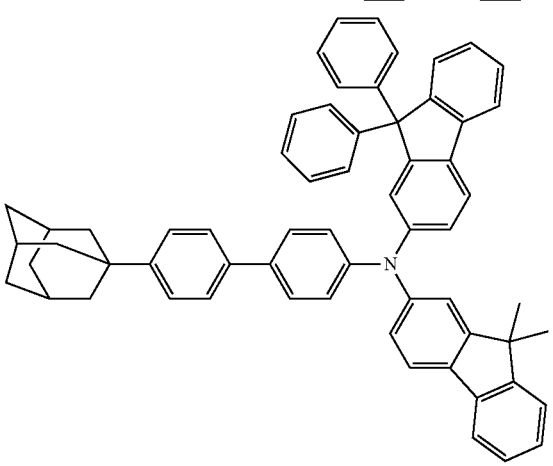
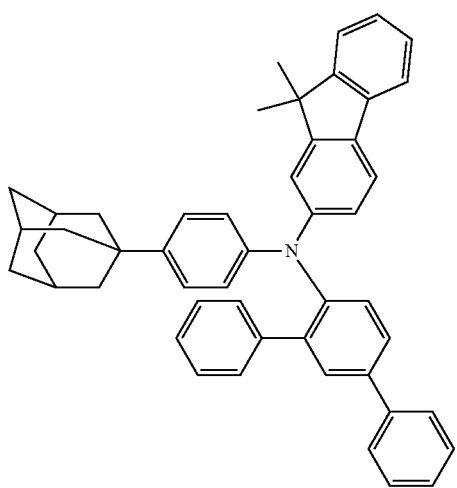

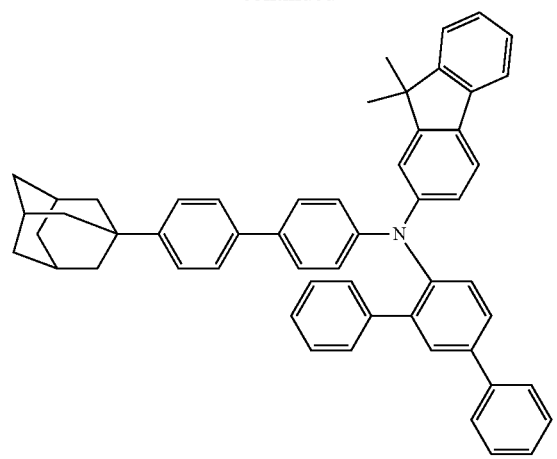
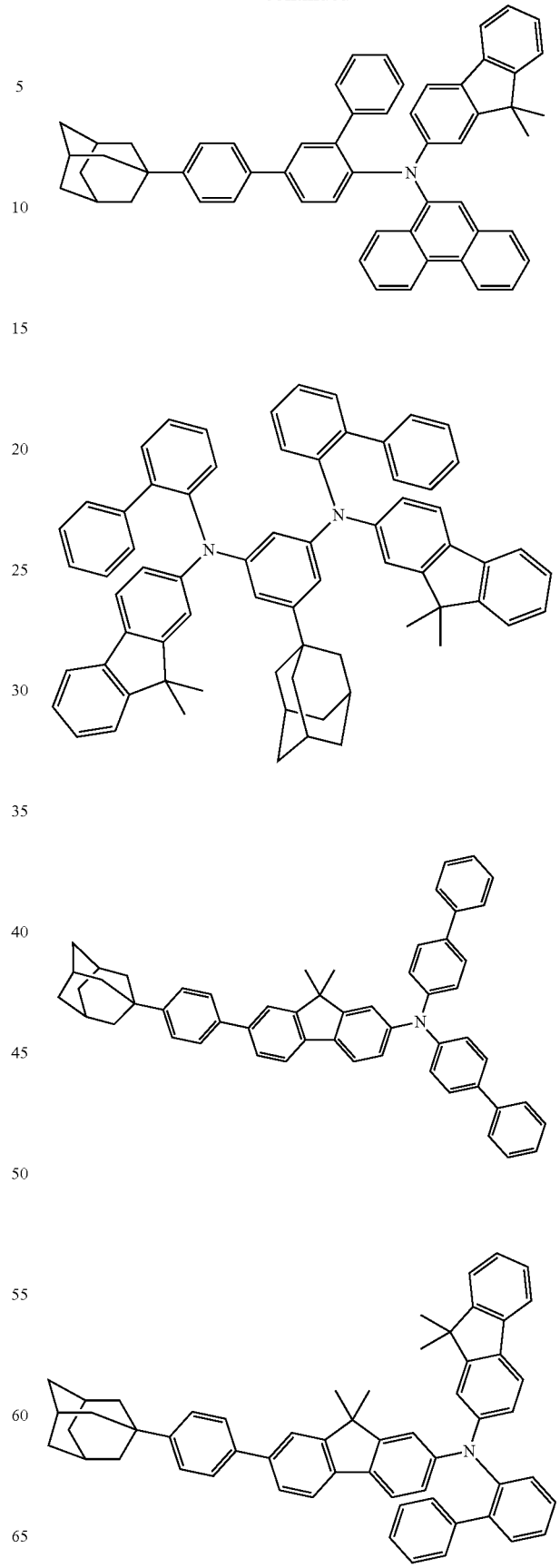

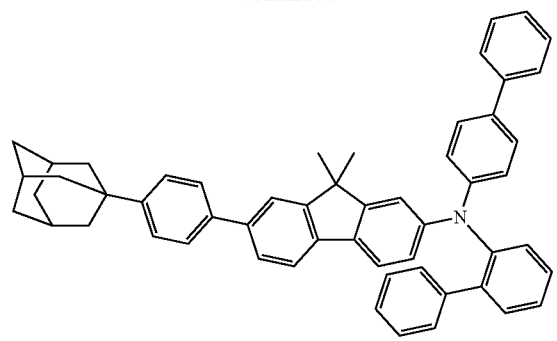
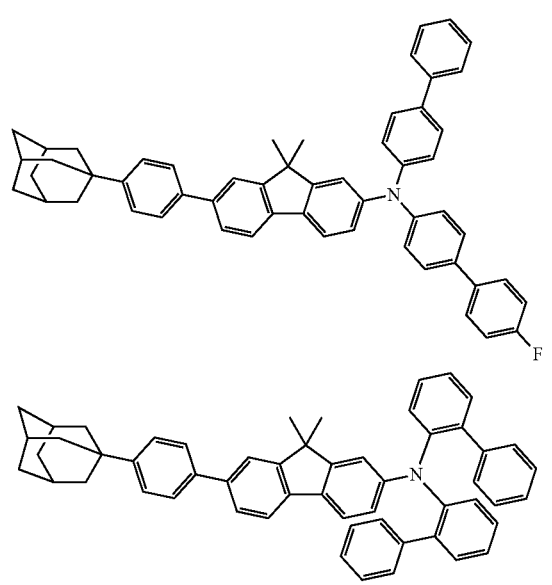
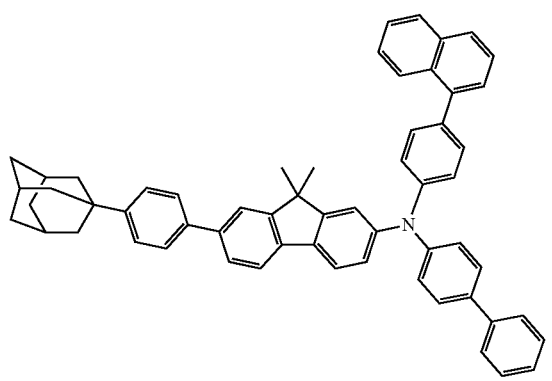
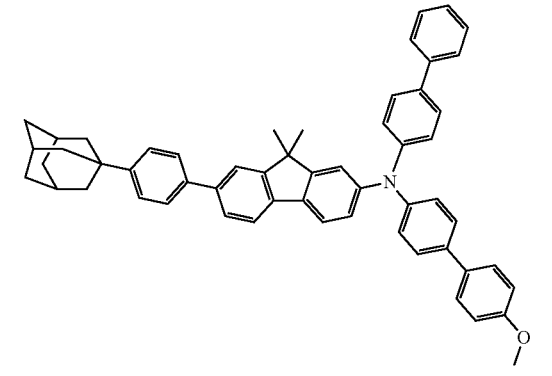
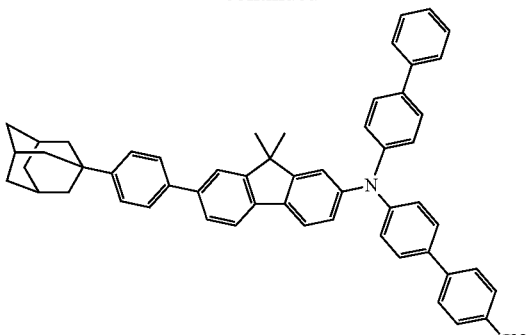
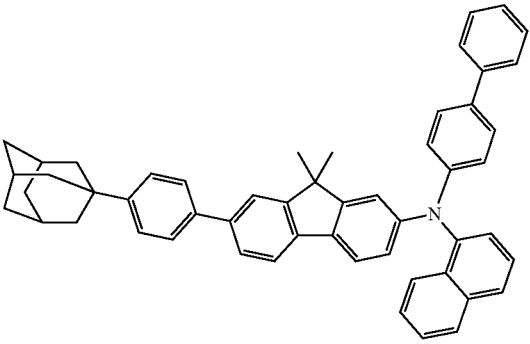
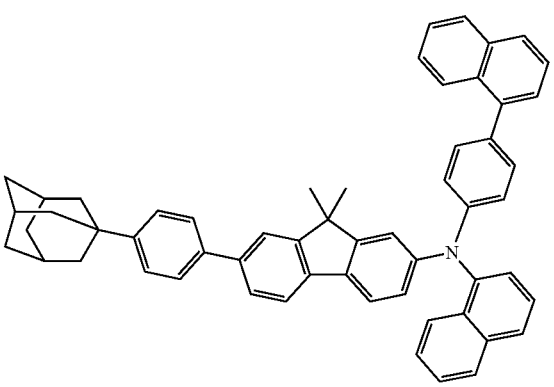
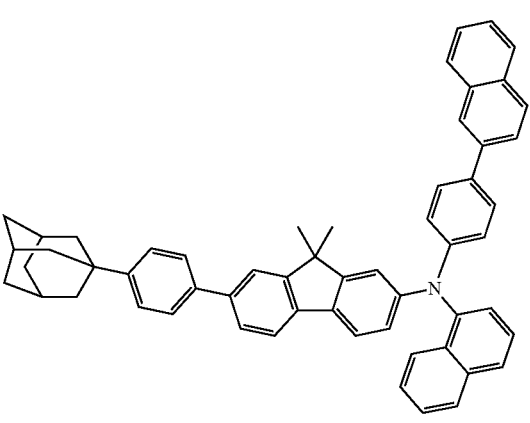

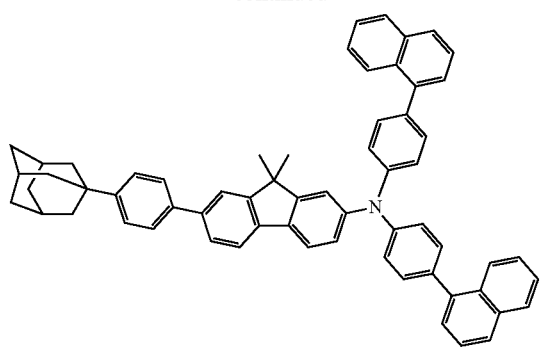
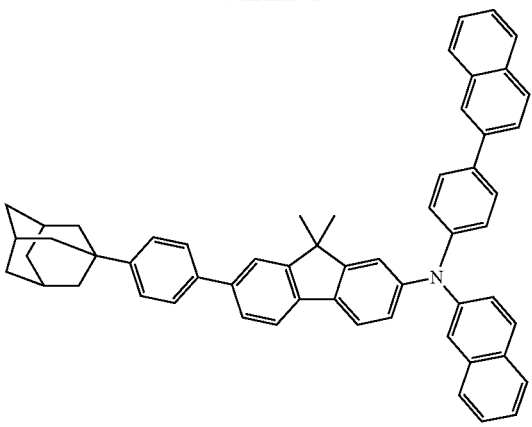

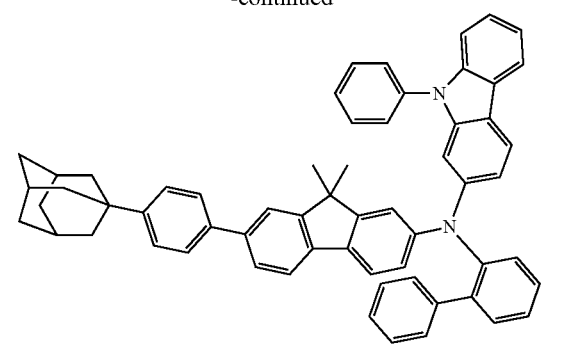
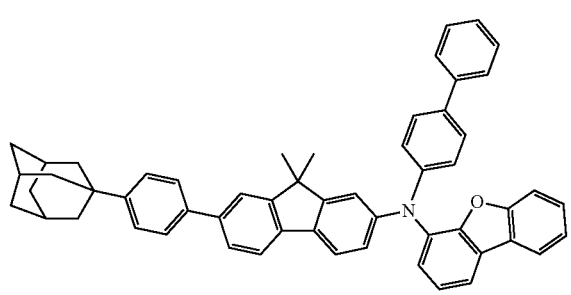
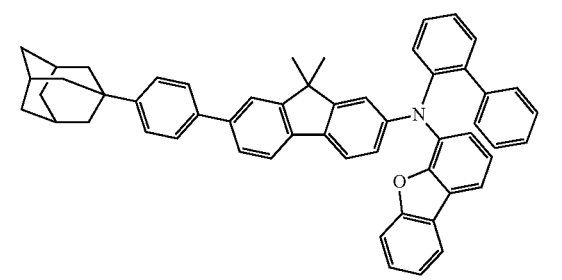
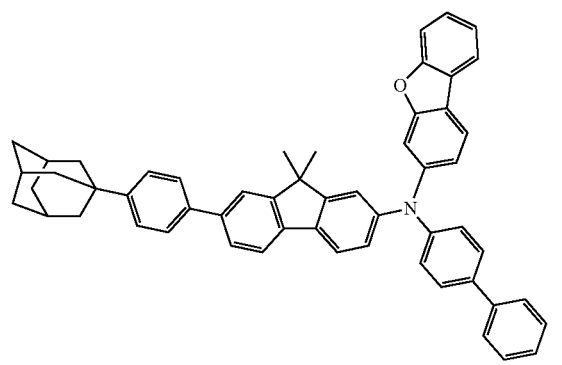
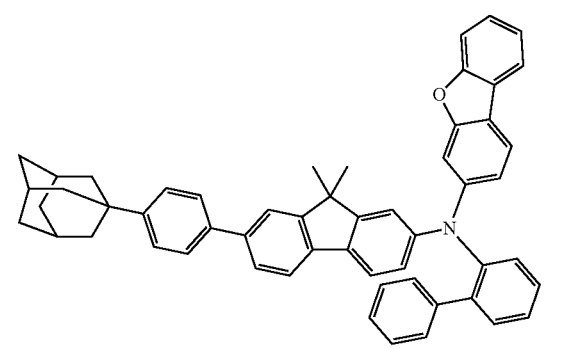
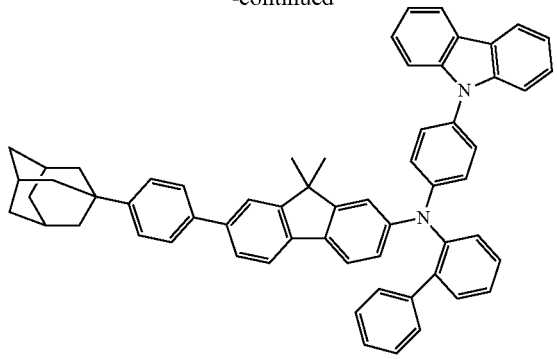
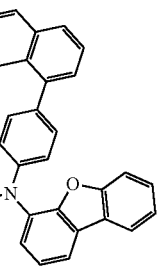
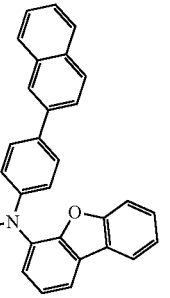
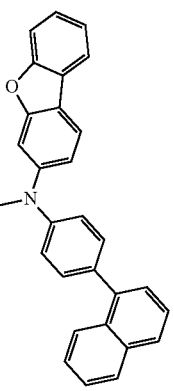
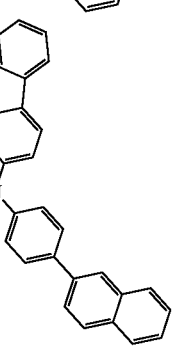

35
-continued
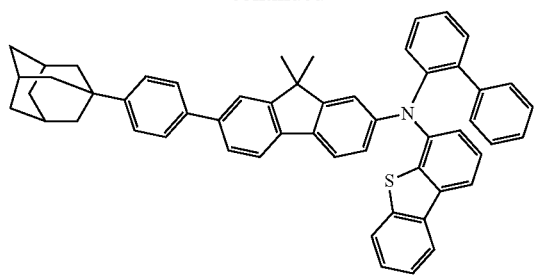
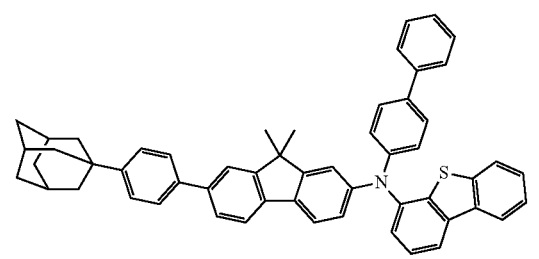
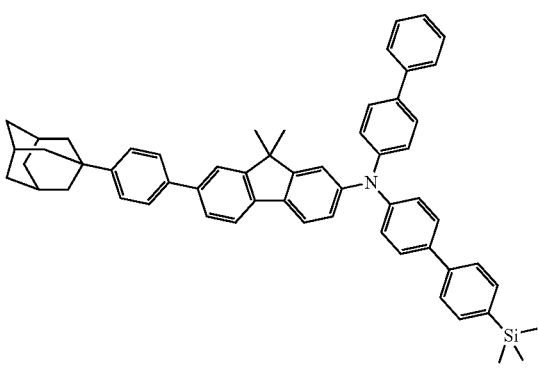
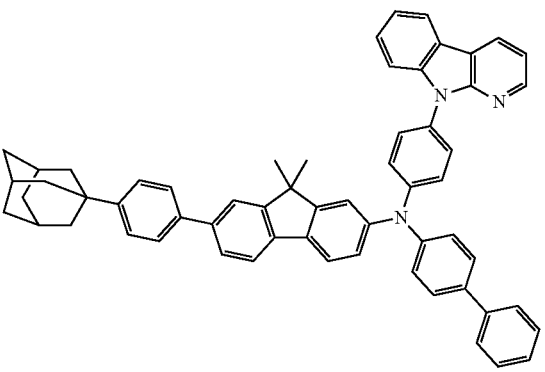
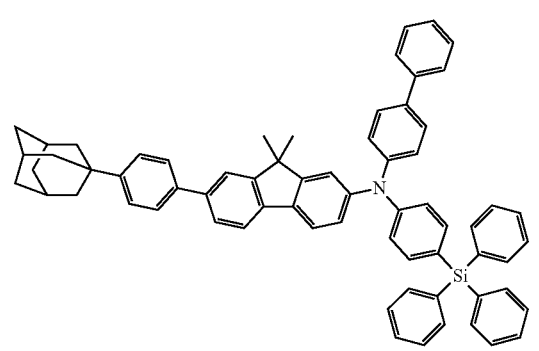
36
-continued
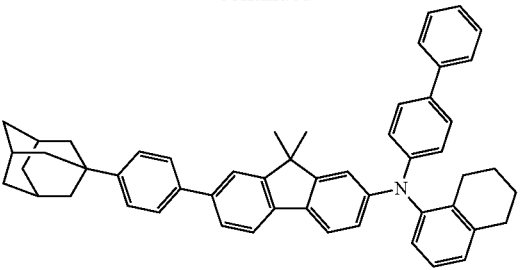
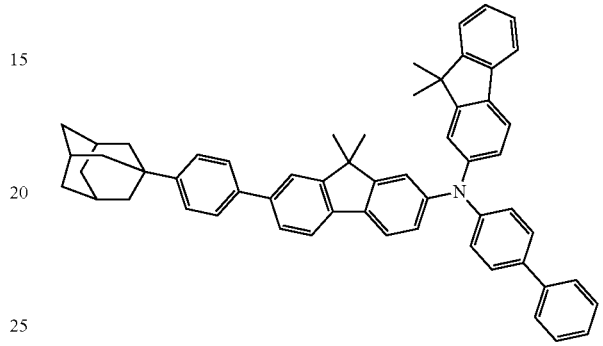
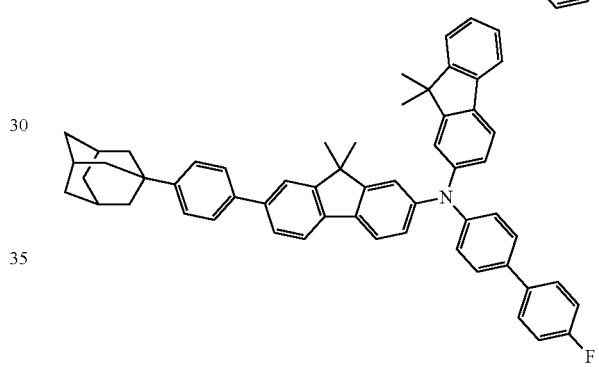
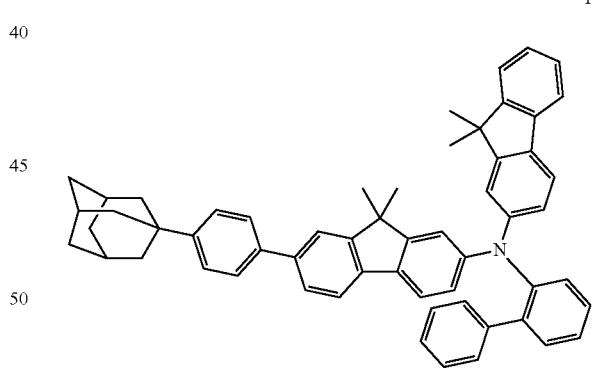
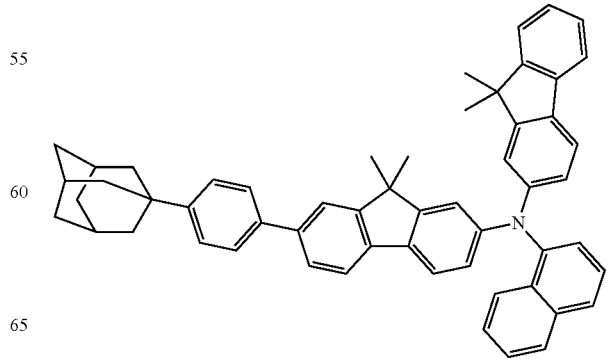

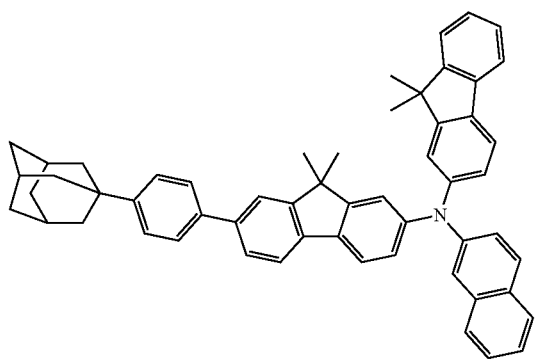
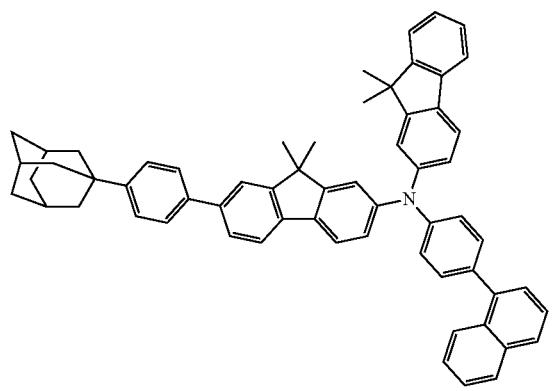
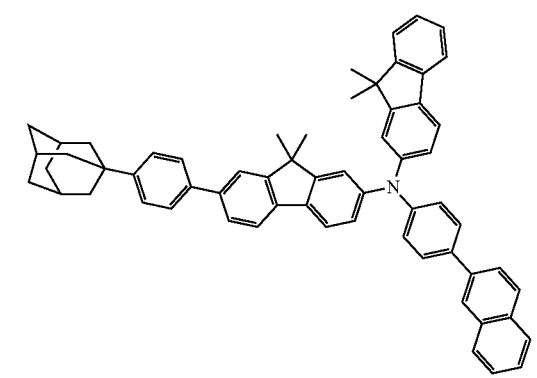
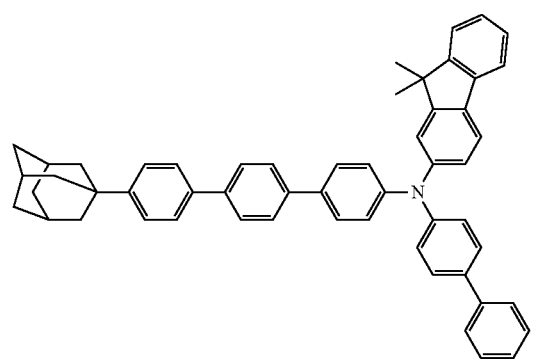
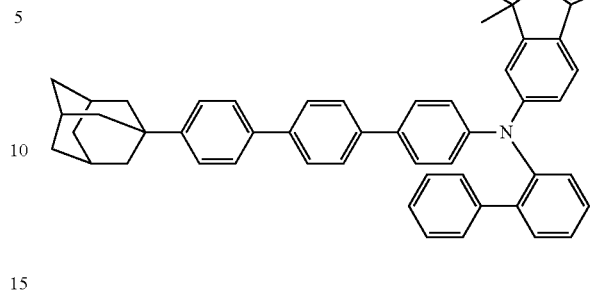
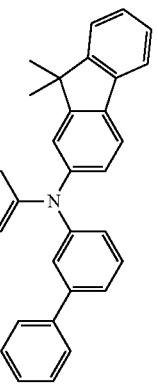
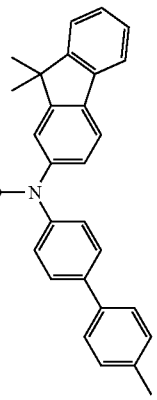
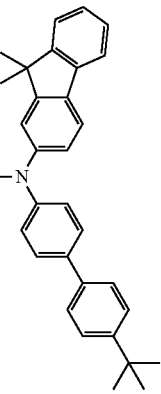

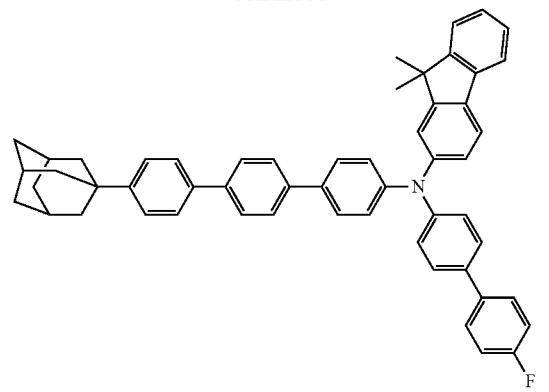
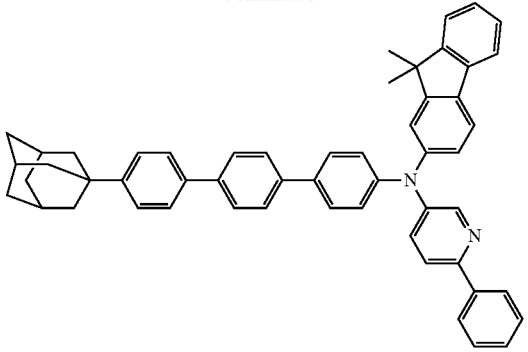
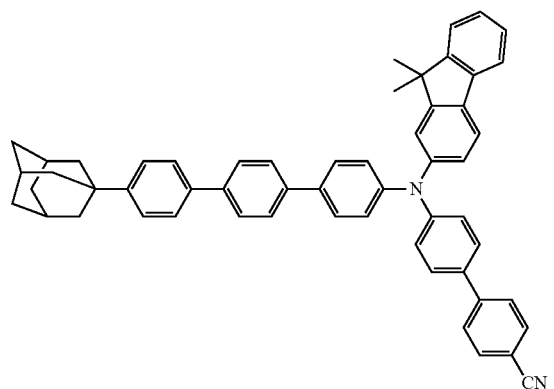
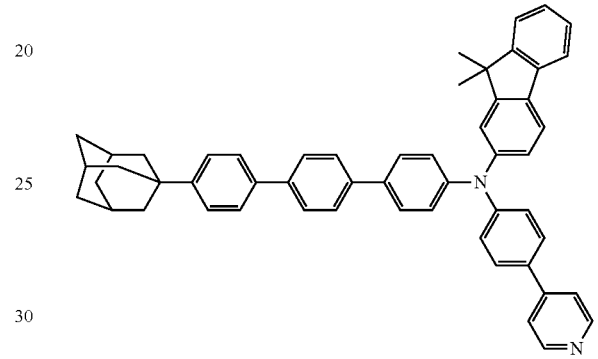
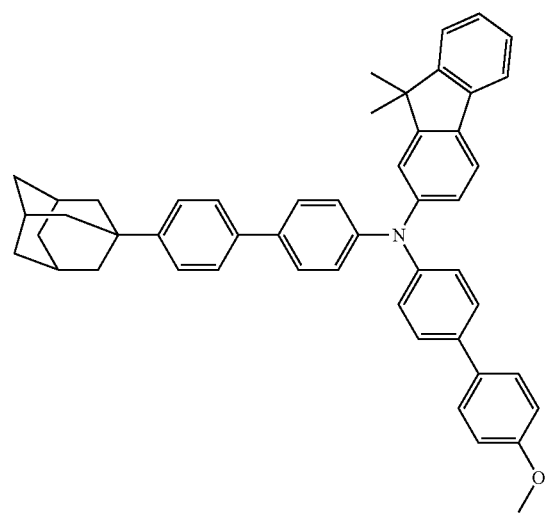
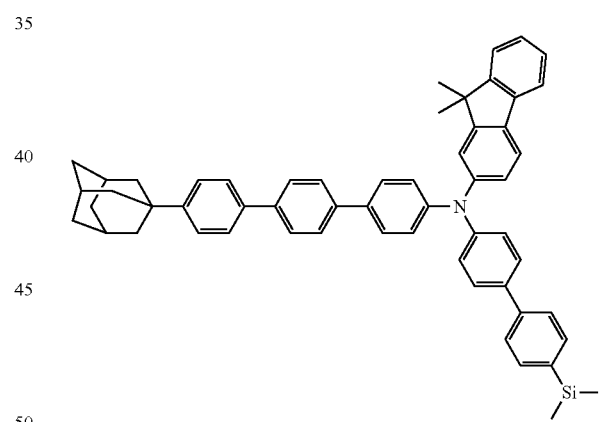
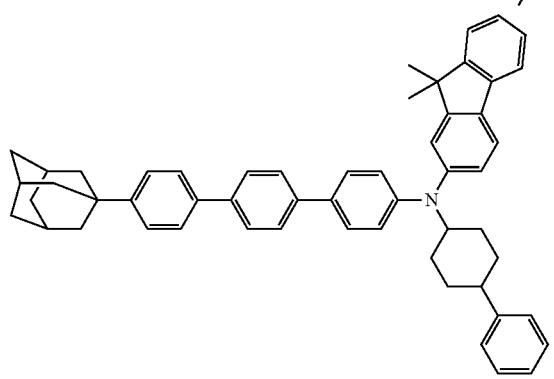
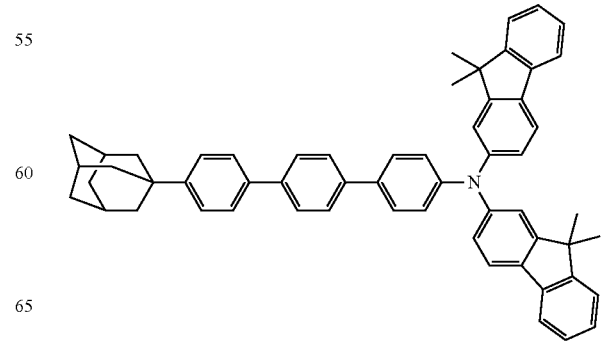

41
-continued
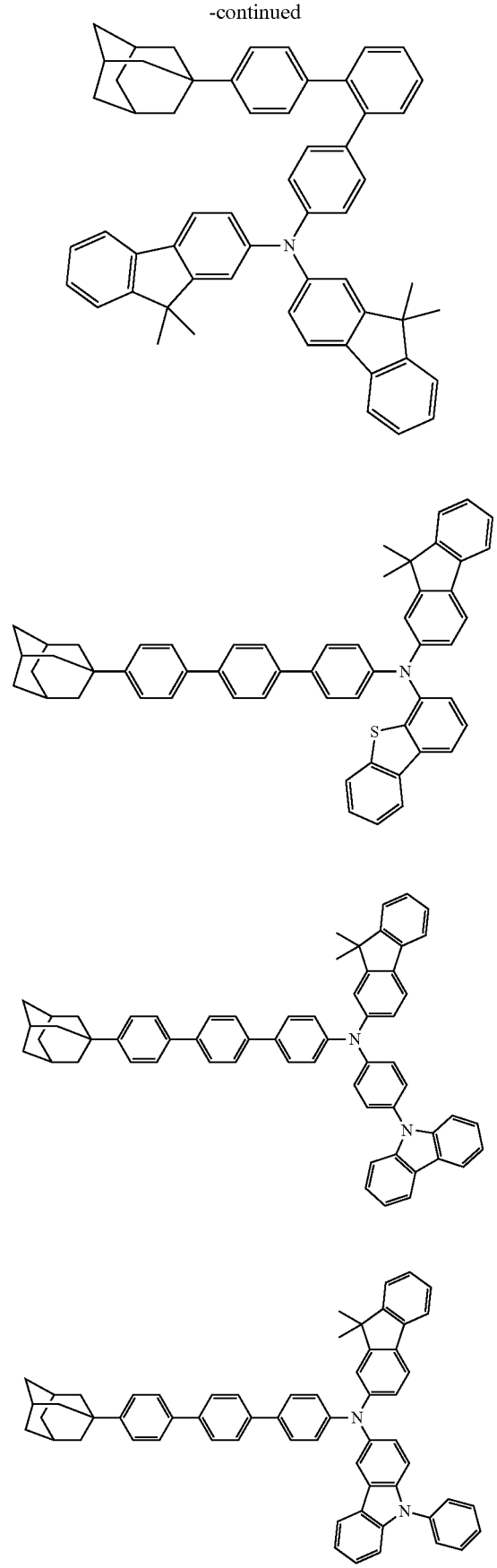
42
-continued
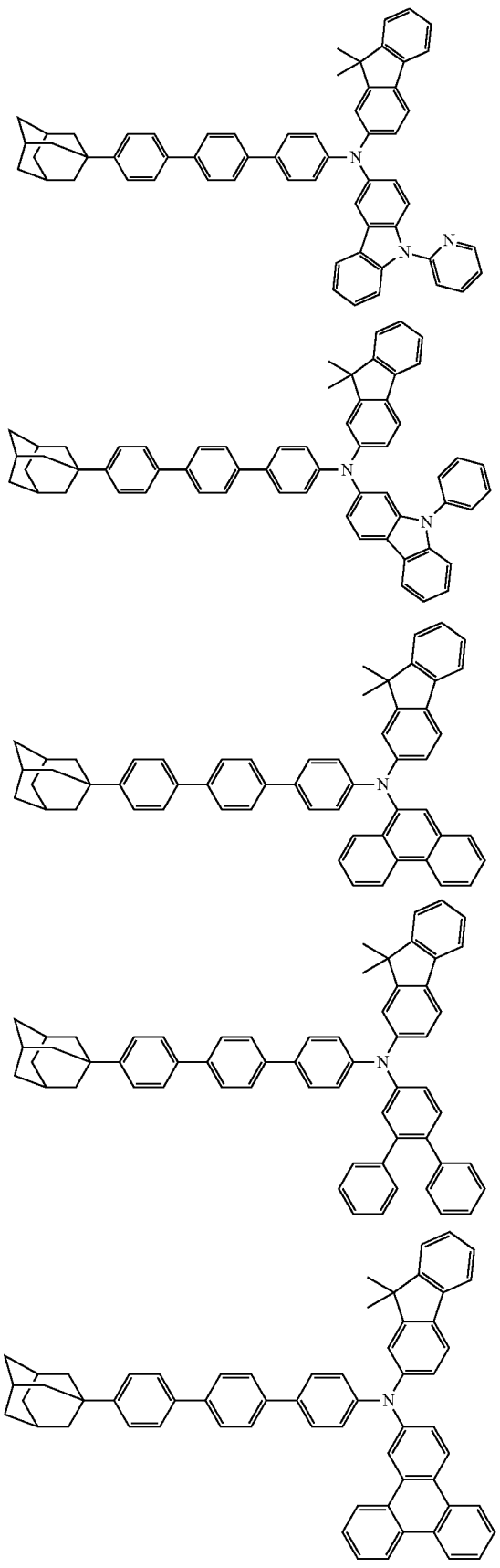

-continued
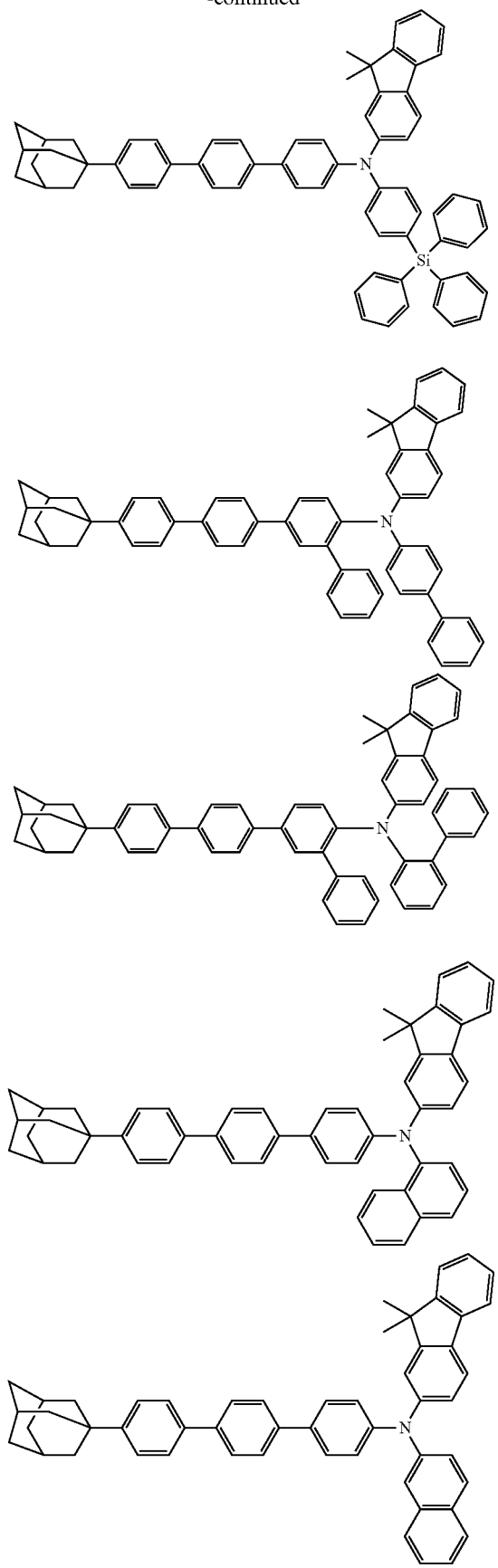
-continued
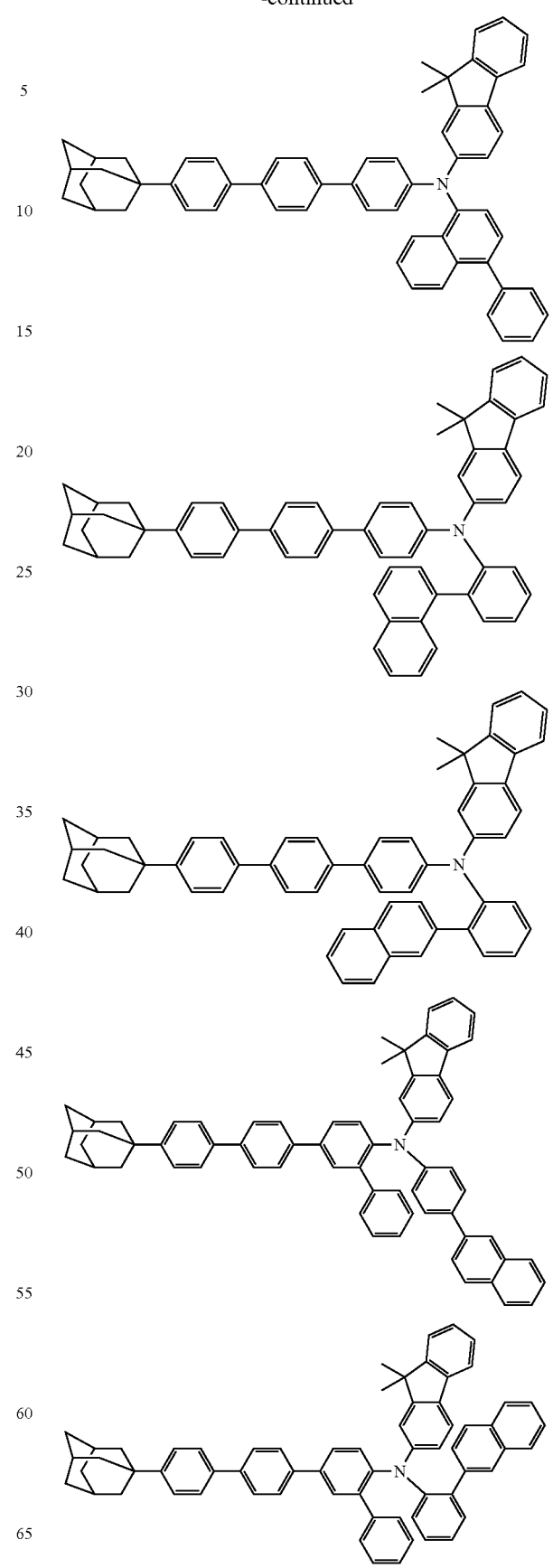

-continued
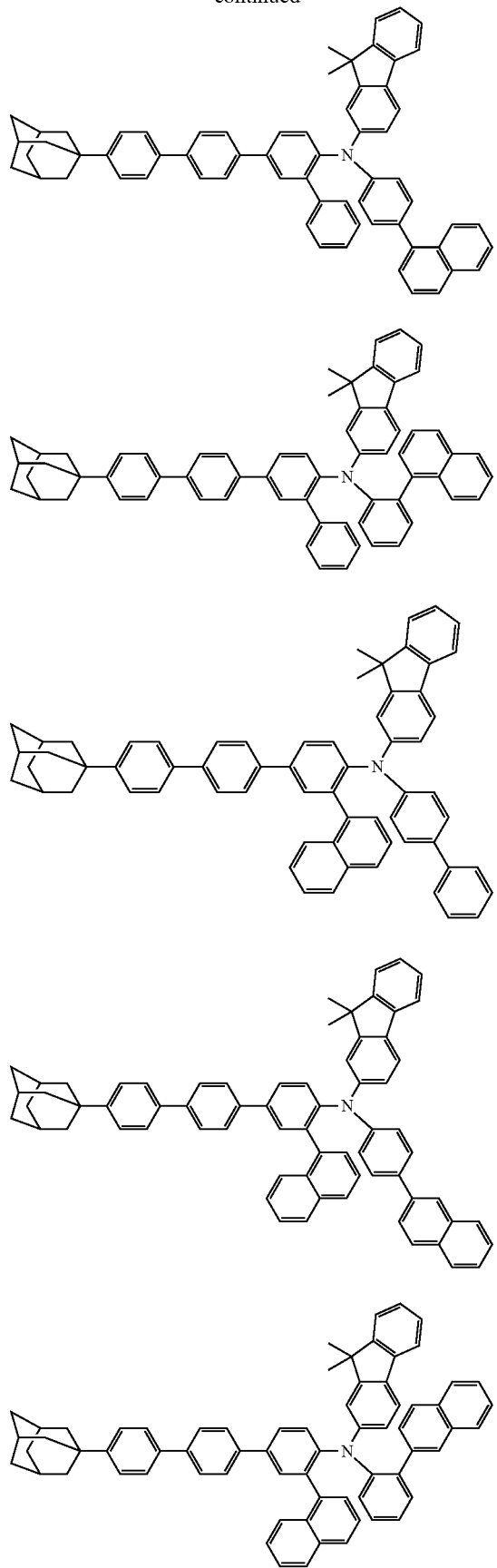
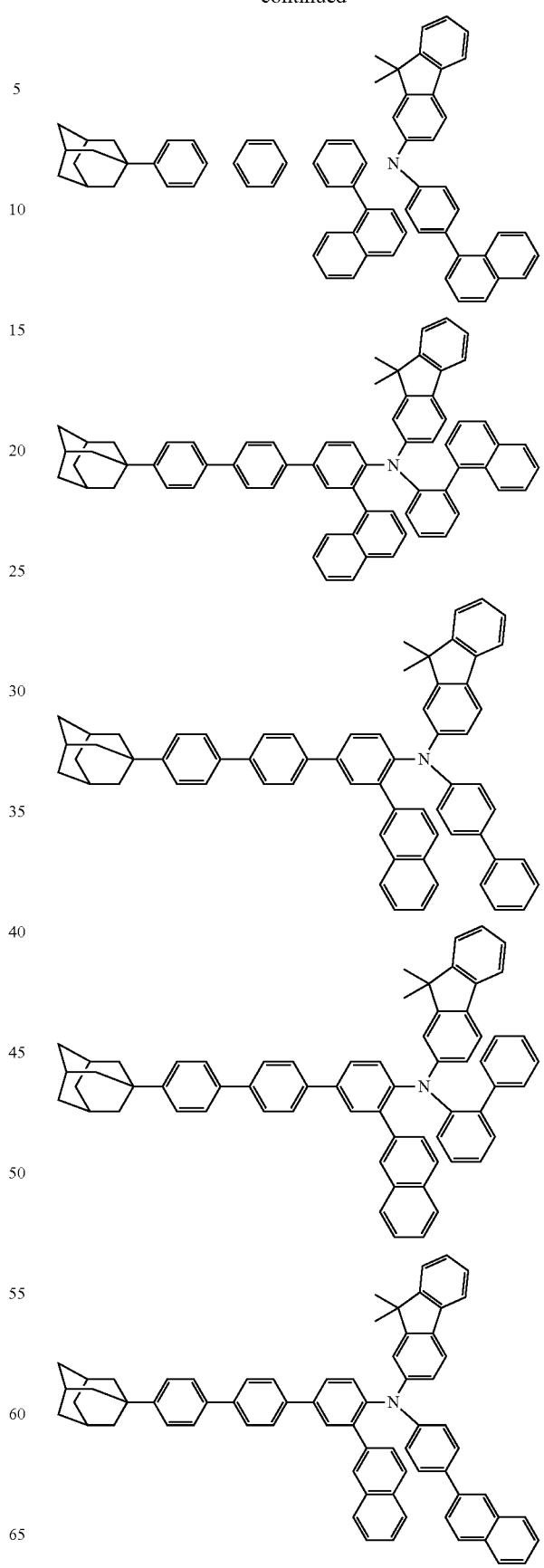

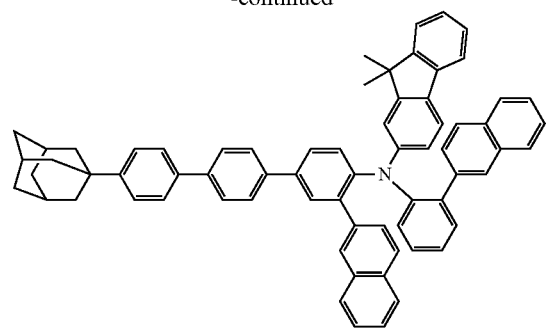
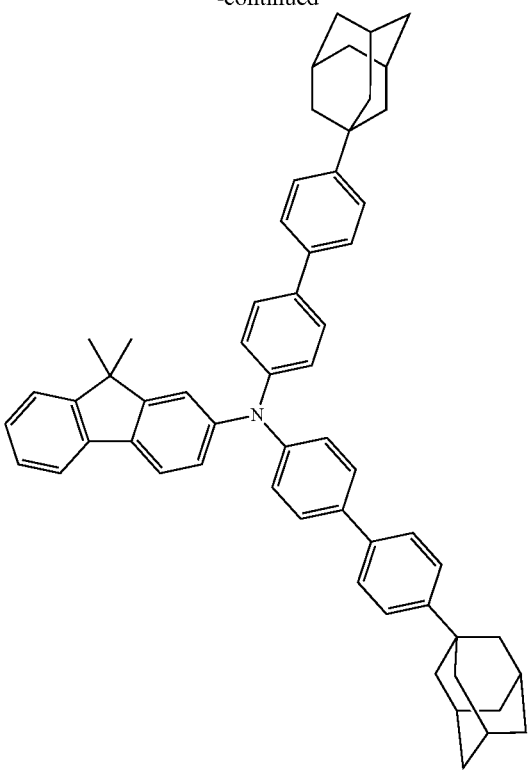
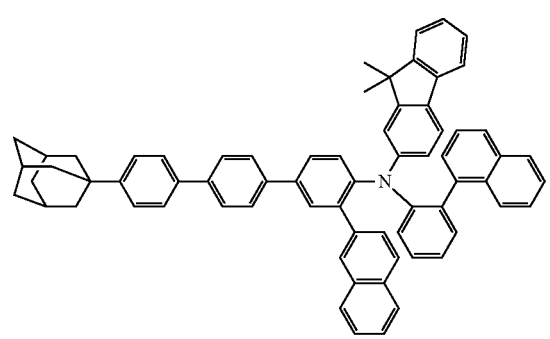
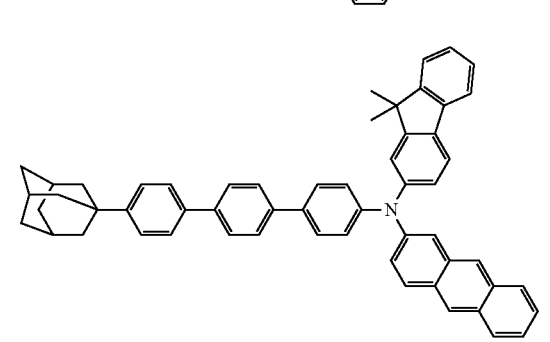
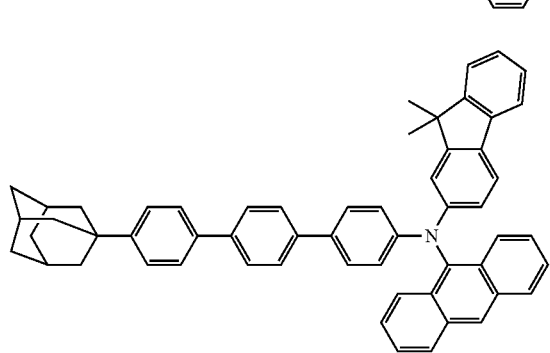
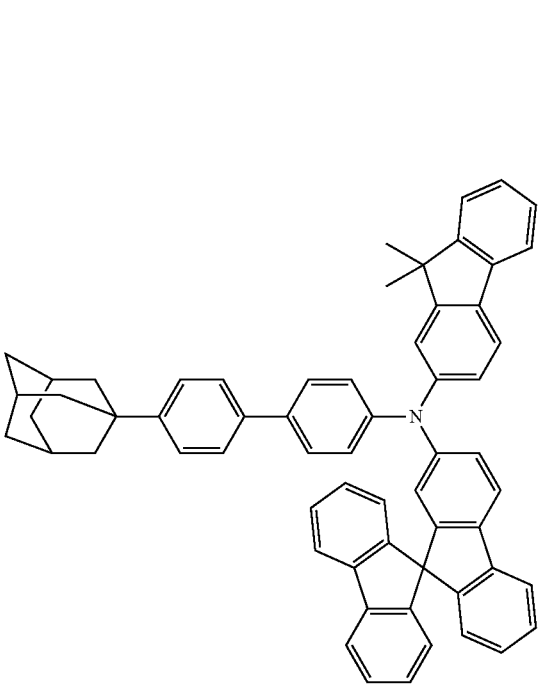

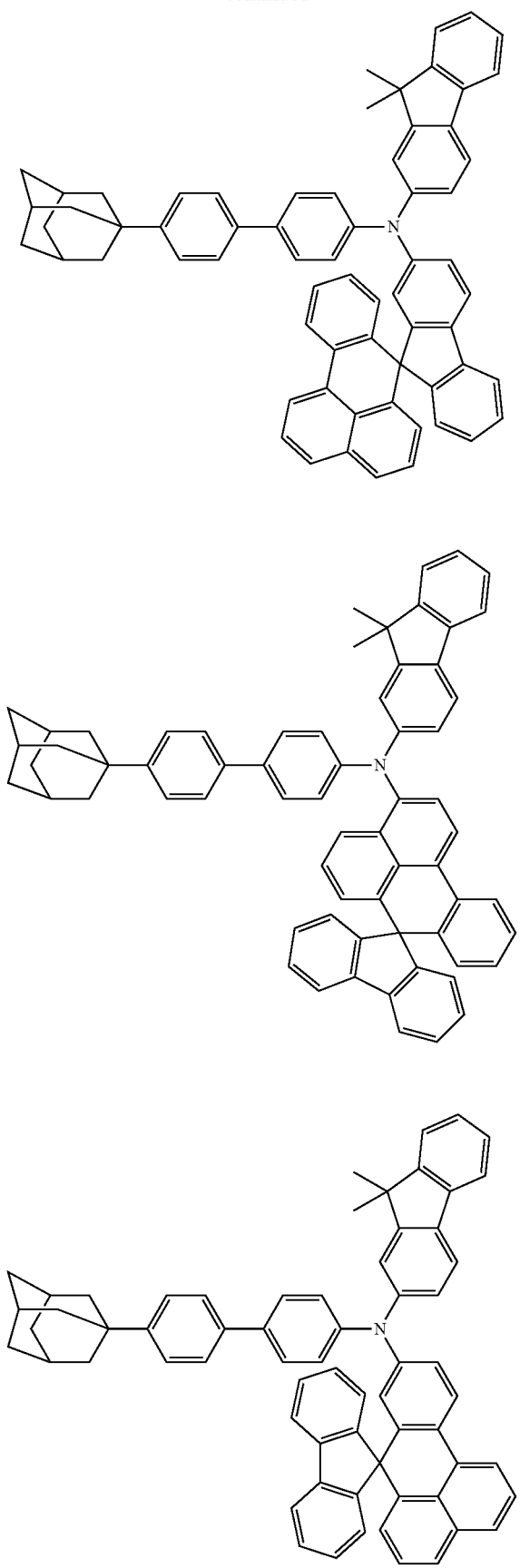 [SMILES: CC1(C)c2ccccc2-c2ccc(N(c3ccc(-c4ccc(C56CC7CC(CC(C7)C5)C6)cc4)cc3)c3ccc4c(c3)C3(c5ccccc5-4)c4ccccc4-c4cccc5cccc3c45)cc21 ; CC1(C)c2ccccc2-c2ccc(N(c3ccc(-c4ccc(C56CC7CC(CC(C7)C5)C6)cc4)cc3)c3ccc4c5c(cccc35)C3(c5ccccc5-c5ccccc53)c3ccccc3-4)cc21 ; CC1(C)c2ccccc2-c2ccc(N(c3ccc(-c4ccc(C56CC7CC(CC(C7)C5)C6)cc4)cc3)c3ccc4c(c3)C3(c5ccccc5-c5ccccc53)c3cccc5cccc-4c35)cc21]
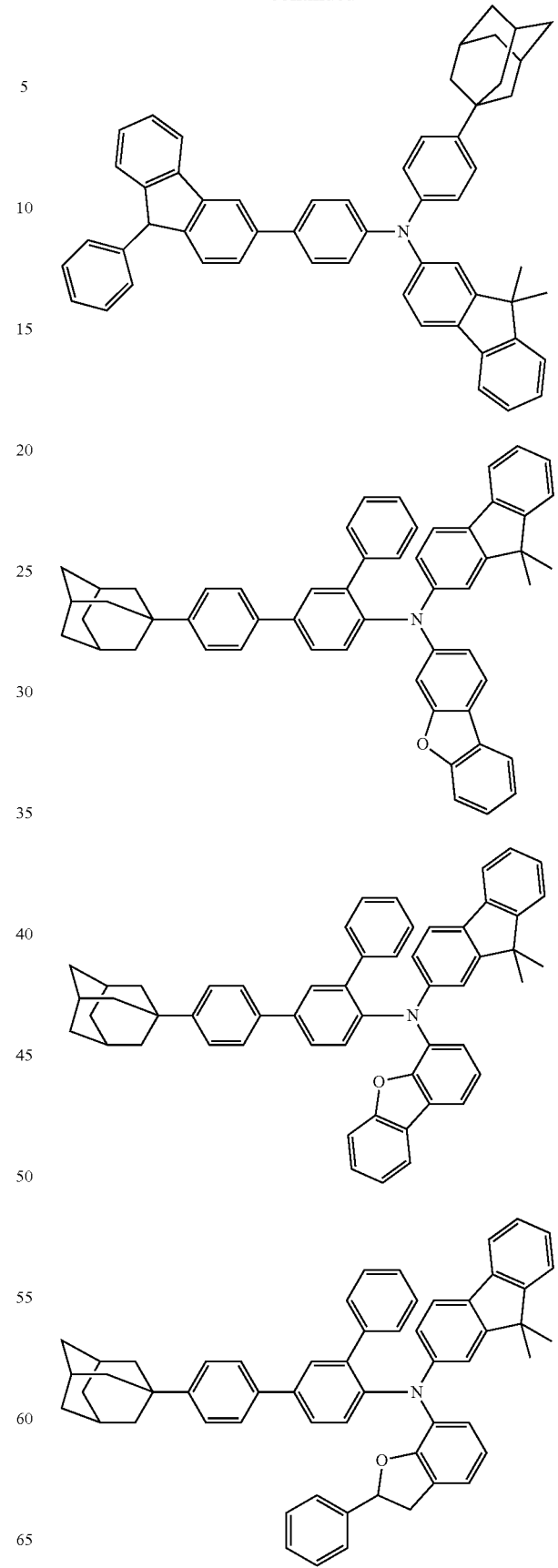

In addition, as an example of the present invention, methods for preparing the compound represented by Formula 1 may be provided with reference to Reaction Schemes 1 to 4 below.

[Reaction Scheme 1]

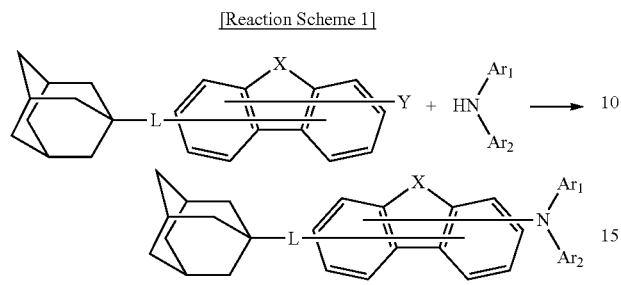

[Reaction Scheme 2]

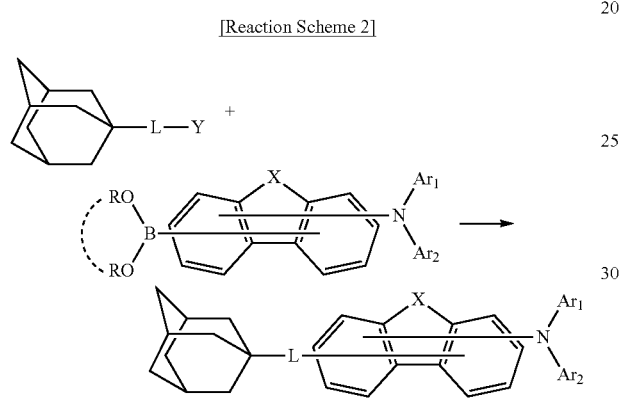

[Reaction Scheme 3]

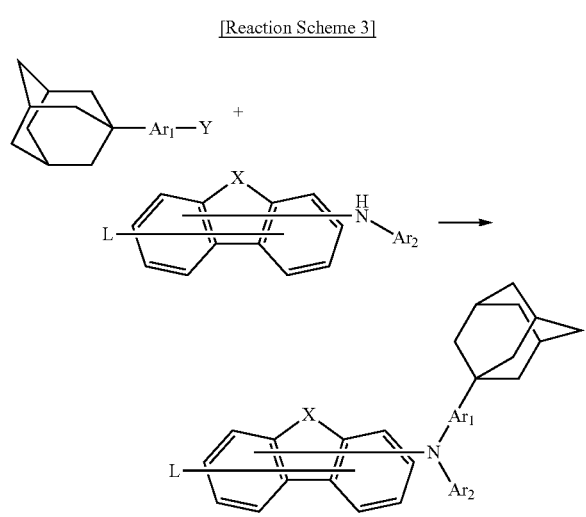

[Reaction Scheme 4]

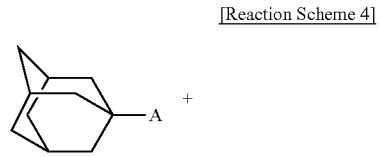

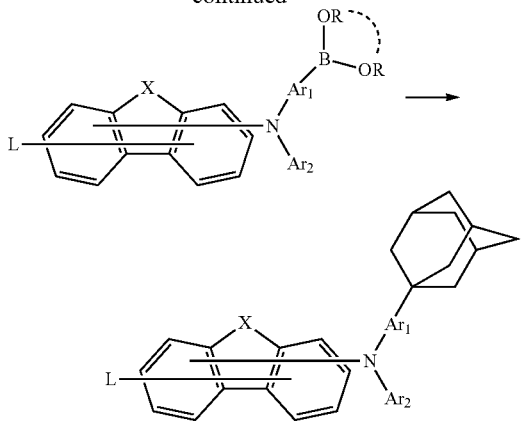

In Reaction Schemes 1 and 3, Y is a substituent capable of being reacted with a nitrogen through amination, for example, —F, —Br, —Cl, —I or —OTf, and preferably selected from the group consisting of —Cl, —Br, —I and —OTf. In Reaction Schemes 2 and 4, X is a substituent capable of having a reaction by Suzuki coupling, for example, —F, —Br, —Cl, —I or —OTf, and preferably selected from —Cl, —Br, —I, or —OTf, and

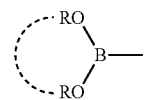

is a boron compound, wherein R is hydrogen or an alkyl group and may be bonded to each other, forming a ring, or may not be bonded.

The present invention provides an OLED including the compound represented by Formula 1.

According to an exemplary embodiment of the present invention, the OLED includes a first electrode; a second electrode placed opposite to the first electrode; and one or more organic material layers placed between the first electrode and the second electrode, and at least one of the one or more organic material layers may include the compound represented by Formula 1.

In the OLED of the present invention, the organic material layer may have a monolayer structure, or a multilayer structure formed by laminating two or more organic material layers. For example, the OLED of the present invention may have a structure including, as organic material layers, a HIL, a HTL, an EBL, an EML, a HBL, an ETL, an EIL, etc. However, the structure of the OLED is not limited thereto, and thus may include a smaller number of organic layers.

Specifically, the HIL, HTL and/or EBL may include the compound represented by Formula 1 according to the present invention, preferably, the Compounds 1 to 166 of Formula 1 according to the present invention, either alone or in combination of two or more thereof. When the adamantane derivative compound of the present invention, preferably, any one or more of the compounds 1 to 166, is/are used as hole injection, hole transport and/or electron blocking materials, the compound(s) may be added at 0.01 to 100 wt %, for example, 0.01 to 20 wt %, 20 to 80 wt %, 80 to 100 wt % with respect to the HIL, HTL and/or EBL.

Meanwhile, the OLED of the present invention may be manufactured by forming organic material layers and electrodes using materials and methods known in the art, except that one or more of the organic material layers should include the compound represented by Formula 1.

Each layer constituting the OLED may be formed by any conventional method of dry film-forming methods, such as vacuum deposition, sputtering, plasma deposition and ion plating, or wet film-forming methods, such as spin coating, dip coating and flow coating. A film thickness is not particularly limited. However, when the film thickness is too large, a high applied voltage is required to obtain a certain light output, thereby degrading efficiency, and when the film thickness is too small, it is difficult to obtain a sufficient luminance even by applying an electric field due to generation of pin holes or the like. Generally, a film thickness is preferably 5 nm to 10 μm, and more preferably is 50 nm to 400 nm.

EXAMPLES

Hereinafter, the present invention will be described in further detail with reference to examples. These examples are merely provided to illustrate the present invention, and it should not be construed that the scope of the present invention is limited by the following examples.

Synthesis Example 1: Preparation of Compound 1

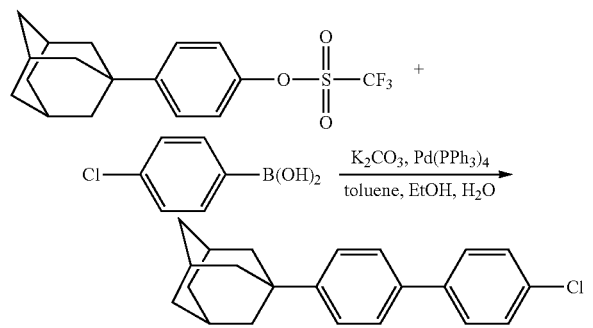

54.1 g (0.15 mol) of 4-(adamantane-1-yl)phenyl trifluoromethanesulfonate and 28.1 g (0.18 mol) of (4-chlorophenyl)boronic acid were dissolved in 800 ml of toluene, and 200 ml of ethanol, 200 ml of water, 62.2 g (0.45 mol) of potassium carbonate, and 5.2 g (4.5 mmol) of tetrakis(triphenylphosphine)palladium(0) were added thereto, followed by refluxing for 12 hours. After the reaction was completed, the resulting solution was cooled to room temperature, and then an organic layer was extracted using 500 ml of dichloromethane and 300 ml of H₂O. Following dehydration of the organic layer with MgSO₄, the remaining solution was distilled, subjected to column chromatography using dichloromethane, and then recrystallized using n-hexane/dichloromethane, thereby obtaining 41.2 g of 1-(4'-chloro-[1,1'-biphenyl]-4-yl)adamantane with a yield of 85%.

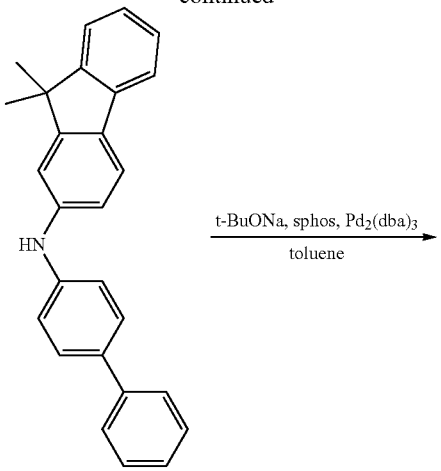

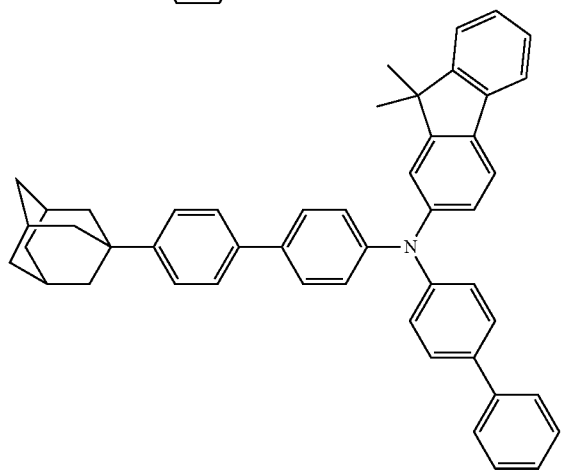

5.42 g (15.0 mmol) of N-([1,1'-biphenyl]-4-yl)-9,9-dimethyl-9H-fluorene-2-amine and 5.33 g (16.5 mmol) of 1-(4'-chloro-[1,1'-biphenyl]-4-yl)adamantane were dissolved in 100 ml of toluene, and 4.32 g (45.0 mmol) of sodium tert-butoxide, 246 mg (0.60 mmol) of 2-dicyclohexylphosphino-2',6''-dimethoxybiphenyl and 275 mg (0.30 mmol) of tris(dibenzylideneacetone)dipalladium(0) were added thereto, followed by refluxing for 12 hours. After the reaction was completed, the resulting solution was cooled to room temperature, and then an organic layer was extracted using 100 ml of dichloromethane and 50 ml of H₂O. Following dehydration of the organic layer with MgSO₄, the remaining solution was distilled and subjected to and column chromatography using n-hexane/dichloromethane, thereby obtaining 1.9 g of Compound 1 with a yield of 20%.

Synthesis Example 2: Preparation of Compound 110

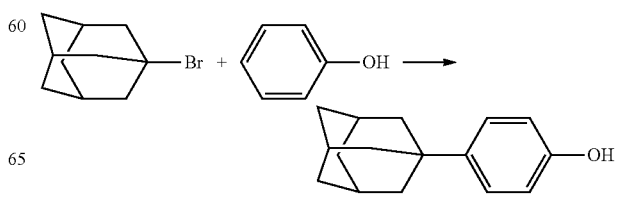

108 g (0.50 mol) of 1-bromoadamantane was added to 188 g (2.0 mol) of phenol, and heated at 120° C. for 12 hours. After the reaction was completed, the resulting solution was cooled to room temperature and stirred in a beaker containing 2 L of hot water, thereby forming a precipitate. After filtering, the precipitate was washed three times with hot water and sufficiently vacuum-dried, thereby obtaining 91.3 g of 4-(adamantane-1-yl)phenol with a yield of 80%.

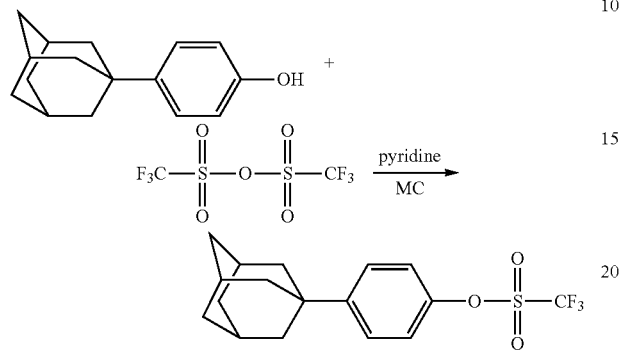

91 g (0.40 mol) of 4-(adamantane-1-yl)phenol and 63 g (0.80 mol) of pyridine were dissolved in 500 ml of dichloromethane and cooled to 0° C., and then 135 g (0.48 mol) of trifluoromethanesulfonic anhydride was slowly added. After the reaction was completed with stirring for 3 hours, 1 N hydrochloric acid and 300 ml of water were sequentially added to the resulting solution for extraction. Following dehydration of the organic layer with MgSO$_4$, the remaining solution was distilled and subjected to column chromatography using n-hexane/dichloromethane, thereby obtaining 122 g of 4-(adamantane-1-yl)phenyl trifluoromethanesulfonate with a yield of 85%.

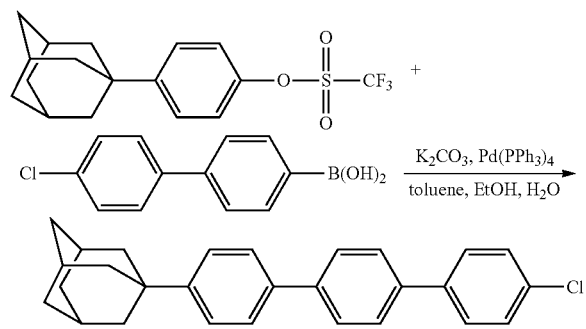

54.1 g (0.15 mol) of 4-(adamantane-1-yl)phenyl trifluoromethanesulfonate and 41.8 g (0.18 mol) of (4'-chloro-[1,1'-biphenyl]-4-yl)boronic acid were dissolved in 800 ml of toluene, and 200 ml of ethanol, 200 ml of water, 62.2 g (0.45 mol) of potassium carbonate and 5.2 g (4.5 mmol) of tetrakis(triphenylphosphine)palladium(0) were added thereto, followed by refluxing for 12 hours. After the reaction was completed, the resulting solution was cooled to room temperature, and then an organic layer was extracted using 500 ml of dichloromethane and 300 ml of H$_2$O. Following dehydration of the organic layer with MgSO$_4$, the remaining solution was distilled, subjected to column chromatography using dichloromethane, and then recrystallized using n-hexane/dichloromethane, thereby obtaining 53.5 g of 1-(4"-chloro-[1,1':4',1"-terphenyl]-4-yl)adamantane with a yield of 90%.

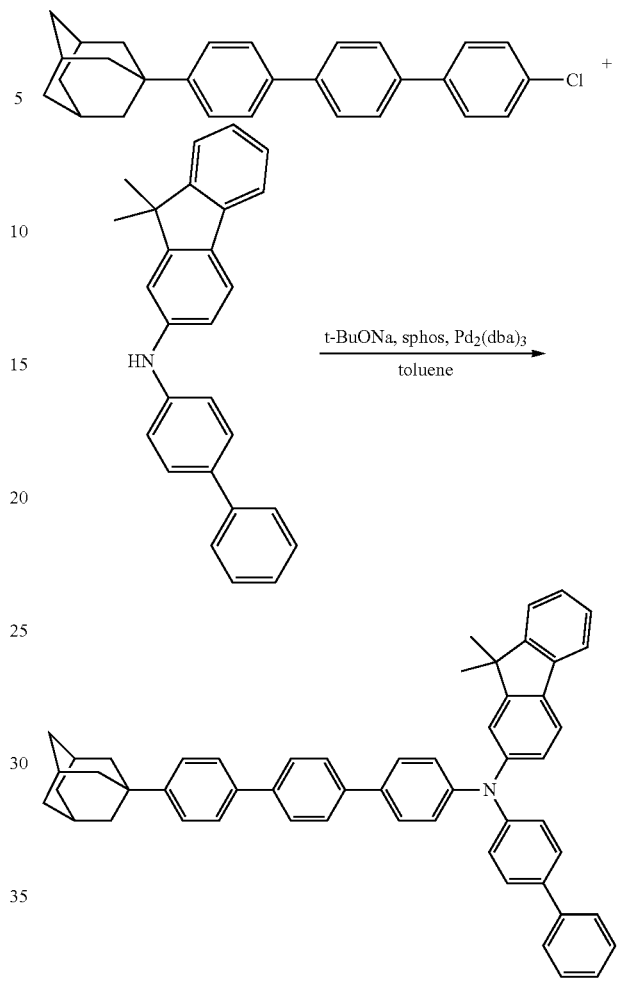

5.42 g (15.0 mmol) of N-([1,1'-biphenyl]-4-yl)-9,9-dimethyl-9H-fluorene-2-amine and 6.58 g (16.5 mmol) of 1-(4"-chloro-[1,1':4',1"-terphenyl]-4-yl)adamantane were dissolved in 100 ml of toluene, and 4.32 g (45.0 mmol) of sodium tert-butoxide, 246 mg (0.60 mmol) of 2-dicyclohexylphosphino-2',6"-dimethoxybiphenyl and 275 mg (0.30 mmol) of tris(dibenzylideneacetone)dipalladium(0) were added thereto, followed by refluxing for 12 hours. After the reaction was completed, the resulting solution was cooled to room temperature, and then an organic layer was extracted using 100 ml of dichloromethane and 50 ml of H$_2$O. Following dehydration of the organic layer with MgSO$_4$, the remaining solution was distilled and subjected to column chromatography using n-hexane/dichloromethane, thereby obtaining 1.7 g of Compound 110 with a yield of 16%.

Synthesis Example 3: Preparation of Compound 6

Compound 6 was prepared by the same method as described in Synthesis Example 1, except that 5.42 g (15.0 mmol) of N-([1,1'-biphenyl]-2-yl)-9,9-dimethyl-9H-fluorene-2-amine and 5.33 g (16.5 mmol) of 1-(4'-chloro-[1,1'-biphenyl]-4-yl)adamantane were used.

Synthesis Example 4: Preparation of Compound 18

Compound 18 was prepared by the same method as described in Synthesis Example 1, except that 5.63 g (15.0 mmol) of N-(9,9-dimethyl-9H-fluorene-2-yl)dibenzo[b,d]furan-3-amine and 5.33 g (16.5 mmol) of 1-(4'-chloro-[1,1'-biphenyl]-4-yl)adamantane were used.

Synthesis Example 5: Preparation of Compound 27

Compound 27 was prepared by the same method as described in Synthesis Example 1, except that 6.02 g (15.0 mmol) of bis(9,9-dimethyl-9H-fluorene-2-yl)amine and 5.95 g (16.5 mmol) of 4-(adamantane-1-yl)phenyl trifluoromethanesulfonate were used.

Synthesis Example 6: Preparation of Compound 29

Compound 29 was prepared by the same method as described in Synthesis Example 1, except that 6.02 g (15.0 mmol) of bis(9,9-dimethyl-9H-fluorene-2-yl)amine and 5.33 g (16.5 mmol) of 1-(3'-chloro-[1,1'-biphenyl]-4-yl)adamantane were used.

Synthesis Example 7: Preparation of Compound 30

Compound 30 was prepared by the same method as described in Synthesis Example 1, except that 6.02 g (15.0 mmol) of bis(9,9-dimethyl-9H-fluorene-2-yl)amine and 5.33 g (16.5 mmol) of 1-(4'-chloro-[1,1'-biphenyl]-4-yl)adamantane were used.

Synthesis Example 8: Preparation of Compound 31

Compound 31 was prepared by the same method as described in Synthesis Example 1, except that 6.02 g (15.0 mmol) of bis(9,9-dimethyl-9H-fluorene-2-yl)amine and 5.33 g (16.5 mmol) of 1-(2'-chloro-[1,1'-biphenyl]-4-yl)adamantane were used.

Synthesis Example 9: Preparation of Compound 32

Compound 32 was prepared by the same method as described in Synthesis Example 1, except that 6.17 g (15.0 mmol) of 9,9-diphenyl-N-(4-(naphthalen-1-yl)phenyl)-9H-fluorene-2-amine and 5.33 g (16.5 mmol) of 1-(4'-chloro-[1,1'-biphenyl]-4-yl)adamantane were used.

Synthesis Example 10: Preparation of Compound 33

Compound 33 was prepared by the same method as described in Synthesis Example 1, except that 6.17 g (15.0 mmol) of 9,9-diphenyl-N-(4-(naphthalen-2-yl)phenyl)-9H-fluorene-2-amine and 5.33 g (16.5 mmol) of 1-(4'-chloro-[1,1'-biphenyl]-4-yl)adamantane were used.

Synthesis Example 11: Preparation of Compound 34

Compound 34 was prepared by the same method as described in Synthesis Example 1, except that 6.17 g (15.0 mmol) of 9,9-dimethyl-N-(2-(naphthalen-2-yl)phenyl)-9H-fluorene-2-amine and 5.33 g (16.5 mmol) of 1-(4'-chloro-[1,1'-biphenyl]-4-yl)adamantane were used.

Synthesis Example 12: Preparation of Compound 35

Compound 35 was prepared by the same method as described in Synthesis Example 1, except that 5.03 g (15.0 mmol) of 9,9-dimethyl-N-(naphthalen-1-yl)-9H-fluorene-2-amine and 5.33 g (16.5 mmol) of 1-(4'-chloro-[1,1'-biphenyl]-4-yl)adamantane were used.

Synthesis Example 13: Preparation of Compound 36

Compound 36 was prepared by the same method as described in Synthesis Example 1, except that 5.03 g (15.0 mmol) of 9,9-dimethyl-N-(naphthalen-2-yl)-9H-fluorene-2-amine and 5.33 g (16.5 mmol) of 1-(4'-chloro-[1,1'-biphenyl]-4-yl)adamantane were used.

Synthesis Example 14: Preparation of Compound 37

Compound 37 was prepared by the same method as described in Synthesis Example 1, except that 6.17 g (15.0 mmol) of 9,9-dimethyl-N-(2-(naphthalen-1-yl)phenyl)-9H-fluorene-2-amine and 5.95 g (16.5 mmol) of 4-(adamantane-1-yl)phenyl trifluoromethanesulfonate were used.

Synthesis Example 15: Preparation of Compound 38

Compound 38 was prepared by the same method as described in Synthesis Example 1, except that 6.17 g (15.0 mmol) of 9,9-dimethyl-N-(2-(naphthalen-1-yl)phenyl)-9H-fluorene-2-amine and 5.33 g (16.5 mmol) of 1-(4'-chloro-[1,1'-biphenyl]-4-yl)adamantane were used.

Synthesis Example 16: Preparation of Compound 39

Compound 39 was prepared by the same method as described in Synthesis Example 1, except that 6.17 g (15.0 mmol) of 9,9-dimethyl-N-(4-phenylnaphthalen-1-yl)-9H-fluorene-2-amine and 5.33 g (16.5 mmol) of 1-(4'-chloro-[1,1'-biphenyl]-4-yl)adamantane were used.

Synthesis Example 17: Preparation of Compound 40

Compound 40 was prepared by the same method as described in Synthesis Example 1, except that 6.17 g (15.0 mmol) of 9,9-dimethyl-N-(4-phenylnaphthalen-1-yl)-9H-fluorene-2-amine and 5.95 g (16.5 mmol) of 4-(adamantane-1-yl)phenyl trifluoromethanesulfonate were used.

Synthesis Example 18: Preparation of Compound 57

Compound 57 was prepared by the same method as described in Synthesis Example 1, except that 5.78 g (15.0 mmol) of N-(9,9-dimethyl-9H-fluorene-2-yl)phenanthrene-9-amine and 5.95 g (16.5 mmol) of 4-(adamantane-1-yl)phenyl trifluoromethanesulfonate were used.

Synthesis Example 19: Preparation of Compound 58

Compound 58 was prepared by the same method as described in Synthesis Example 1, except that 5.78 g (15.0 mmol) of N-(9,9-dimethyl-9H-fluorene-2-yl)phenanthrene-9-amine and 5.33 g (16.5 mmol) of 1-(4'-chloro-[1,1'-biphenyl]-4-yl)adamantane were used.

Synthesis Example 20: Preparation of Compound 60

Compound 60 was prepared by the same method as described in Synthesis Example 1, except that 6.56 g (15.0 mmol) of N-([1,1':3',1"-terphenyl]-4'-yl)-9,9-dimethyl-9H-fluorene-2-amine and 5.95 g (16.5 mmol) of 4-(adamantane-1-yl)phenyl trifluoromethanesulfonate were used.

Synthesis Example 21: Preparation of Compound 61

Compound 61 was prepared by the same method as described in Synthesis Example 1, except that 6.56 g (15.0 mmol) of N-([1,1':3',1"-terphenyl]-4'-yl)-9,9-dimethyl-9H-fluorene-2-amine and 5.33 g (16.5 mmol) of 1-(4'-chloro-[1,1'-biphenyl]-4-yl)adamantane were used.

Synthesis Example 22: Preparation of Compound 62

Compound 62 was prepared by the same method as described in Synthesis Example 1, except that 7.71 g (15.0 mmol) of 9,9-dimethyl-N-(5'-phenyl-[1,1':3',1"-terphenyl]-4'-yl)-9H-fluorene-2-amine and 5.33 g (16.5 mmol) of 1-(4'-chloro-[1,1'-biphenyl]-4-yl)adamantane were used.

Synthesis Example 23: Preparation of Compound 64

Compound 64 was prepared by the same method as described in Synthesis Example 1, except that 5.69 g (15.0 mmol) of 4-(adamantane-1-yl)-[1,1':3',1"-terphenyl]-4'-amine and 9.01 g (33.0 mmol) of 2-bromo-9,9-dimethyl-9H-fluorene were used.

Synthesis Example 24: Preparation of Compound 67

Compound 67 was prepared by the same method as described in Synthesis Example 1, except that 4.82 g (15.0 mmol) of di([1,1'-biphenyl]-4-yl)amine and 7.98 g (16.5 mmol) of 1-(4-(7-bromo-9,9-dimethyl-9H-fluoren-2-yl)phenyl)adamantane were used.

Synthesis Example 25: Preparation of Compound 68

Compound 68 was prepared by the same method as described in Synthesis Example 1, except that 5.42 g (15.0 mmol) of N-([1,1'-biphenyl]-2-yl)-9,9-dimethyl-9H-fluorene-2-amine and 7.98 g (16.5 mmol) of 1-(4-(7-bromo-9,9-dimethyl-9H-fluoren-2-yl)phenyl)adamantane were used.

Synthesis Example 26: Preparation of Compound 111

Compound 111 was prepared by the same method as described in Synthesis Example 1, except that 5.42 g (15.0 mmol) of N-([1,1'-biphenyl]-2-yl)-9,9-dimethyl-9H-fluorene-2-amine and 6.58 g (16.5 mmol) of 1-(4"-chloro-[1,1':4',1"-terphenyl]-4-yl)adamantane were used.

Synthesis Example 27: Preparation of Compound 122

Compound 122 was prepared by the same method as described in Synthesis Example 1, except that 6.02 g (15.0 mmol) of bis(9,9-dimethyl-9H-fluoren-2-yl)amine and 6.58 g (16.5 mmol) of 1-(4"-chloro-[1,1':4',1"-terphenyl]-4-yl)adamantane were used.

Synthesis Example 28: Preparation of Compound 129

Compound 129 was prepared by the same method as described in Synthesis Example 1, except that 5.78 g (15.0 mmol) of N-(9,9-dimethyl-9H-fluoren-2-yl)phenanthrene-9-amine and 6.58 g (16.5 mmol) of 1-(4"-chloro-[1,1':4',1"-terphenyl]-4-yl)adamantane were used.

Synthesis Example 29: Preparation of Compound 135

Compound 135 was prepared by the same method as described in Synthesis Example 1, except that 5.03 g (15.0 mmol) of 9,9-dimethyl-N-(naphthalen-1-yl)-9H-fluorene-2-amine and 6.58 g (16.5 mmol) of 1-(4"-chloro-[1,1':4',1"-terphenyl]-4-yl)adamantane were used.

Synthesis Example 30: Preparation of Compound 136

Compound 136 was prepared by the same method as described in Synthesis Example 1, except that 5.03 g (15.0 mmol) of 9,9-dimethyl-N-(naphthalen-2-yl)-9H-fluorene-2-amine and 6.58 g (16.5 mmol) of 1-(4"-chloro-[1,1':4',1"-terphenyl]-4-yl)adamantane were used.

Synthesis Example 31: Preparation of Compound 137

Compound 137 was prepared by the same method as described in Synthesis Example 1, except that 6.17 g (15.0 mmol) of 9,9-dimethyl-N-(4-phenylnaphthalen-1-yl)-9H-fluorene-2-amine and 6.58 g (16.5 mmol) of 1-(4"-chloro-[1,1':4',1"-terphenyl]-4-yl)adamantane were used.

Synthesis Example 32: Preparation of Compound 138

Compound 138 was prepared by the same method as described in Synthesis Example 1, except that 6.17 g (15.0 mmol) of 9,9-dimethyl-N-(2-(naphthalen-1-yl)phenyl)-9H-fluorene-2-amine and 6.58 g (16.5 mmol) of 1-(4"-chloro-[1,1':4',1"-terphenyl]-4-yl)adamantane were used.

Synthesis Example 33: Preparation of Compound 139

Compound 139 was prepared by the same method as described in Synthesis Example 1, except that 6.17 g (15.0 mmol) of 9,9-dimethyl-N-(2-(naphthalen-2-yl)phenyl)-9H-fluorene-2-amine and 6.58 g (16.5 mmol) of 1-(4"-chloro-[1,1':4',1"-terphenyl]-4-yl)adamantane were used.

NMR and yield data of the compounds synthesized as described above are shown in Table 1 below.

TABLE 1

| Compound | $^1$H-NMR (400 MHz, CDCl$_3$): (ppm) | Yield (%) |
|---|---|---|
| Compound 1 | 7.66 (d, J = 7.6 Hz, 1H), 7.62-7.59 (m, 3H), 7.56 (d, J = 8.8 Hz, 2H), 7.52 (dd, J = 8.4 Hz, 4H), 7.44-7.39 (m, 5H), 7.33-7.26 (m, 4H), 7.24-7.21 (m, 4H), 7.13 (dd, J = 8.4 Hz, 1H), 2.12 (brs, 3H), 1.96 (d, J = 2.4 Hz, 6H), 1.83-1.75 (m, 6H), 1.44 (s, 6H) | 20 |
| Compound 6 | 7.56 (d, J = 7.6 Hz, 1H), 7.51 (d, J = 8.4 Hz, 2H), 7.41-7.34 (m, 8H), 7.32-7.25 (m, 3H), 7.23-7.16 (m, 3H), 7.07-6.99 (m, 5H), 6.87 (d, J = 2.0 Hz, 1H), 6.78 (dd, J = 8.4 Hz, 1H), 2.11 (brs, 3H), 1.95 (d, J = 2.4 Hz, 6H), 1.82-1.75 (m, 6H), 1.29 (s, 6H) | 51 |
| Compound 18 | 7.84-7.80 (m, 2H), 7.65 (d, J = 7.6 Hz, 1H), 7.60-7.48 (m, 7H), 7.46-7.37 (m, 4H), 7.34-7.23 (m, 5H), 7.19 (d, J = 8.8 Hz, 2H), 7.10 (dd, J = 8.4 Hz, 1H), 2.11 (brs, 3H), 1.96 (d, J = 2.4 Hz, 6H), 1.83-1.75 (m, 6H), 1.42 (s, 6H) | 59 |
| Compound 27 | 7.64 (d, J = 7.2 Hz, 2H), 7.57 (d, J = 8.0 Hz, 2H), 7.38 (d, J = 7.2 Hz, 2H), 7.32-7.22 (m, 8H), 7.14 (d, J = 8.4 Hz, 2H), 7.06 (d, J = 8.0 Hz, 2H), 2.10 (brs, 3H), 1.94 (d, J = 2.4 Hz, 6H), 1.81-1.74 (m, 6H), 1.40 (s, 12H) | 54 |
| Compound 29 | 7.65 (d, J = 7.6 Hz, 2H), 7.60 (d, J = 8.4 Hz, 2H), 7.46-7.36 (m, 6H), 7.34-7.24 (m, 9H), 7.15-7.10 (m, 3H), 2.08 (brs, 3H), 1.90 (d, J = 2.4 Hz, 6H), 1.80-1.72 (m, 6H), 1.42 (s, 12H) | 33 |
| Compound 30 | 7.65 (d, J = 7.2 Hz, 2H), 7.61 (d, J = 8.4 Hz, 2H), 7.57 (d, J = 8.4 Hz, 2H), 7.52 (d, J = 8.4 Hz, 2H), 7.43 (d, J = 8.4 Hz, 2H), 7.39 (d, J = 7.2 Hz, 2H), 7.33-7.22 (m, 8H), 7.13 (d, J = 7.2 Hz, 2H), 2.12 (brs, 3H), 1.96 (d, J = 2.4 Hz, 6H), 1.83-1.75 (m, 6H), 1.41 (s, 12H) | 36 |
| Compound 31 | 7.57 (d, J = 7.2 Hz, 2H), 7.42-7.33 (m, 7H), 7.31-7.26 (m, 3H), 7.23-7.15 (m, 4H), 7.06 (d, J = 8.4 Hz, 2H), 7.00 (s, 2H), 6.84 (d, J = 8.8 Hz, 2H), 1.97 (brs, 3H), 1.71-1.61 (m, 12H), 1.32 (s, 12H) | 50 |
| Compound 32 | 8.07 (d, J = 7.6 Hz, 1H), 7.92 (dd, J = 6.8 Hz, 1H), 7.85 (d, J = 8.0 Hz, 1H), 7.67-7.63 (m, 2H), 7.58-7.52 (m, 5H), 7.51-7.47 (m, 3H), 7.44-7.40 (m, 5H), 7.33-7.27 (m, 7H), 7.19 (dd, J = 8.0 Hz, 1H), 2.12 (brs, 3H), 1.96 (d, J = 2.4 Hz, 6H), 1.83-1.75 (m, 6H), 1.46 (s, 6H) | 50 |
| Compound 33 | 8.04 (s, 1H), 7.91-7.84 (m, 3H), 7.77 (dd, J = 8.4 Hz, 1H), 7.67-7.61 (m, 4H), 7.57-7.51 (m, 4H), 7.50-7.39 (m, 5H), 7.34-7.23 (m, 7H), 7.15 (d, J = 8.4 Hz, 1H), 2.12 (brs, 3H), 1.96 (d, J = 2.4 Hz, 6H), 1.83-1.75 (m, 6H), 1.45 (s, 6H) | 85 |
| Compound 34 | 7.63 (d, J = 7.2 Hz, 1H), 7.59-7.54 (m, 3H), 7.50-7.44 (m, 5H), 7.42-7.27 (m, 9H), 7.26-7.15 (m, 4H), 7.04 (d, J = 8.8 Hz, 2H), 6.81 (s, 1H), 6.77 (dd, J = 8.0 Hz, 1H), 2.11 (brs, 3H), 1.95 (d, J = 2.4 Hz, 6H), 1.82-1.75 (m, 6H), 1.06 (s, 6H) | 67 |
| Compound 35 | 7.99 (d, J = 8.4 Hz, 1H), 7.91 (d, J = 8.4 Hz, 1H), 7.80 (d, J = 8.4 Hz, 1H), 7.61 (d, J = 7.2 Hz, 1H), 7.53-7.46 (m, 5H), 7.45-7.35 (m, 7H), 7.33-7.21 (m, 3H), 7.09 (d, J = 8.8 Hz, 2H), 6.98 (dd, J = 8.0 Hz, 1H), 2.11 (brs, 3H), 1.95 (d, J = 2.8 Hz, 6H), 1.82-1.74 (m, 6H), 1.38 (s, 6H) | 26 |
| Compound 36 | 7.78-7.73 (m, 2H), 7.66 (d, J = 7.2 Hz, 1H), 7.61 (d, J = 8.0 Hz, 2H), 7.57 (d, J = 8.8 Hz, 2H), 7.52 (d, J = 8.8 Hz, 3H), 7.43-7.40 (m, 3H), 7.38-7.33 (m, 3H), 7.31-7.26 (m, 3H), 7.23 (d, J = 8.8 Hz, 2H), 7.13 (dd, J = 8.4 Hz, 1H), 2.11 (brs, 3H), 1.96 (d, J = 2.0 Hz, 6H), 1.83-1.75 (m, 6H), 1.42 (s, 6H) | 32 |
| Compound 37 | 7.62 (d, J = 8.0 Hz, 1H), 7.56-7.49 (m, 4H), 7.44-7.40 (m, 1H), 7.36 (d, J = 7.6 Hz, 1H), 7.31 (d, J = 7.6 Hz, 2H), 7.26-7.22 (m, 3H), 7.20-7.12 (m, 3H), 7.09 (d, J = 6.8 Hz, 1H), 7.11 (d, J = 8.8 Hz, 2H), 6.70 (s, 1H), 6.65 (d, J = 8.4 Hz, 3H), 2.04 (brs, 3H), 1.77-1.68 (m, 12H), 1.24 (s, 6H) | 53 |
| Compound 38 | 7.62-7.44 (m, 6H), 7.40-7.37 (m, 5H), 7.34-7.29 (m, 2H), 7.27-7.09 (m, 9H), 6.81 (d, J = 8.8 Hz, 2H), 6.66-6.63 (m, 2H), 2.11 (brs, 3H), 1.95 (d, J = 2.0 Hz, 6H), 1.82-1.75 (m, 6H), 1.23 (d, J = 5.2 Hz, 6H) | 55 |
| Compound 39 | 8.09 (d, J = 8.0 Hz, 1H), 7.97 (d, J = 7.6 Hz, 1H), 7.62 (d, J = 7.2 Hz, 1H), 7.57-7.49 (m, 7H), 7.47-7.42 (m, 5H), 7.41-7.34 (m, 5H), 7.31-7.22 (m, 3H), 7.14 (d, J = 8.4 Hz, 2H), 7.02 (dd, J = 8.4 Hz, 1H), 2.11 (brs, 3H), 1.95 (d, J = 2.4 Hz, 6H), 1.82-1.74 (m, 6H), 1.41 (s, 6H) | 37 |
| Compound 40 | 8.07 (d, J = 8.4 Hz, 1H), 7.95 (d, J = 8.8 Hz, 1H), 7.59 (d, J = 7.2 Hz, 1H), 7.56-7.48 (m, 5H), 7.45-7.40 (m, 3H), 7.39-7.32 (m, 3H), 7.29-7.20 (m, 5H), 7.08 (d, J = 8.8 Hz, 2H), 6.93 (dd, J = 8.0 Hz, 1H), 2.08 (brs, 3H), 1.91 (d, J = 2.4 Hz, 6H), 1.79-1.72 (m, 6H), 1.39 (s, 6H) | 77 |
| Compound 57 | 8.74-8.69 (m, 2H), 8.08 (d, J = 8.4 Hz, 1H), 7.76 (d, J = 7.6 Hz, 1H), 7.65-7.53 (m, 5H), 7.49-7.42 (m, 2H), 7.35 (d, J = 7.2 Hz, 1H), 7.28-7.18 (m, 5H), 7.09 (d, J = 8.4 Hz, 2H), 6.97 (dd, J = 8.0 Hz, 1H), 2.07 (brs, 3H), 1.90 (d, J = 2.4 Hz, 6H), 1.79-1.71 (m, 6H), 1.35 (s, 6H) | 59 |
| Compound 58 | 8.77-8.71 (m, 2H), 8.10 (d, J = 8.4 Hz, 1H), 7.79 (d, J = 8.0 Hz, 1H), 7.67-7.63 (m, 3H), 7.61-7.57 (m, 2H), 7.56-7.50 (m, 3H), 7.49-7.43 (m, 3H), 7.41-7.35 (m, 3H), 7.31-7.27 (m, 2H), 7.25-7.21 (m, 1H), 7.17-7.14 (m, 2H), 7.07 (dd, J = 8.0 Hz, 1H), 2.10 (brs, 3H), 1.94 (d, J = 2.4 Hz, 6H), 1.82-1.74 (m, 6H), 1.38 (s, 6H) | 21 |
| Compound 60 | 7.67 (d, J = 7.2 Hz, 2H), 7.60-7.56 (m, 2H) 7.55 (d, J = 7.2 Hz, 1H), 7.46-7.40 (m, 3H), 7.33 (t, J = 7.2 Hz, 3H), 7.28-7.24 (m, 1H), 7.21-7.19 (m, 3H), 7.14 (d, J = 8.4 Hz, 2H), 7.06-6.95 (m, 5H), 6.86 (s, 1H), 6.77 (d, J = 8.0 Hz, 1H), 2.09 (brs, 3H), 1.89 (d, J = 2.0 Hz, 6H), 1.80-1.73 (m, 6H), 1.29 (s, 6H) | 23 |

TABLE 1-continued

| Compound | ¹H-NMR (400 MHz, CDCl₃): (ppm) | Yield (%) |
|---|---|---|
| Compound 61 | 7.68 (d, J = 8.0 Hz, 2H), 7.63-7.58 (m, 2H) 7.57 (d, J = 7.2 Hz, 1H), 7.52 (d, J = 8.4 Hz, 2H), 7.47 (d, J = 8.4 Hz, 2H), 7.43-7.36 (m, 6H), 7.34 (d, J = 7.2 Hz, 2H), 7.29-7.19 (m, 4H), 7.09-7.00 (m, 5H), 6.92 (s, 1H), 6.84 (d, J = 8.0 Hz, 1H), 2.11 (brs, 3H), 1.97 (d, J = 2.0 Hz, 6H), 1.83-1.75 (m, 6H), 1.29 (s, 6H) | 59 |
| Compound 62 | 7.72 (d, J = 7.6 Hz, 2H), 7.65 (s, 2H), 7.53 (d, J = 7.2 Hz, 1H), 7.47-7.42 (m, 4H), 7.39-7.35 (m, 3H), 7.33-7.27 (m, 3H), 7.25-7.23 (m, 5H), 7.21-7.15 (m, 3H), 7.06-6.97 (m, 6H), 6.88-6.82 (m, 4H), 2.11 (brs, 3H), 1.95 (s, 6H), 1.82-1.75 (m, 6H), 1.26 (s, 6H) | 28 |
| Compound 64 | 7.64-7.57 (m, 6H), 7.46 (d, J = 8.0 Hz, 5H), 7.35 (d, J = 7.2 Hz, 2H), 7.30-7.20 (m, 6H), 7.07-6.96 (m, 5H), 6.92 (d, J = 8.0 Hz, 2H), 2.12 (brs, 3H), 1.97 (s, 6H), 1.83-1.76 (m, 6H), 1.31 (s, 12H) | 43 |
| Compound 67 | 7.70 (d, J = 8.0 Hz, 1H), 7.63-7.60 (m, 8H), 7.57 (dd, J = 7.6 Hz, 1H), 7.53 (d, J = 8.8 Hz, 4H), 7.47-7.41 (m, 6H), 7.33-7.29 (m, 3H), 7.25 (d, J = 8.4 Hz, 4H), 7.14 (d, J = 8.0 Hz, 1H), 2.13 (brs, 3H), 1.98 (d, J = 2.4 Hz, 6H), 1.84-1.76 (m, 6H), 1.48 (s, 6H) | 24 |
| Compound 68 | 7.62-7.57 (m, 4H), 7.54-7.51 (m, 2H), 7.46-7.37 (m, 6H), 7.36-7.26 (m, 4H), 7.24-7.19 (m, 3H), 7.06-6.96 (m, 5H), 6.85 (brs, 2H), 2.12 (brs, 3H), 1.97 (d, J = 2.4 Hz, 6H), 1.83-1.76 (m, 6H), 1.34 (s, 6H), 1.31 (s, 6H) | 63 |
| Compound 110 | 7.66-7.59 (m, 10H), 7.57-7.51 (m, 4H), 7.46-7.39 (m, 5H), 7.33-7.29 (m, 3H), 7.27-7.23 (m, 5H), 7.14 (d, J = 8.4 Hz, 1H), 2.12 (brs, 3H), 1.97 (d, J = 2.4 Hz, 6H), 1.83-1.76 (m, 6H), 1.44 (s, 6H) | 16 |
| Compound 111 | 7.65-7.59 (m, 6H), 7.57 (d, J = 7.6 Hz, 1H), 7.46-7.42 (m, 5H), 7.40-7.35 (m, 3H), 7.33-7.25 (m, 3H), 7.23-7.17 (m, 3H), 7.09-7.00 (m, 5H), 6.88 (d, J = 2.0 Hz, 1H), 6.78 (dd, J = 8.0 Hz, 1H), 2.12 (brs, 3H), 1.97 (d, J = 2.4 Hz, 6H), 1.83-1.76 (m, 6H), 1.30 (s, 6H) | 40 |
| Compound 122 | 7.67-7.60 (m, 10H), 7.57 (d, J = 8.8 Hz, 2H), 7.47 (d, J = 8.4 Hz, 2H), 7.40 (d, J = 7.6 Hz, 2H), 7.34-7.25 (m, 8H), 7.14 (d, J = 8.0 Hz, 2H), 2.12 (brs, 3H), 1.97 (d, J = 2.4 Hz, 6H), 1.83-1.76 (m, 6H), 1.42 (s, 12H) | 58 |
| Compound 129 | 8.77-8.71 (m, 2H), 8.11 (d, J = 8.4 Hz, 1H), 7.79 (d, J = 7.6 Hz, 1H), 7.68-7.56 (m, 11H), 7.55 (d, J = 8.0 Hz, 1H), 7.51-7.43 (m, 5H), 7.38 (d, J = 7.6 Hz, 1H), 7.31-7.22 (m, 3H), 7.19 (d, J = 8.4 Hz, 2H), 7.08 (dd, J = 8.0 Hz, 1H), 2.12 (brs, 3H), 1.96 (d, J = 2.4 Hz, 6H), 1.83-1.75 (m, 6H), 1.39 (s, 6H) | 54 |
| Compound 135 | 7.99 (d, J = 8.4 Hz, 1H), 7.92 (d, J = 8.0 Hz, 1H), 7.80 (d, J = 8.0 Hz, 1H), 7.65-7.58 (m, 6H), 7.54-7.45 (m, 6H), 7.43-7.34 (m, 4H), 7.31-7.22 (m, 4H), 7.11 (d, J = 8.8 Hz, 2H), 7.00 (dd, J = 8.0 Hz, 1H), 2.12 (brs, 3H), 1.97 (d, J = 2.4 Hz, 6H), 1.83-1.75 (m, 6H), 1.39 (s, 6H) | 56 |
| Compound 136 | 7.79-7.74 (m, 2H), 7.67-7.60 (m, 9H), 7.57-7.54 (m, 3H), 7.47 (d, J = 8.4 Hz, 2H), 7.43-7.35 (m, 4H), 7.34-7.24 (m, 5H), 7.14 (dd, J = 8.4 Hz, 2H), 2.12 (brs, 3H), 1.97 (d, J = 2.4 Hz, 6H), 1.83-1.76 (m, 6H), 1.43 (s, 6H) | 18 |
| Compound 137 | 8.10 (d, J = 8.0 Hz, 1H), 7.98 (d, J = 8.4 Hz, 1H), 7.64-7.57 (m, 7H), 7.56-7.50 (m, 6H), 7.46-7.36 (m, 8H), 7.34-7.23 (m, 4H), 7.17 (d, J = 8.8 Hz, 2H), 7.04 (dd, J = 8.0 Hz, 1H), 2.12 (brs, 3H), 1.97 (d, J = 2.4 Hz, 6H), 1.83-1.75 (m, 6H), 1.42 (s, 6H) | 59 |
| Compound 138 | 7.62-7.55 (m, 7H), 7.53 (d, J = 7.6 Hz, 1H), 7.50-7.39 (m, 6H), 7.36-7.30 (m, 2H), 7.27-7.22 (m, 6H), 7.20-7.11 (m, 4H), 6.85 (d, J = 8.4 Hz, 2H), 6.66 (d, J = 8.0 Hz, 2H), 2.12 (brs, 3H), 1.97 (d, J = 2.4 Hz, 6H), 1.83-1.76 (m, 6H), 1.24 (d, J = 6.0 Hz, 6H) | 25 |
| Compound 139 | 7.64-7.55 (m, 10H), 7.51-7.44 (m, 6H), 7.41-7.35 (m, 4H), 7.33-7.26 (m, 4H), 7.23-7.16 (m, 2H), 7.07 (d, J = 8.4 Hz, 2H), 6.81 (s, 1H), 6.78 (d, J = 8.0 Hz, 1H), 2.12 (brs, 3H), 1.97 (d, J = 2.4 Hz, 6H), 1.83-1.76 (m, 6H), 1.06 (s, 6H) | 60 |

Comparative Example 1: Preparation of Compound A

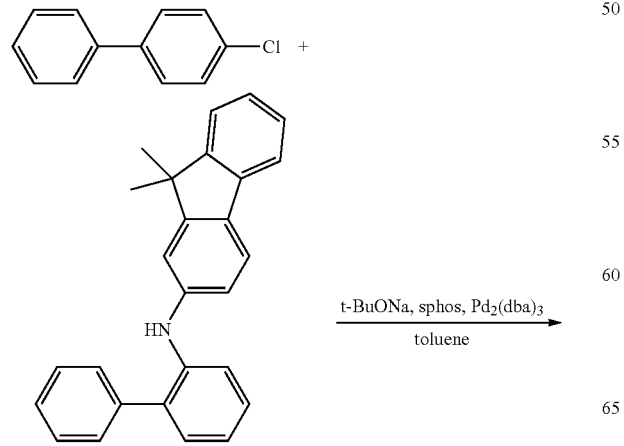

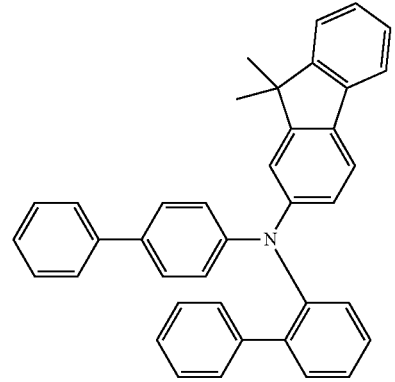

5.42 g (15.0 mmol) of N-([1,1'-biphenyl]-2-yl)-9,9-dimethyl-9H-fluorene-2-amine and 3.11 g (16.5 mmol) of 4-chloro-1,1'-biphenyl were dissolved in 100 ml of toluene, and 4.32 g (45.0 mmol) of sodium tert-butoxide, 246 mg (0.60 mmol) of 2-dicyclohexylphosphino-2',6''-dimethoxybiphenyl and 275 mg (0.30 mmol) of tris(dibenzylideneacetone)dipalladium(0) were added thereto, followed by refluxing for 12 hours. After the reaction was completed, the resulting solution was cooled to room temperature, and then an organic layer was extracted using 100 ml of dichloromethane and 50 ml of $H_2O$. Following dehydration of the organic layer with $MgSO_4$, the remaining solution was distilled and subjected to column chromatography using n-hexane/dichloromethane, thereby obtaining 6.73 g of Compound A with a yield of 68%.

$^1$H-NMR (400 MHz, CDCl3): (ppm) 7.56 (d, J=8.0 Hz, 3H), 7.42-7.34 (m, 9H), 7.32-7.27 (m, 3H), 7.23-7.17 (m, 3H), 7.08-6.99 (m, 5H), 6.87 (s, 1H), 6.78 (dd, J=8.4 Hz, 1H), 1.29 (s, 6H)

Comparative Example 2: Preparation of Compound B

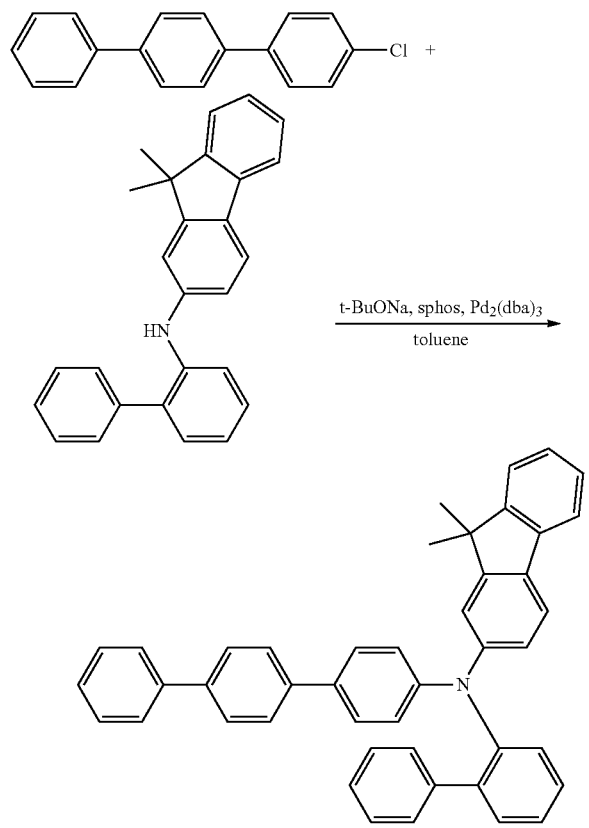

5.42 g (15.0 mmol) of N-([1,1'-biphenyl]-2-yl)-9,9-dimethyl-9H-fluorene-2-amine and 4.37 g (16.5 mmol) of 4-chloro-1,1':4',1''-terphenyl were dissolved in 100 ml of toluene, and 4.32 g (45.0 mmol) of sodium tert-butoxide, 246 mg (0.60 mmol) of 2-dicyclohexylphosphino-2',6''-dimethoxybiphenyl and 275 mg (0.30 mmol) of tris(dibenzylideneacetone)dipalladium(0) were added thereto, followed by refluxing for 12 hours. After the reaction was completed, the resulting solution was cooled to room temperature, and then an organic layer was extracted using 100 ml of dichloromethane and 50 ml of $H_2O$. Following dehydration of the organic layer with $MgSO_4$, the remaining solution was distilled and subjected to column chromatography using n-hexane/dichloromethane, thereby obtaining 7.79 g of Compound B with a yield of 68%.

$^1$H-NMR (400 MHz, CDCl3): (ppm) 7.66-7.61 (m, 6H), 7.57 (d, J=7.6 Hz, 1H), 7.47-7.41 (m, 5H), 7.40-7.26 (m, 7H), 7.24-7.18 (m, 3H), 7.09-7.00 (m, 5H), 6.88 (s, 1H), 6.79 (dd, J=8.4 Hz, 1H), 1.30 (s, 6H)

Example 1: Preparation of OLED Using Compound 1 as HTL Material

A substrate on which an Ag alloy as a light reflection layer and ITO (10 nm) as an anode of an OLED were sequentially laminated was patterned into cathode and anode areas and an insulating layer through photolithography, and then treated with UV-<0253> ozone and surface-treated with $O_2:N_2$ plasma for an increase in the work function of the anode (ITO) and descumming. Thereon, 1,4,5,8,9,11-hexaazatriphenylene-hexacarbonitrile (HAT-CN) as a HIL was formed to have a thickness of 100 Å. Subsequently, HTL having a thickness of 1000 Å was formed on the HIL by vacuum deposition of Compound 1. N-phenyl-N-(4-(spiro[benzo[de] anthracen-7,9'-fluorene]-2'-yl)phenyl)dibenzo[b,d]furan-4-amine as an EBL was formed on the HTL to have a thickness of 150 Å, and while α,β-ADN as a host material capable of forming a blue EML as an EML was deposited on the EBL, N1,N1,N6,N6-tetrakis(4-(1-silyl)phenyl)pyrene-1,6-diamine as a dopant was doped, resulting in formation of an EML with a thickness of 200 Å.

On the EML, 2-(4-(9,10-di(naphthalen-2-yl)anthracen-2-yl)phenyl)-1-phenyl-1H-benzo[d]imidazole and LiQ were mixed at a weight ratio of 1:1 and deposited, thereby forming an ETL with a thickness of 360 Å, and as a cathode, magnesium (Mg) and silver (Ag) were mixed at 9:1 and deposited to a thickness of 160 Å. As a capping layer, N4,N4'-diphenyl-N4,N4'-bis(4-(9-phenyl-9H-carbazol-3-yl)phenyl)-[1,1'-biphenyl]-4,4'-diamine was deposited on the cathode to have a thickness of 63 to 65 nm. A seal cap was laminated on the capping layer (CPL) using a UV-curable adhesive so as to protect an OLED from $O_2$ or moisture in air, and therefore, an OLED was manufactured.

Examples 2 to 33

OLEDs were manufactured by the same method as described in Example 1, except that Compounds 6, 18, 27, 29 to 40, 57, 58, 60, 61, 62, 64, 67, 68, 110, 111, 122, 129, and 135 to 139, respectively, were used, instead of Compound 1, as a HTL.

Comparative Examples 1 to 3

OLEDs were manufactured by the same method as described in Example 1, except that NPB, and Compounds A and B, respectively, were used, instead of Compound 1, as a HTL.

The performance of the OLEDs manufactured as described above was analyzed under a condition of 10 mA/cm$^2$, and results are shown in Table 2 below.

TABLE 2

| | Compound | V | Cd/A | Cd/m² | lm/W | EQE | CIEx | CIEy |
|---|---|---|---|---|---|---|---|---|
| Example1 | Compound1 | 4.4 | 4.0 | 395 | 2.8 | 7.7 | 0.139 | 0.050 |
| Example2 | Compound6 | 3.9 | 5.4 | 536 | 4.3 | 9.8 | 0.135 | 0.056 |
| Example3 | Compound18 | 4.6 | 5.1 | 513 | 3.5 | 9.6 | 0.136 | 0.053 |
| Example4 | Compound27 | 4.1 | 5.3 | 528 | 4.0 | 10.0 | 0.136 | 0.053 |
| Example5 | Compound29 | 4.5 | 5.5 | 551 | 3.9 | 9.9 | 0.134 | 0.057 |
| Example6 | Compound30 | 4.1 | 6.2 | 620 | 4.7 | 10.6 | 0.132 | 0.062 |
| Example7 | Compound31 | 4.1 | 4.3 | 435 | 3.3 | 8.7 | 0.138 | 0.049 |
| Example8 | Compound32 | 4.4 | 5.9 | 591 | 4.2 | 10.0 | 0.132 | 0.062 |
| Example9 | Compound33 | 4.5 | 5.9 | 591 | 4.1 | 10.1 | 0.132 | 0.062 |
| Example10 | Compound34 | 4.1 | 5.6 | 557 | 4.3 | 10.0 | 0.134 | 0.057 |
| Example11 | Compound35 | 4.0 | 5.9 | 587 | 4.6 | 9.7 | 0.131 | 0.065 |
| Example12 | Compound36 | 4.3 | 5.4 | 537 | 3.9 | 9.8 | 0.135 | 0.056 |
| Example13 | Compound37 | 4.1 | 4.7 | 468 | 3.6 | 9.1 | 0.138 | 0.050 |
| Example14 | Compound38 | 4.2 | 4.4 | 437 | 3.3 | 7.8 | 0.136 | 0.056 |
| Example15 | Compound39 | 4.1 | 6.2 | 622 | 4.8 | 10.6 | 0.132 | 0.062 |
| Example16 | Compound40 | 4.1 | 4.5 | 448 | 3.4 | 8.6 | 0.137 | 0.051 |
| Example17 | Compound57 | 4.0 | 5.3 | 530 | 4.1 | 9.4 | 0.134 | 0.058 |
| Example18 | Compound58 | 4.0 | 4.7 | 470 | 3.7 | 8.4 | 0.134 | 0.057 |
| Example19 | Compound61 | 3.9 | 5.9 | 586 | 4.7 | 9.8 | 0.131 | 0.064 |
| Example20 | Compound62 | 3.9 | 3.9 | 386 | 3.1 | 7.8 | 0.139 | 0.048 |
| Example21 | Compound64 | 3.9 | 4.5 | 449 | 3.6 | 8.6 | 0.137 | 0.051 |
| Example22 | Compound60 | 4.1 | 4.6 | 465 | 3.6 | 9.1 | 0.137 | 0.050 |
| Example23 | Compound67 | 4.4 | 5.0 | 496 | 3.5 | 9.3 | 0.136 | 0.053 |
| Example24 | Compound68 | 4.2 | 4.2 | 422 | 3.1 | 8.2 | 0.137 | 0.051 |
| Example25 | Compound110 | 4.4 | 4.9 | 492 | 3.5 | 8.9 | 0.134 | 0.057 |
| Example26 | Compound111 | 4.2 | 5.9 | 586 | 4.4 | 10.5 | 0.134 | 0.057 |
| Example27 | Compound122 | 4.3 | 5.4 | 537 | 3.9 | 9.6 | 0.134 | 0.057 |
| Example28 | Compound129 | 4.0 | 5.1 | 509 | 4.0 | 9.4 | 0.135 | 0.055 |
| Example29 | Compound135 | 4.2 | 4.7 | 474 | 3.5 | 8.8 | 0.136 | 0.054 |
| Example30 | Compound136 | 4.3 | 5.2 | 517 | 3.8 | 9.8 | 0.136 | 0.053 |
| Example31 | Compound137 | 4.6 | 5.1 | 510 | 3.5 | 9.5 | 0.136 | 0.054 |
| Example32 | Compound138 | 4.2 | 4.7 | 466 | 3.5 | 8.4 | 0.134 | 0.057 |
| Example33 | Compound139 | 4.1 | 5.7 | 569 | 4.4 | 9.3 | 0.13 | 0.066 |
| Comparative Example1 | NPB | 4.6 | 4.0 | 392 | 3.0 | 6.4 | 0.132 | 0.061 |
| Comparative Example2 | Compound A | 4.0 | 4.7 | 468 | 3.7 | 8.7 | 0.135 | 0.055 |
| Comparative Example3 | Compound B | 4.1 | 5.1 | 514 | 4.0 | 8.9 | 0.133 | 0.060 |

As shown in Table 2, it can be confirmed that, when each compound according to the present invention was used as a HTL, the OLED exhibited the same or a lower driving voltage than those of the comparative examples, and exhibited enhanced brightness (cd/m²) and external quantum efficiency (EQE), compared with the diodes of the comparative examples. Accordingly, it can be seen that the OLEDs have low voltage and high efficiency. In addition, CIEy values in the colorimetric purity are detected in a shorter wavelength region than those of the comparative examples.

TABLE 3

| | Compound | Structure | Tg (° C.) | Td (° C.) |
|---|---|---|---|---|
| Example 2 | Compound 6 | 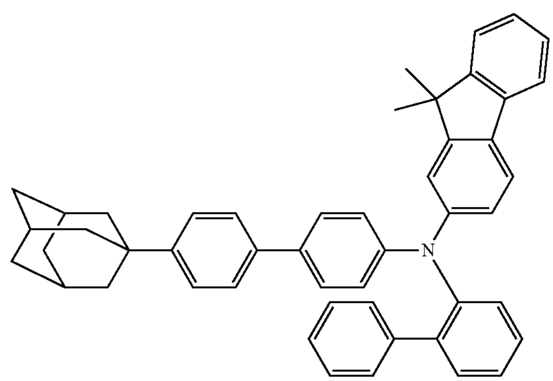 [SMILES: CC1(C)c2ccccc2-c2ccc(N(c3ccc(-c4ccc(C56CC7CC(CC(C7)C5)C6)cc4)cc3)c3ccccc3-c3ccccc3)cc21] | 127 | 368 |

TABLE 3-continued

| Compound | | Structure | Tg (° C.) | Td (° C.) |
|---|---|---|---|---|
| Example 6 | Compound 30 | 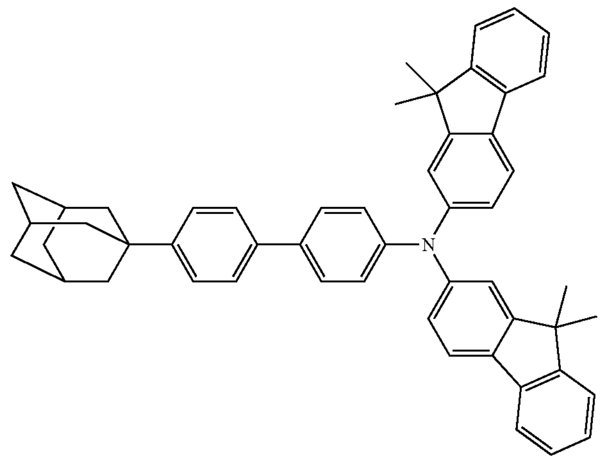 [SMILES: CC1(C)c2ccccc2-c2ccc(N(c3ccc(-c4ccc(C56CC7CC(CC(C7)C5)C6)cc4)cc3)c3ccc4c(c3)C(C)(C)c3ccccc3-4)cc21] | 156 | 387 |
| Example 26 | Compound 111 | 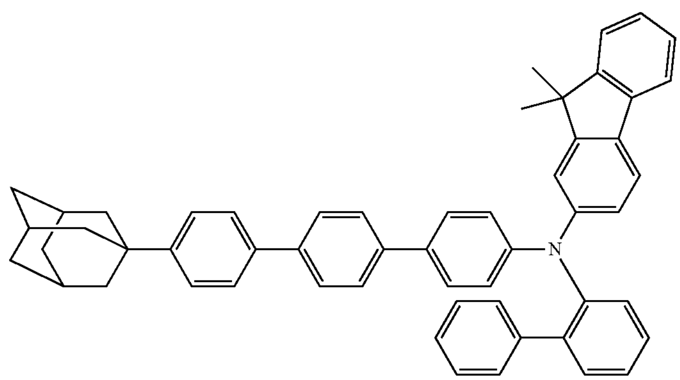 [SMILES: CC1(C)c2ccccc2-c2ccc(N(c3ccc(-c4ccc(-c5ccc(C67CC8CC(CC(C8)C6)C7)cc5)cc4)cc3)c3ccccc3-c3ccccc3)cc21] | 136 | 405 |
| Comparative Example 2 | Compound A | 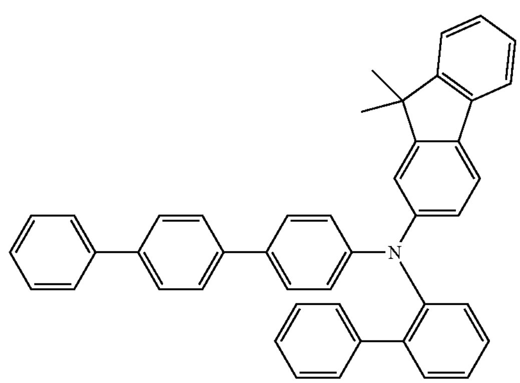 [SMILES: CC1(C)c2ccccc2-c2ccc(N(c3ccc(-c4ccc(-c5ccccc5)cc4)cc3)c3ccccc3-c3ccccc3)cc21] | 100 | 339 |
| Comparative Example 3 | Compound B | 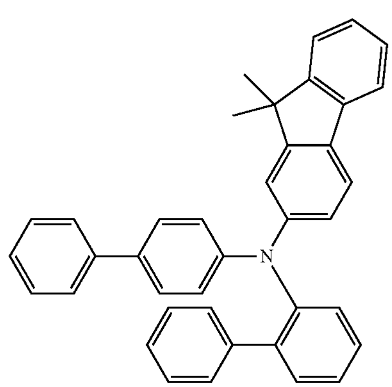 [SMILES: CC1(C)c2ccccc2-c2ccc(N(c3ccc(-c4ccccc4)cc3)c3ccccc3-c3ccccc3)cc21] | 84 | 297 |

TABLE 4

Diode Results I (before thermal treatment)

| | Compound | V | Cd/A | Cd/m² | lm/W | EQE | CIEx | CIEy |
|---|---|---|---|---|---|---|---|---|
| Example 2 | Compound6 | 3.9 | 5.4 | 536 | 4.3 | 9.8 | 0.135 | 0.056 |
| Example 6 | Compound30 | 4.1 | 6.2 | 620 | 4.7 | 10.6 | 0.132 | 0.062 |
| Example 26 | Compound111 | 4.2 | 5.9 | 586 | 4.4 | 10.5 | 0.134 | 0.057 |
| Comparative Example 2 | Compound A | 4.1 | 5.1 | 514 | 4.0 | 8.9 | 0.133 | 0.060 |
| Comparative Example 3 | Compound B | 4.0 | 4.7 | 468 | 3.7 | 8.7 | 0.135 | 0.055 |

TABLE 5

Diode Results II (after thermal treatment)

| | Compound | V | Cd/A | Cd/m² | lm/W | EQE | CIEx | CIEy |
|---|---|---|---|---|---|---|---|---|
| Example 2 | Compound6 | 3.6 | 5.4 | 538 | 4.8 | 9.9 | 0.135 | 0.055 |
| Example 6 | Compound30 | 3.8 | 6.3 | 627 | 5.2 | 10.9 | 0.133 | 0.060 |
| Example 26 | Compound111 | 3.8 | 5.5 | 549 | 4.3 | 10.9 | 0.134 | 0.058 |
| Comparative Example 2 | Compound A | 5.1 | 0.2 | 18 | 0.1 | 0.1 | 0.157 | 0.161 |
| Comparative Example 3 | Compound B | 4.5 | 0.3 | 341 | 0.2 | 0.2 | 0.153 | 0.152 |

It can be confirmed from Table 3 that, when comparing Compound 6 with Compound A containing a phenyl, rather than adamantane, Compound 6 has a glass transition temperature and a decomposition temperature that are higher by 27° C. and 29° C., respectively, than Compound A, and a glass transition temperature and a decomposition temperature that are higher by 43° C. and 71° C., respectively, than Compound B without adamantane. Compound 30 and Compound 111 also showed similar results thereto.

Such excellent thermal properties of the compounds of the present invention are particularly evident in thermal stability results of diodes, which were obtained by measuring the performance of diodes manufactured using the compounds of the present invention (Compounds 6, 30 and 111) and the comparative compounds (Compounds A and B) before and after maintaining them at 110° C. for 1 hour. Results obtained before and after the thermal treatment are summarized in Table 4 (before the thermal treatment) and Table 5 (after the thermal treatment).

As shown in Tables 4 and 5, it can be confirmed that, before and after the thermal treatment of the diodes using the materials of the comparative examples, efficiency and external quantum efficiency are reduced by 90% or more. In contrast, it can be confirmed that, before and after the thermal treatment of the diode using the compound of the present invention, efficiency and external quantum efficiency are maintained at similar levels or higher due to the excellent thermal properties.

Therefore, according to Tables 2 to 5 showing the results of the OLEDs according to the examples, a highly-efficient and highly thermal resistant OLED with excellent properties in terms of a driving voltage, light emitting efficiency, external quantum efficiency (EQE) and thermal stability may be manufactured using the adamantane-introduced arylamine compound of the present invention as a hole transport material.

This demonstrates that, if an aliphatic group such as adamantane, which is considered an insulator, is designed to prevent the interruption of packing between π-electrons of hole transfer-associated organic materials, a material that cannot be used due to low Tg despite excellent hole injection and transfer characteristics can be practically applied in diodes.

INDUSTRIAL APPLICABILITY

The present invention relates to a novel organic compound and an organic light-emitting diode (OLED) including the same, and more particularly, to an adamantane derivative compound with high thermal resistance, excellent chemical stability, excellent charge mobility and an excellent interfacial property with an electrode or an adjacent layer, and an OLED which includes the adamantane derivative compound as a material for one or more organic material layers, thereby exhibiting excellent properties such as a low driving voltage, excellent light emitting efficiency, excellent external quantum efficiency (EQE) and excellent thermal stability.

What is claimed is:

1. A compound represented by Formula 1 below:

[Formula 1]

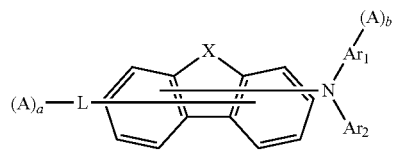

wherein
each of a and b is an integer of 0 or 1, and a+b=1 or 2,
A is a substituted or unsubstituted adamantyl group, with the proviso that when A is a substituted adamantyl group the substituent group excludes aryl groups,
X is selected from the group consisting of $N(R_1)$, S, O, $C(R_1)(R_2)$ and $Si(R_1)(R_2)$,
$R_1$ to $R_2$ are the same or different, and are each independently hydrogen, deuterium, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, and a substituted or unsubstituted heteroarylalkyl group having 3 to 30 carbon atoms,
$R_1$ and $R_2$ may be connected to each other, forming a saturated or unsaturated ring compound,
L is selected from the group consisting of a single bond, a substituted or unsubstituted arylene group having 6 to 30 carbon atoms, a substituted or unsubstituted heteroarylene group having 6 to 30 nuclear carbon atoms, a substituted or unsubstituted alkylene group having 2 to 10 carbon atoms, a substituted or unsubstituted cycloalkylene group having 2 to 10 carbon atoms, a substituted or unsubstituted alkenylene group having 2 to 10 carbon atoms, a substituted or unsubstituted cycloalkenylene group having 2 to 10 carbon atoms substituted or unsubstituted heteroalkylene group having 2 to 10 carbon atoms, a substituted or unsubstituted heterocycloalkylene group having 2 to 10 carbon atoms, a substituted or unsubstituted heteroalkenylene group having 2 to 10 carbon atoms, and substituted or unsubstituted heterocycloalkenylene group having 2 to 10 carbon atoms, $Ar_1$ and $Ar_2$ are the same or different, and each independently selected from the group consisting of a substituted or unsubstituted aryl group having 6 to 30 carbon atoms, a substituted or unsubstituted heteroaryl group having 3 to 30 carbon atoms, a substituted or unsubstituted alkyl group having 1 to 20 carbon atoms, a substituted or unsubstituted cycloalkyl group having 1 to 20 carbon atoms, a substituted or unsubstituted heteroalkyl group having 1 to 20 carbon atoms, a substituted or unsubstituted heterocycloalkyl group having 1 to 20 carbon atoms, a substituted or unsubstituted alkenyl group having 1 to 20 carbon atoms, a substituted or unsubstituted cycloalkenyl group having 1 to 20 carbon atoms and a substituted or unsubstituted heteroalkenyl group having 1 to 20 carbon atoms, and the substituents $R_1$ to $R_2$, A, L and $Ar_1$ to $Ar_2$ are the same or different, and each independently selected from the group consisting of deuterium, a cyano group, a nitro group, a halogen group, a hydroxyl group, a substituted or unsubstituted alkyl group having 1 to 30 carbon atoms, a substituted or unsubstituted cycloalkyl group having 1 to 20 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, a substituted or unsubstituted heteroarylalkyl group having 3 to 30 carbon atoms, a substituted or unsubstituted alkoxy group having 1 to 30 carbon atoms, a substituted or unsubstituted alkylsilyl group having 1 to 30 carbon atoms, a substituted or unsubstituted arylsilyl group having 6 to 30 carbon atoms, and a substituted or unsubstituted aryloxy group having 6 to 30 carbon atoms.

2. The compound of claim 1, wherein the compound represented by Formula 1 is represented by Formula 4 or 5 below:

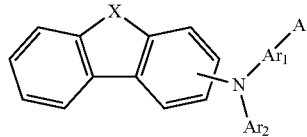

[Formula 4]

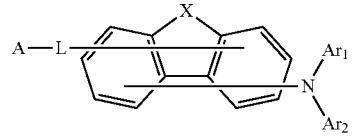

[Formula 5]

wherein each of X, A, L, $Ar_1$ and $Ar_2$ is the same as defined in Formula 1.

3. The compound of claim 1, wherein X is $C(R_1)(R_2)$.

4. The compound of claim 1, wherein $Ar_1$ and $Ar_2$ are a substituted or unsubstituted aryl group having 6 to 30 carbon atoms or a substituted or unsubstituted heteroaryl group having 3 to 30 carbon atoms.

5. The compound of claim 1, wherein $R_1$ and $R_2$ are a substituted or unsubstituted alkyl group having 1 to 30 carbon atoms, a substituted or unsubstituted cycloalkyl group having 1 to 20 carbon atoms or a substituted or unsubstituted aryl group having 6 to 30 carbon atoms.

6. The compound of claim 1, wherein L is selected from the group consisting of a single bond, a substituted or unsubstituted arylene group having 6 to 30 carbon atoms and a substituted or unsubstituted heteroarylene group having 6 to 30 nuclear carbon atoms.

7. The compound of claim 1, wherein the compound represented by Formula 1 is selected from the group consisting of the following compounds:

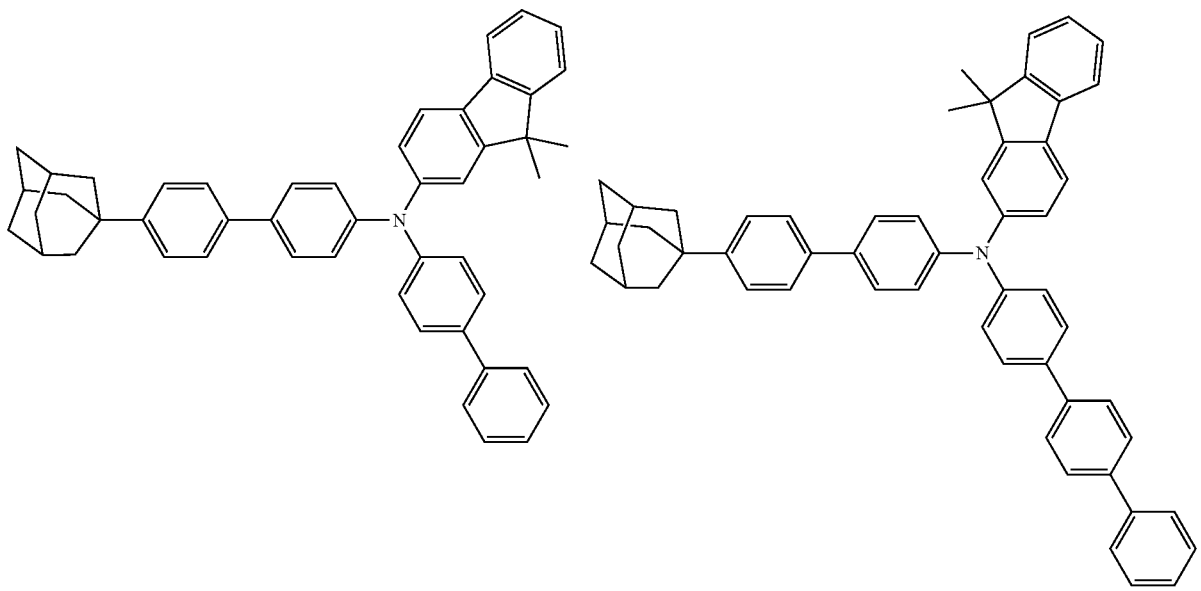

-continued
75
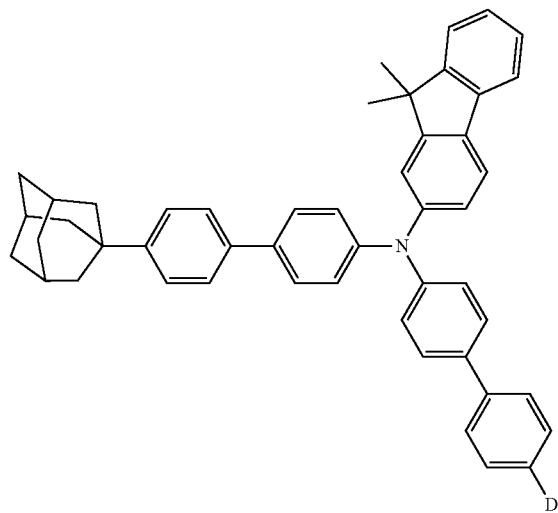
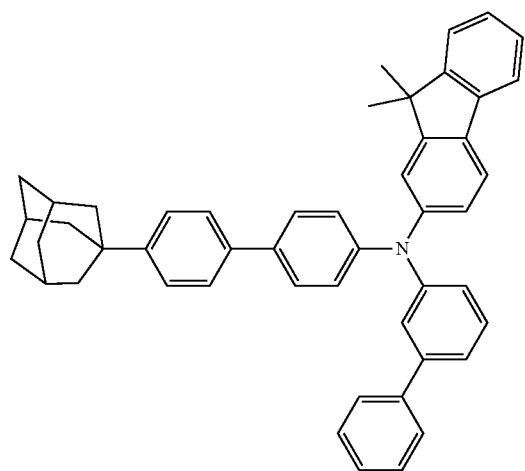
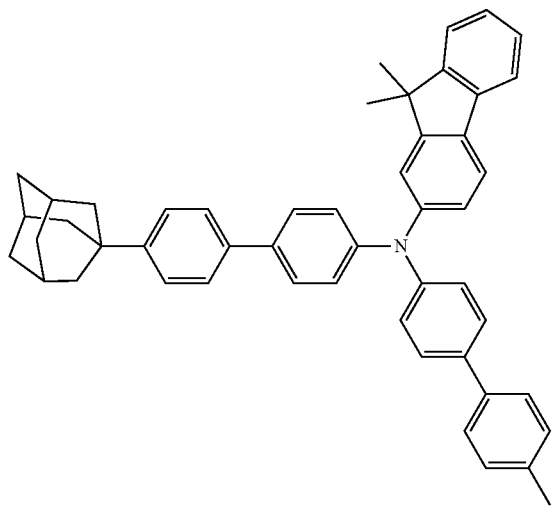
76
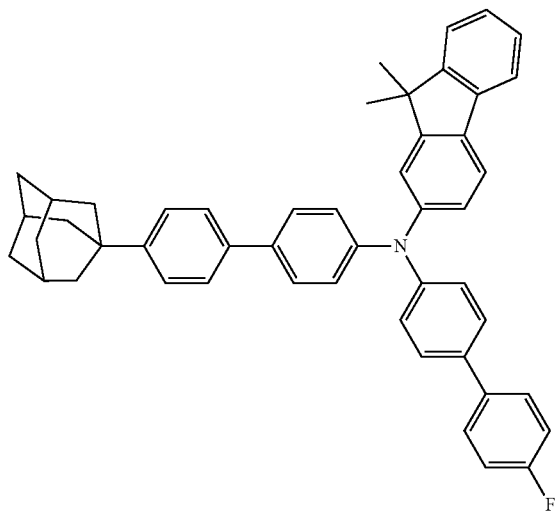
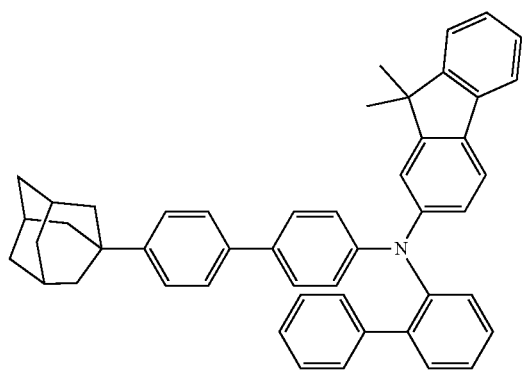
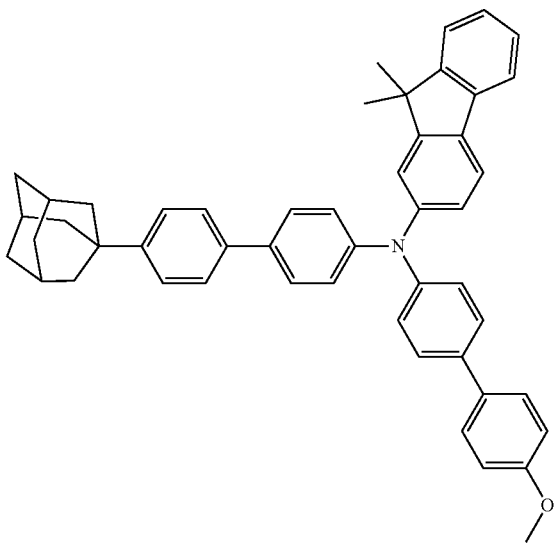

-continued
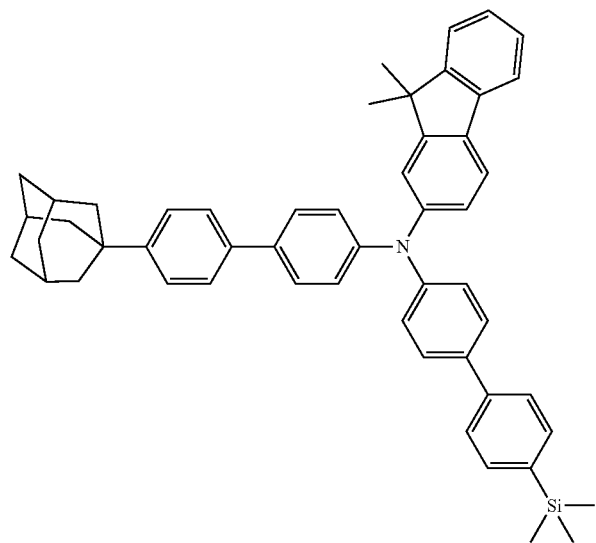
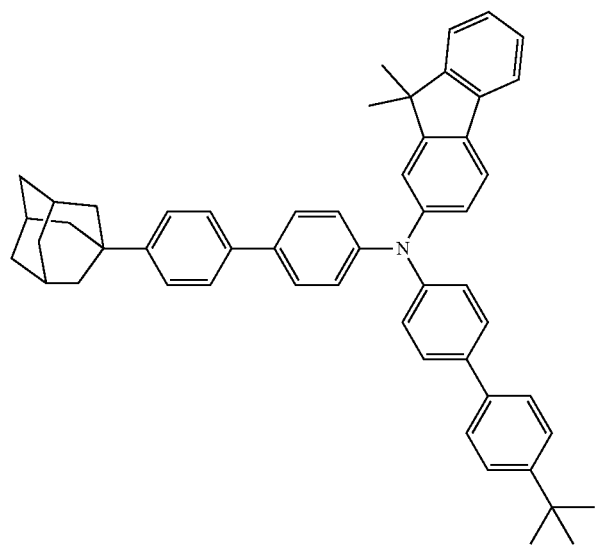
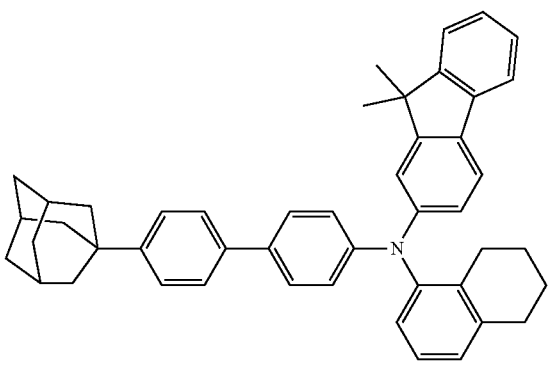
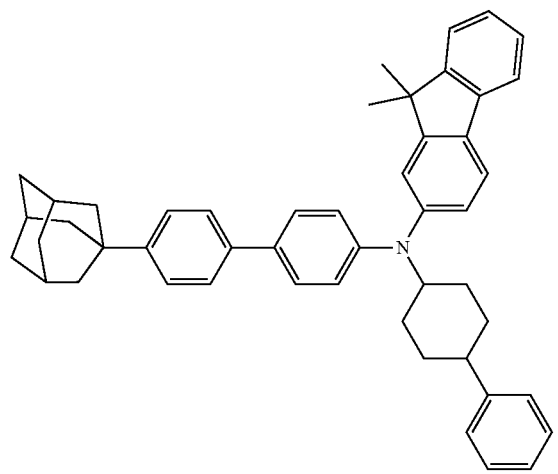
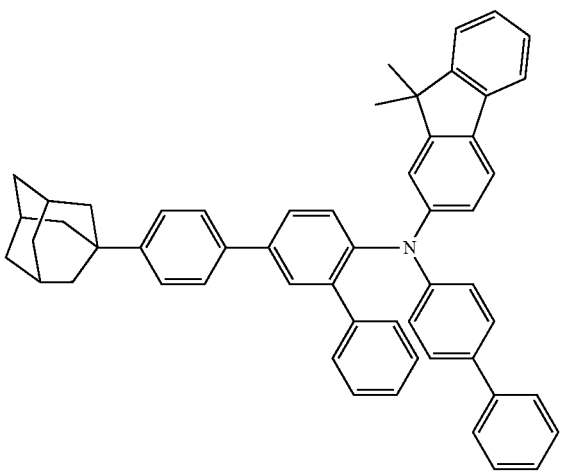

-continued
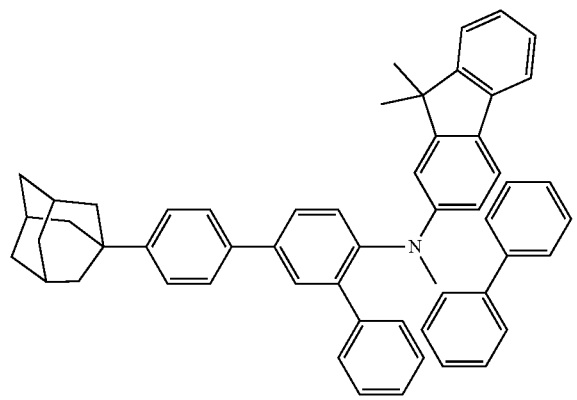
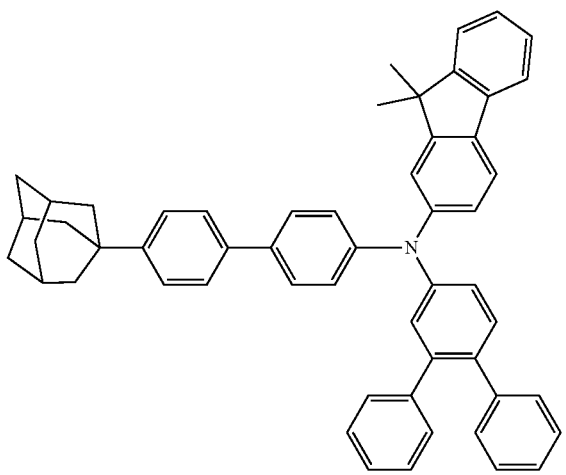
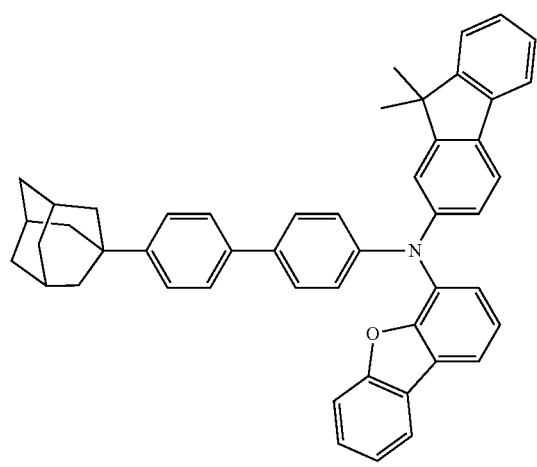
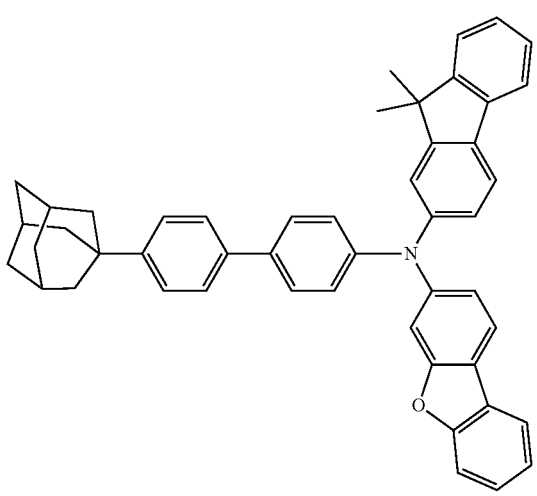
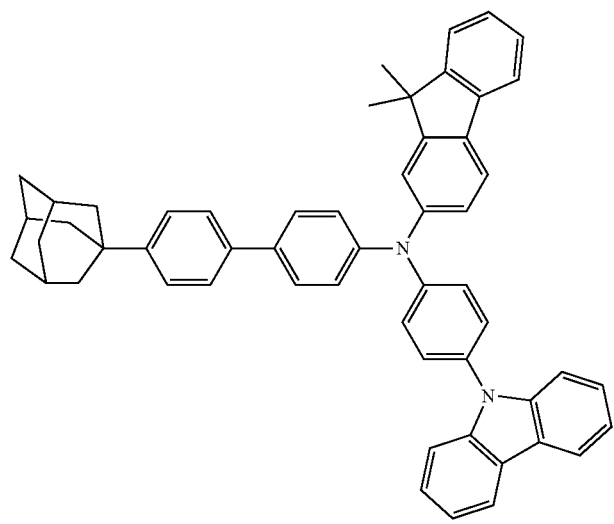

-continued
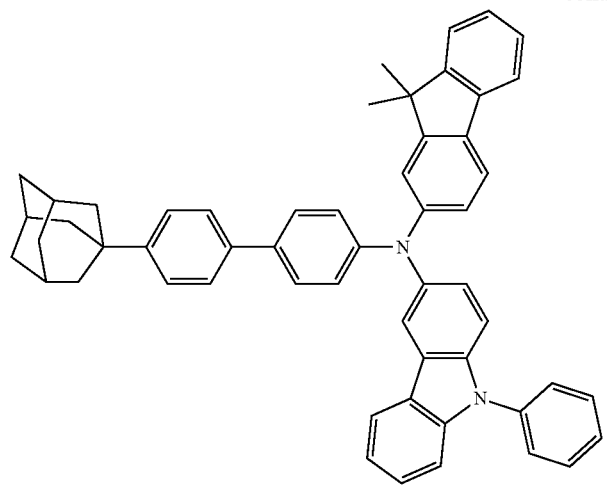
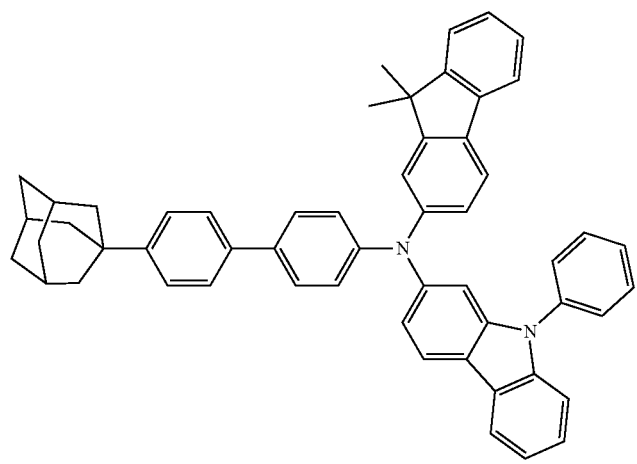
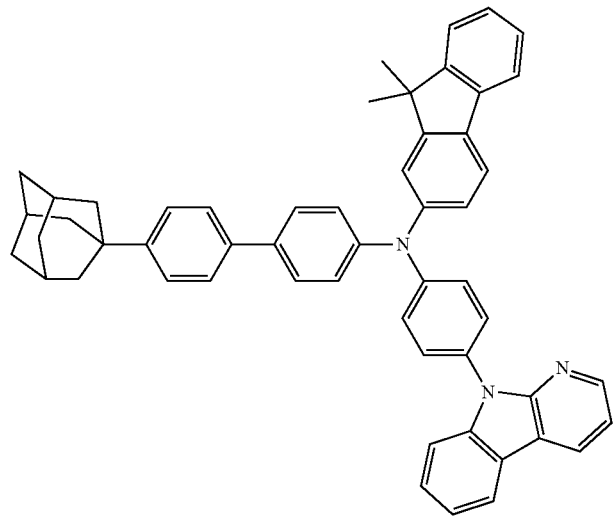
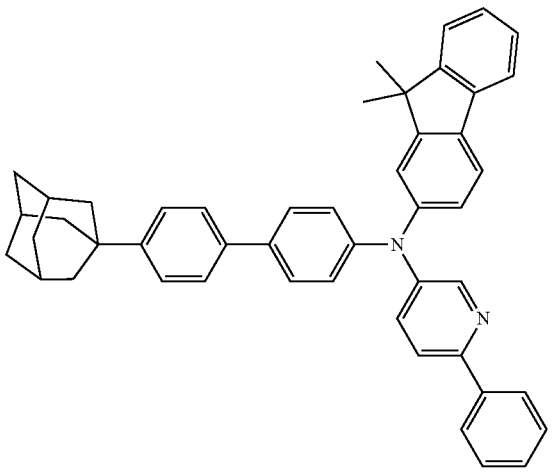

83
84
-continued
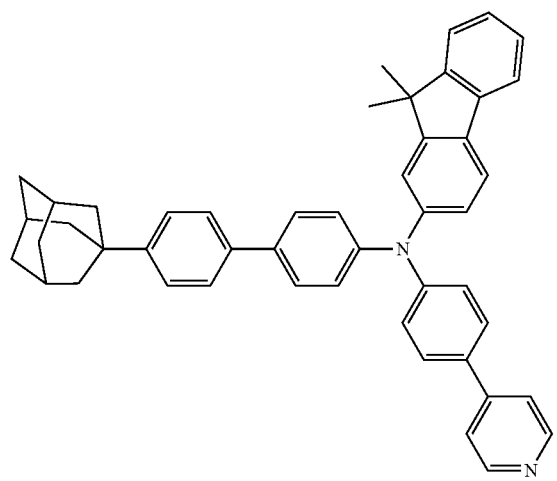
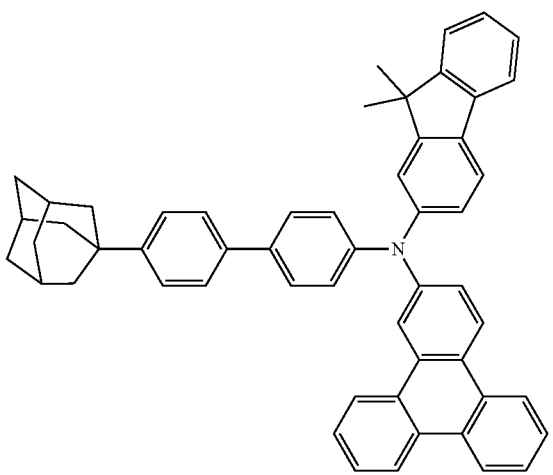
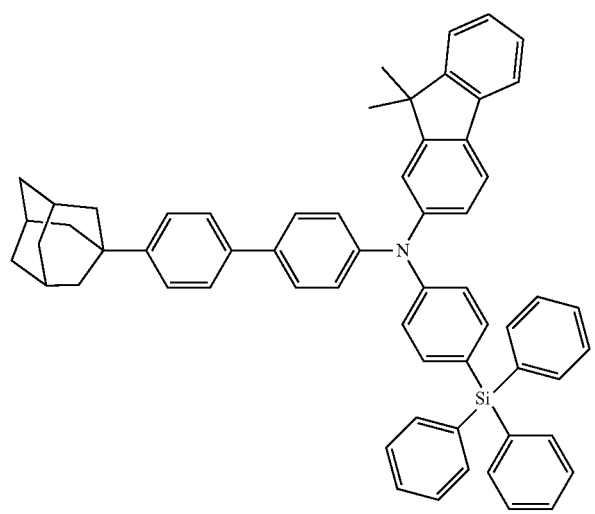
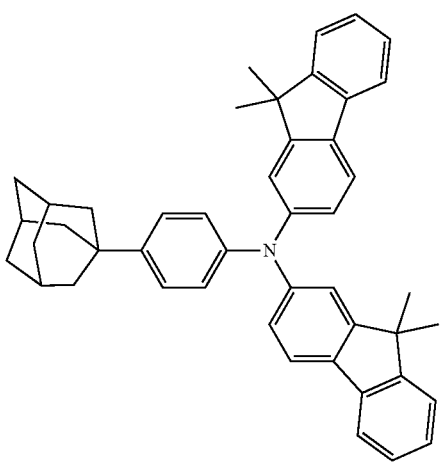
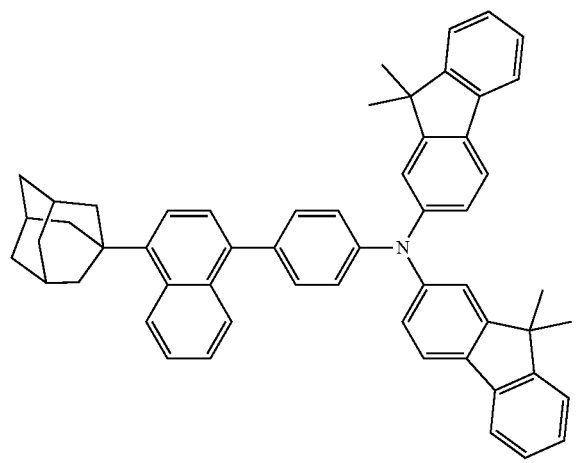

-continued
85
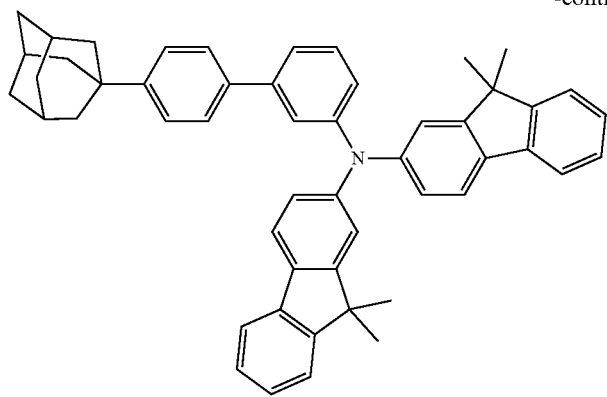
86
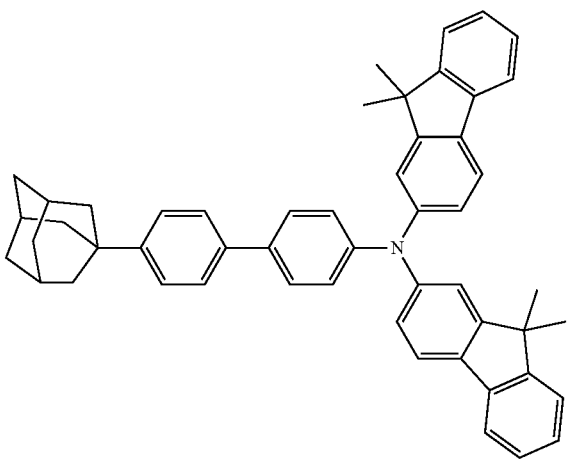
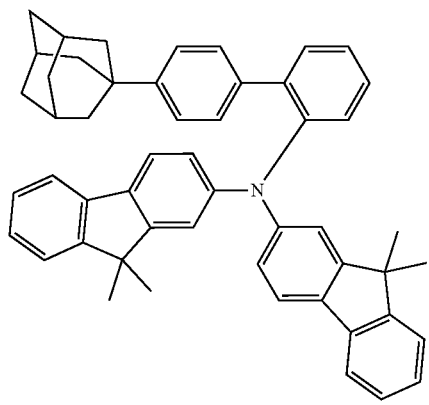
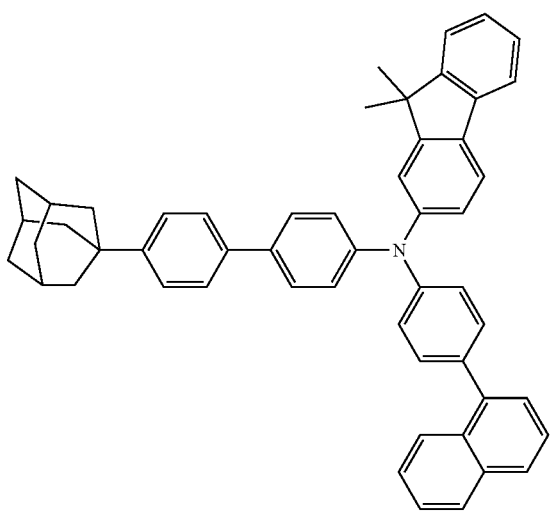
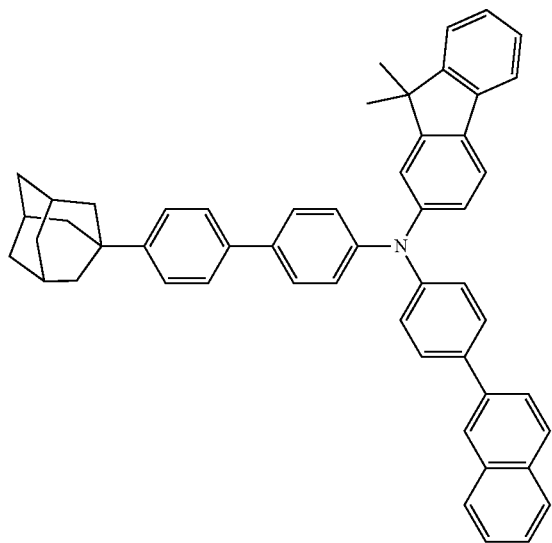
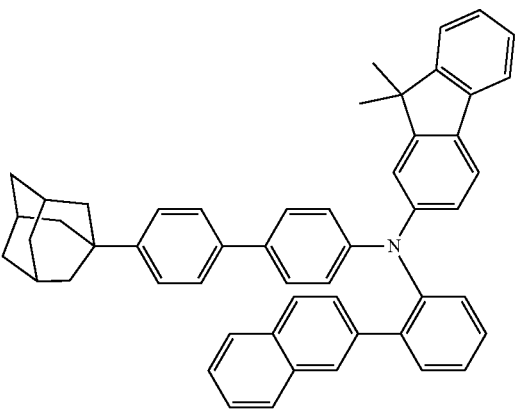

87
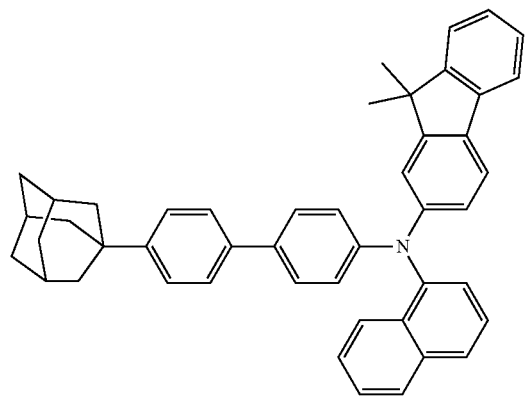
88
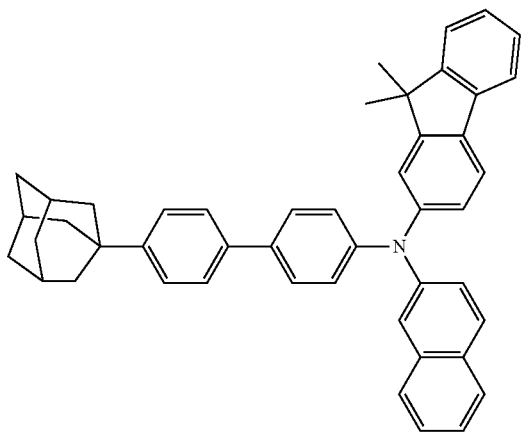
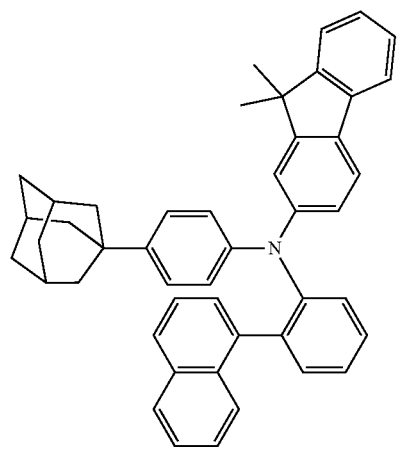
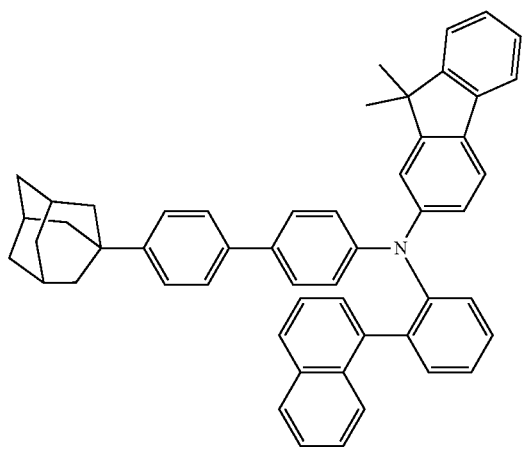
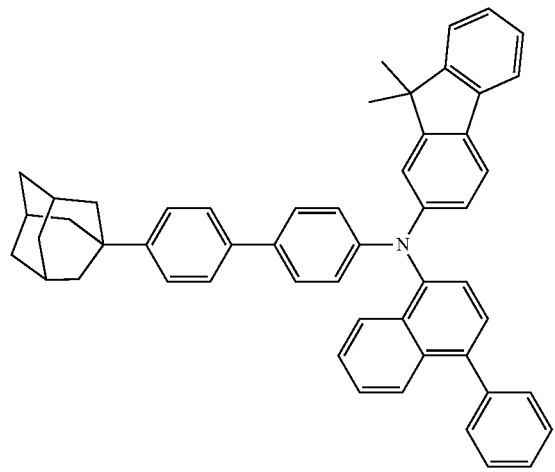
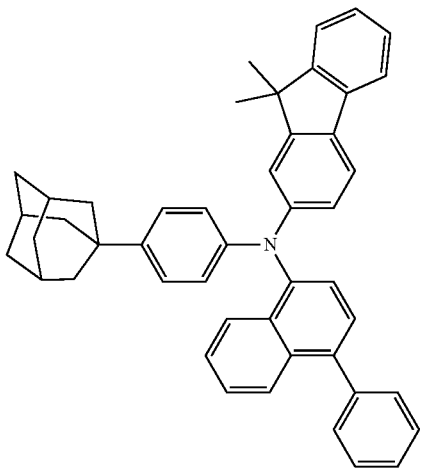

-continued
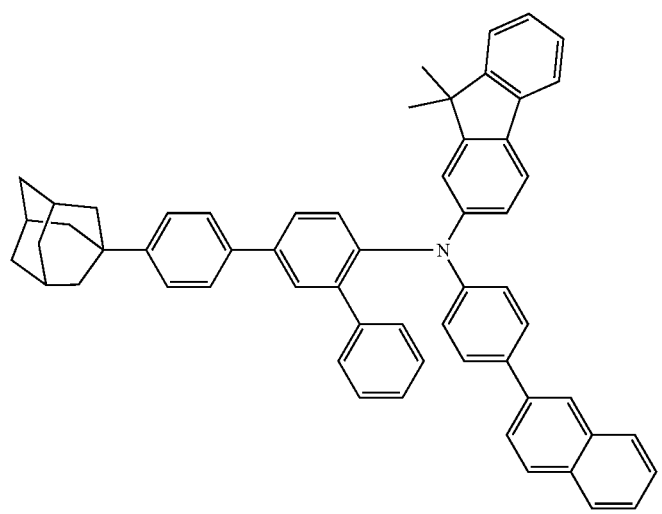
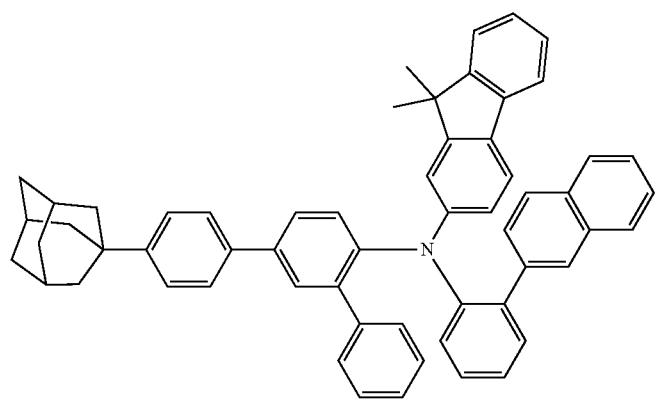
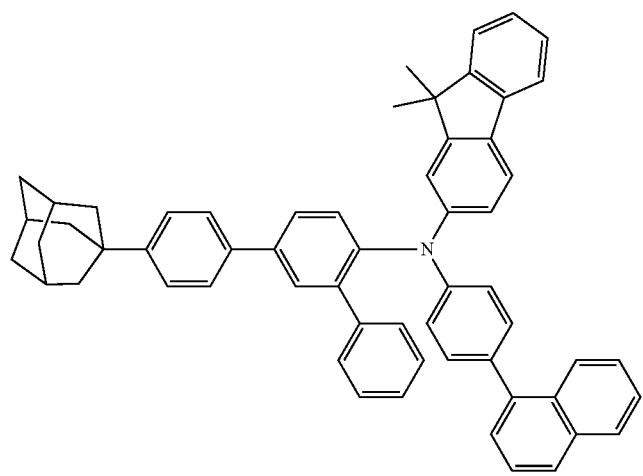

-continued
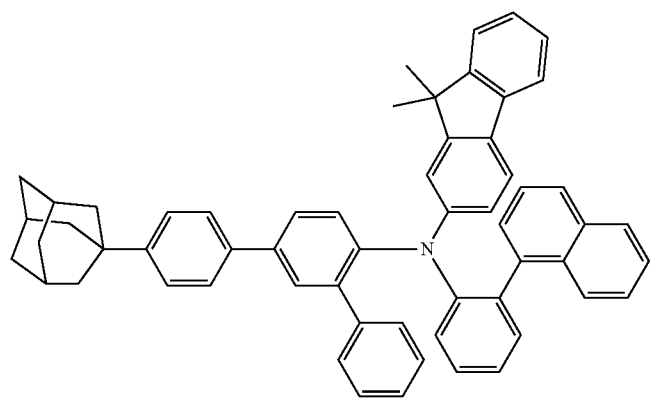
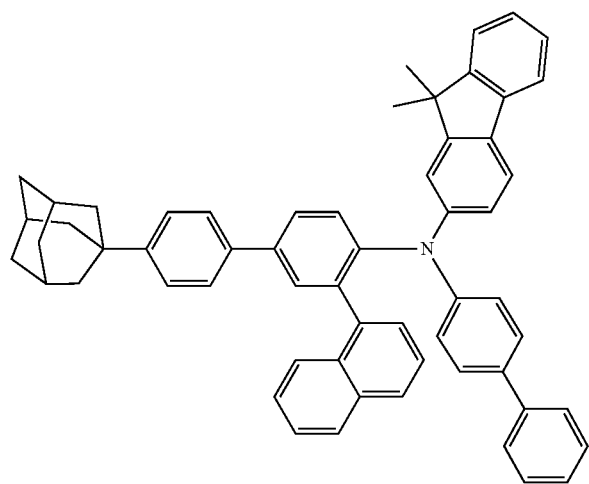
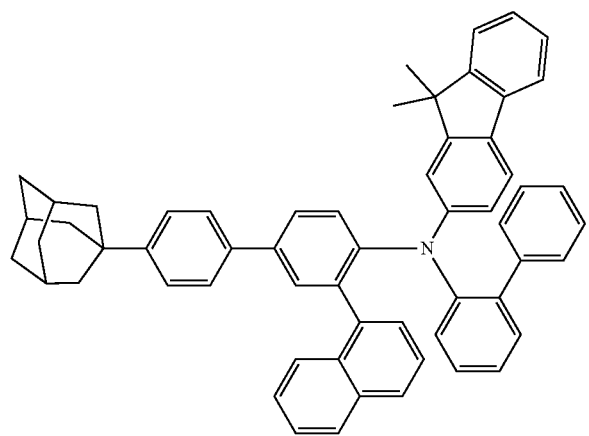

-continued
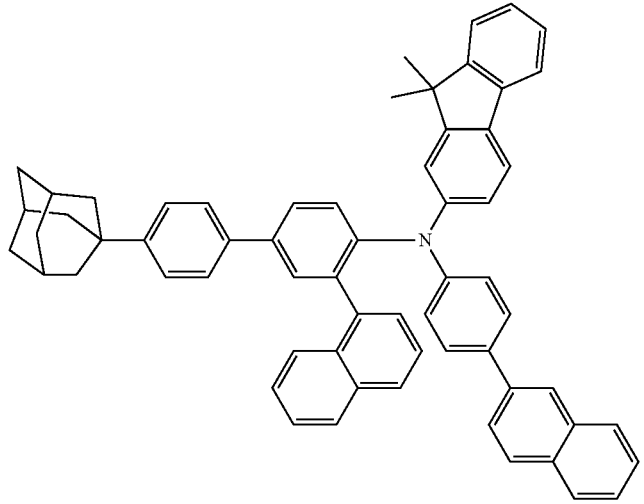
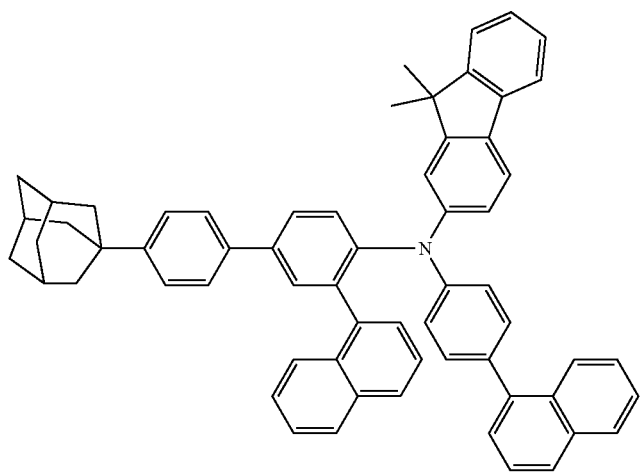
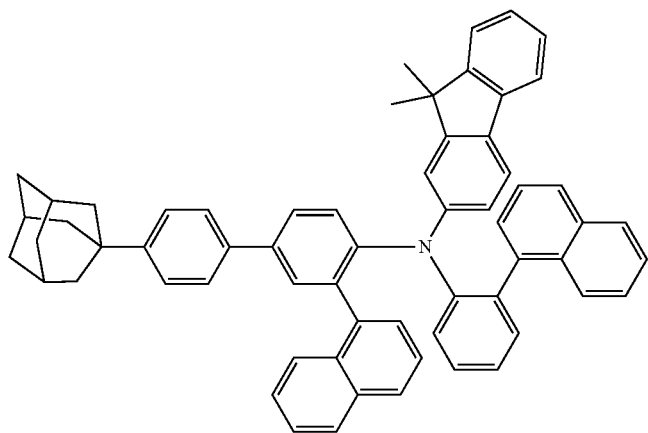

-continued
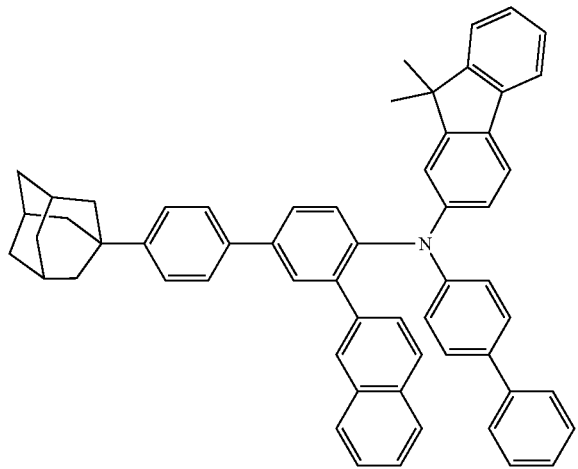
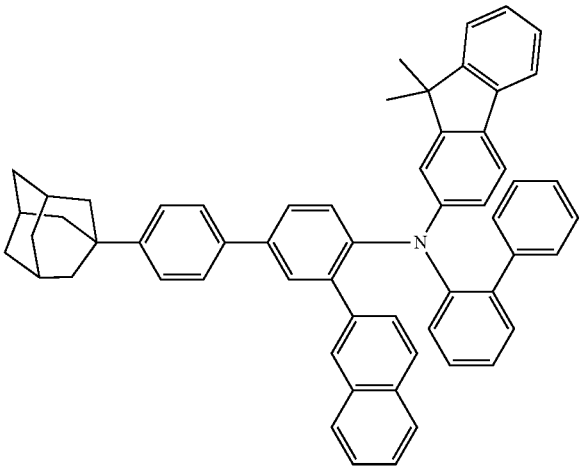
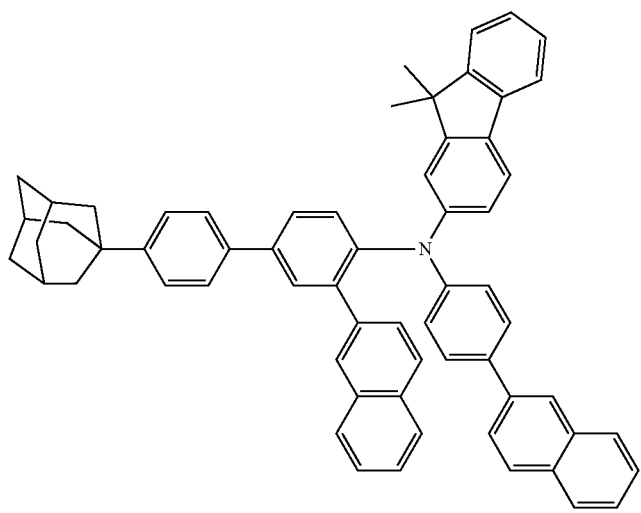
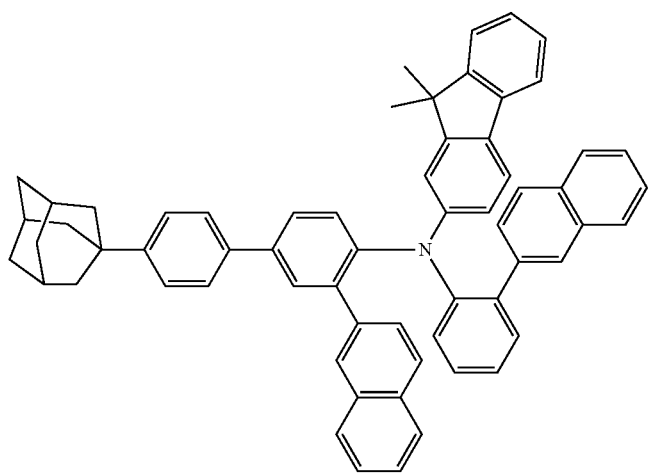

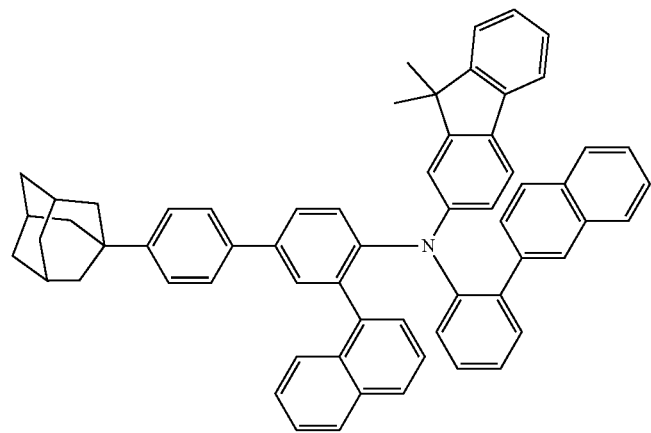
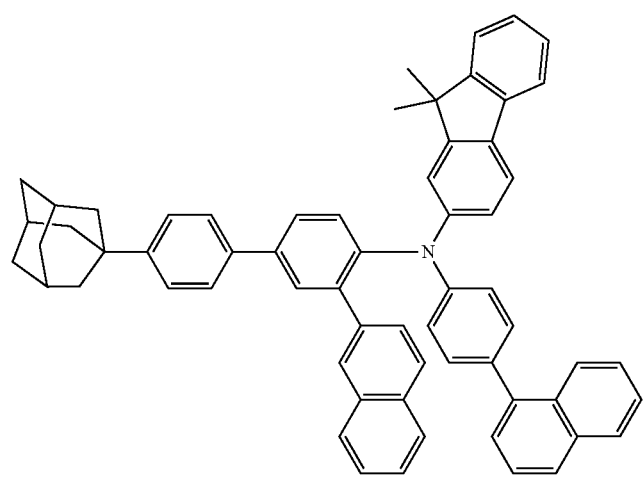
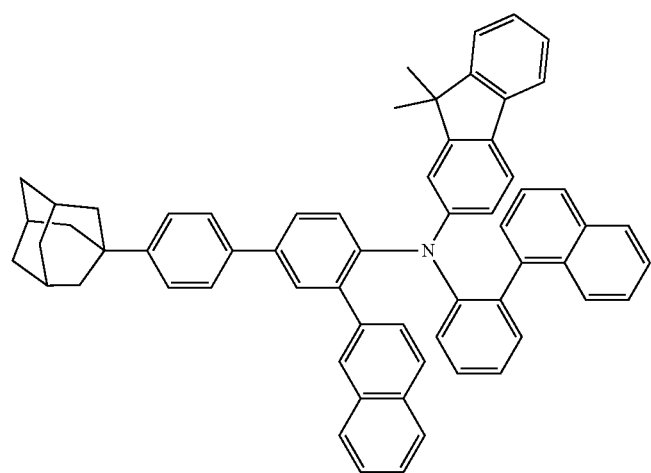
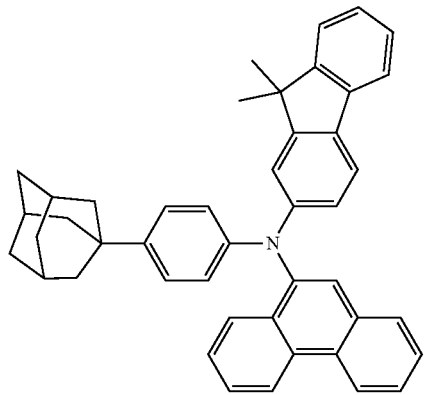

99
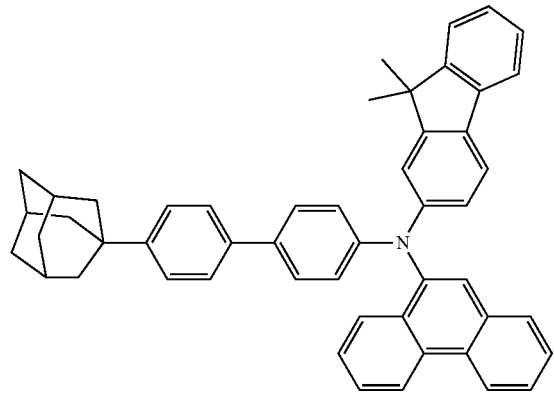
100
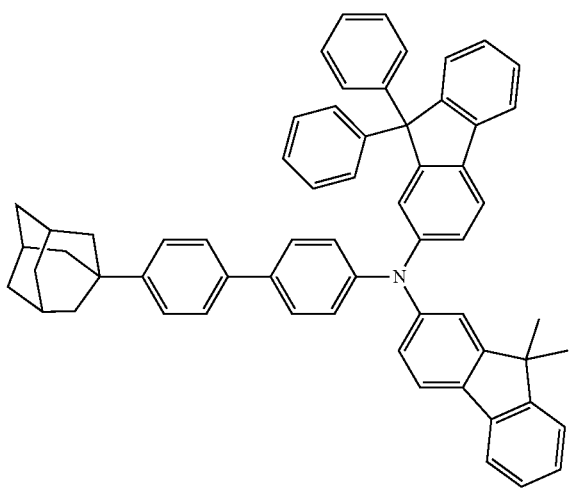
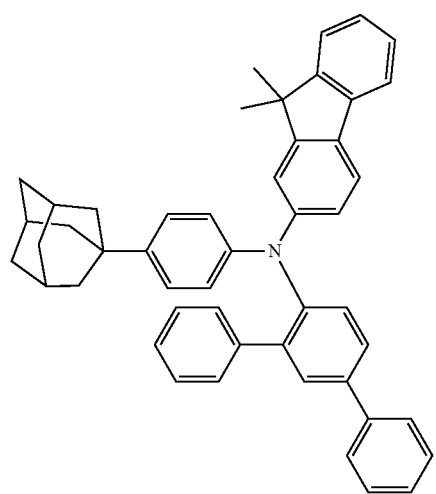
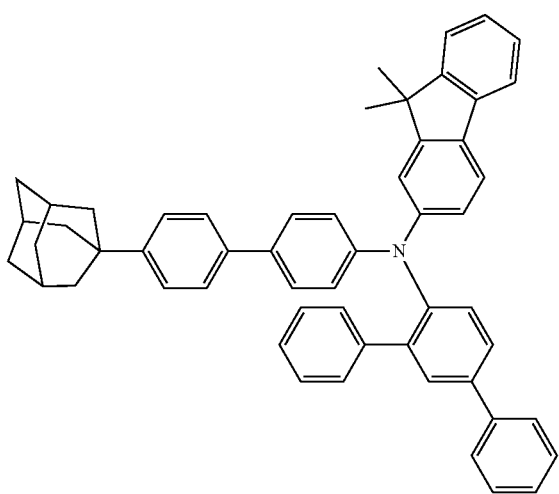
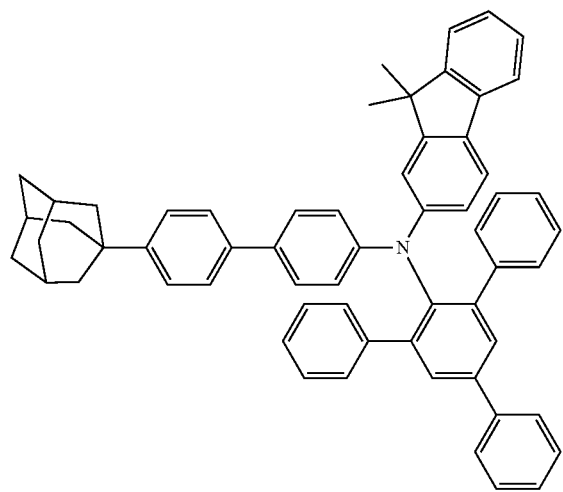

101
-continued
102
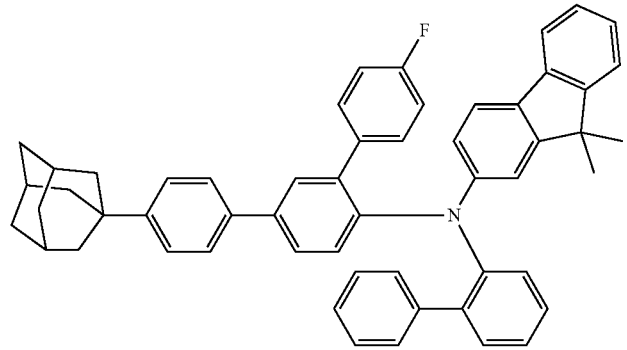
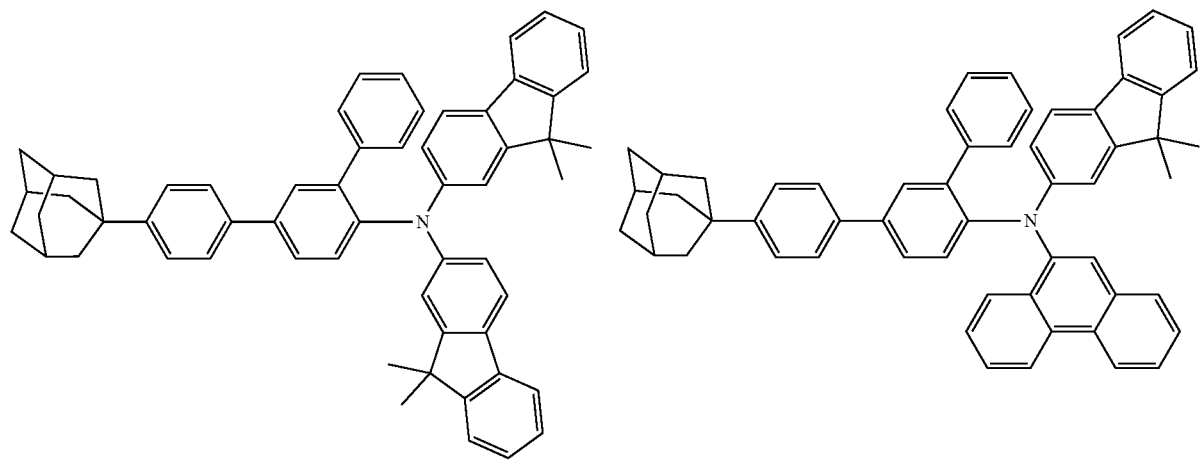
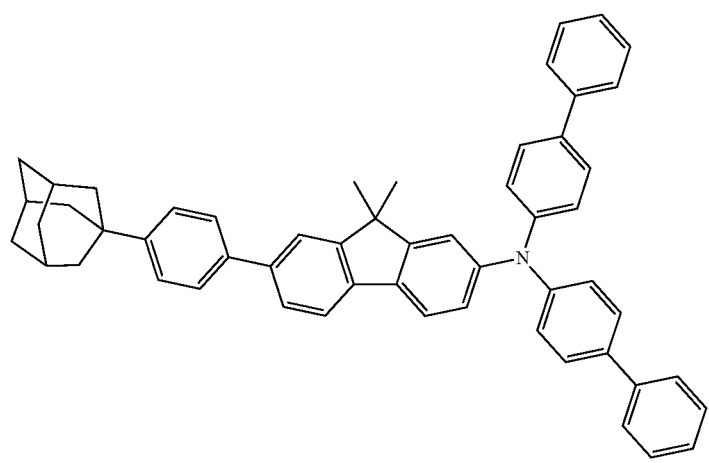
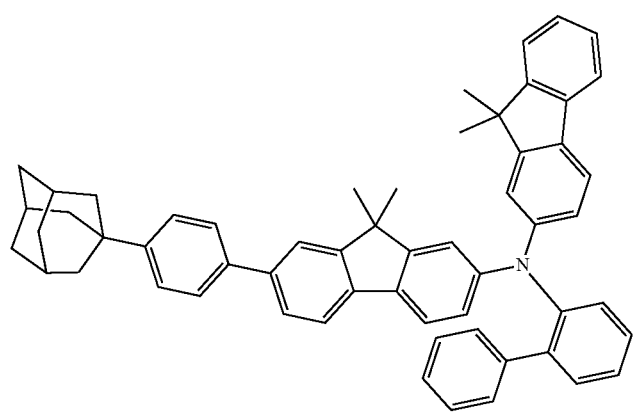

-continued
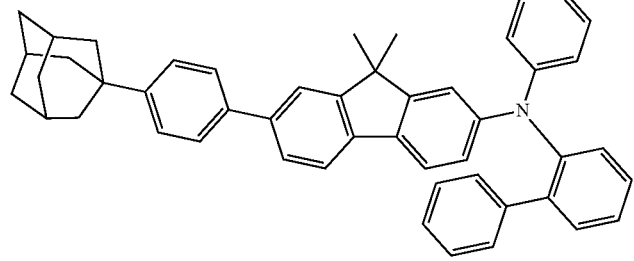
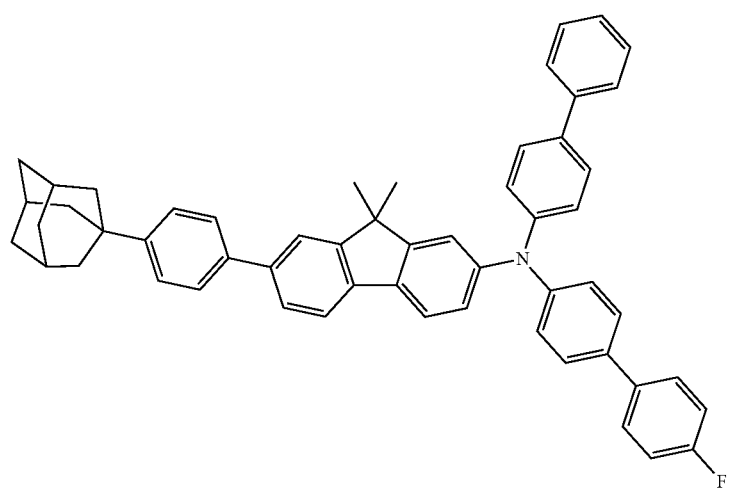
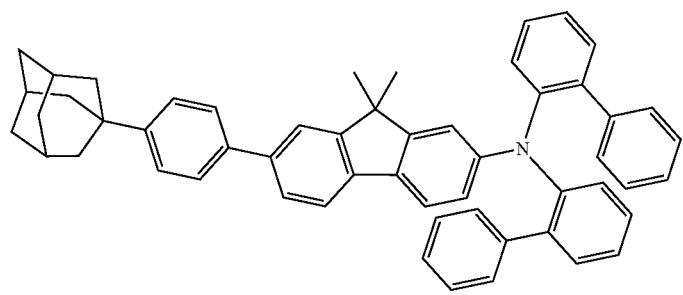
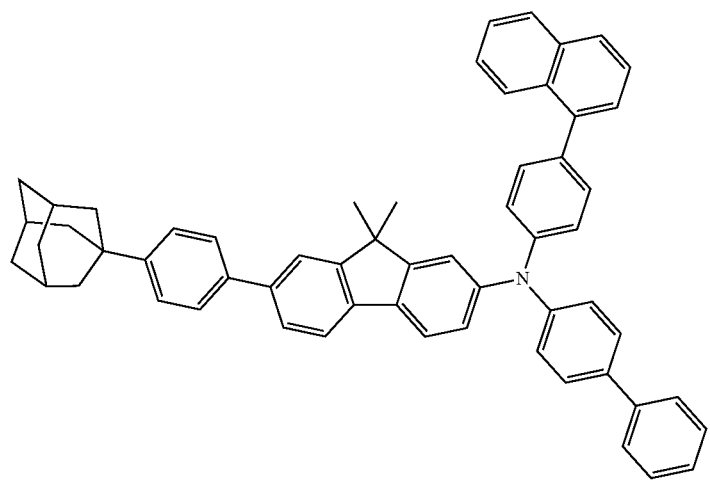

-continued
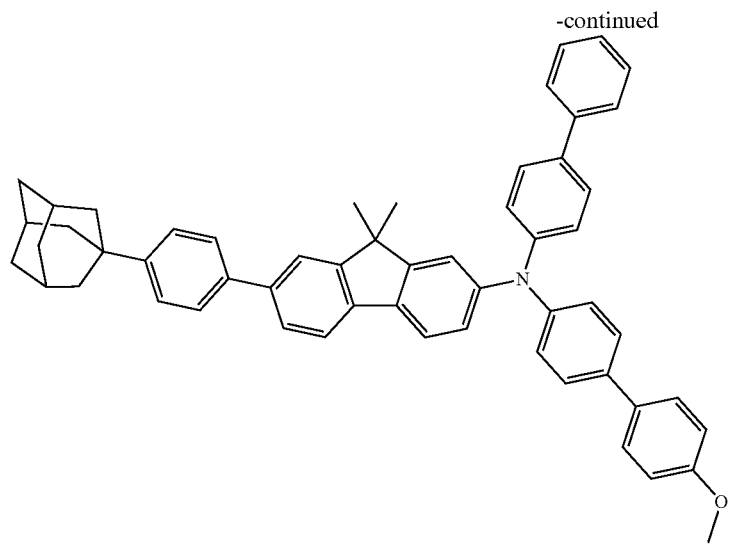
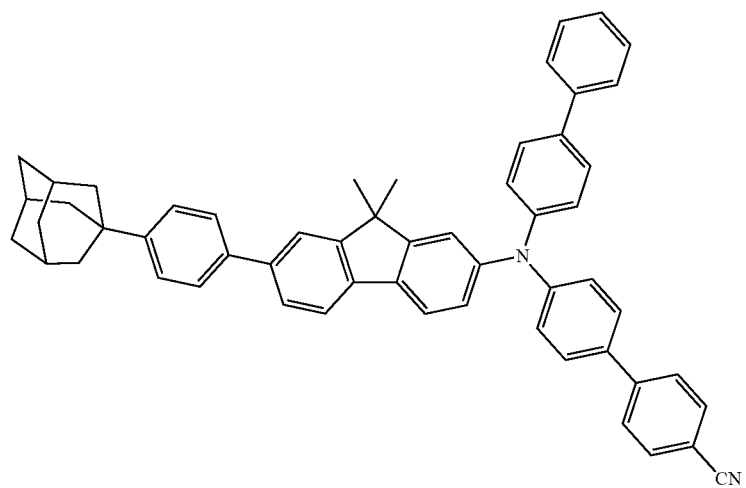
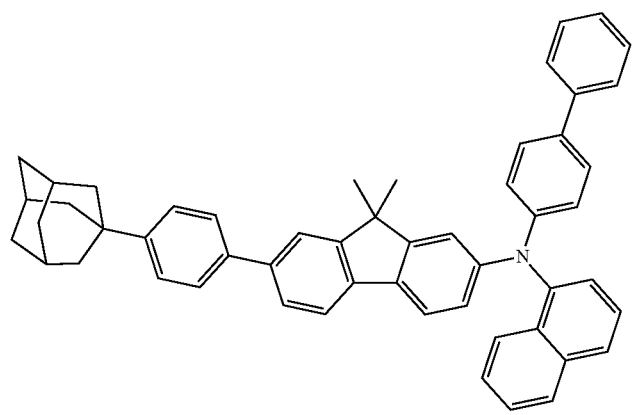

-continued
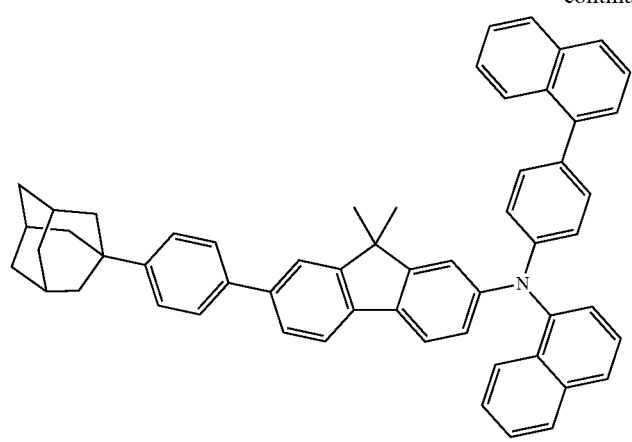
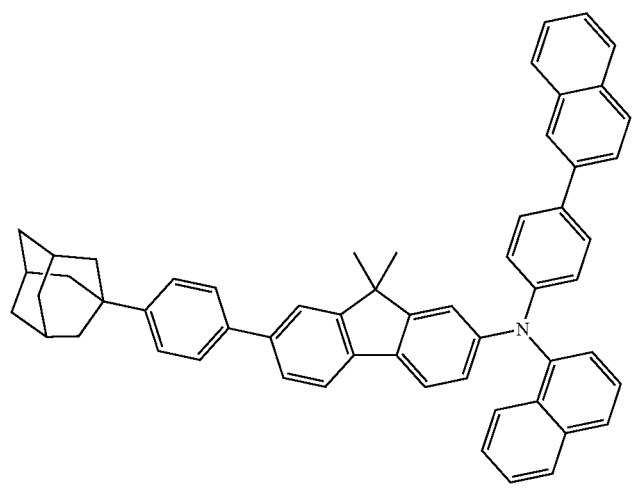
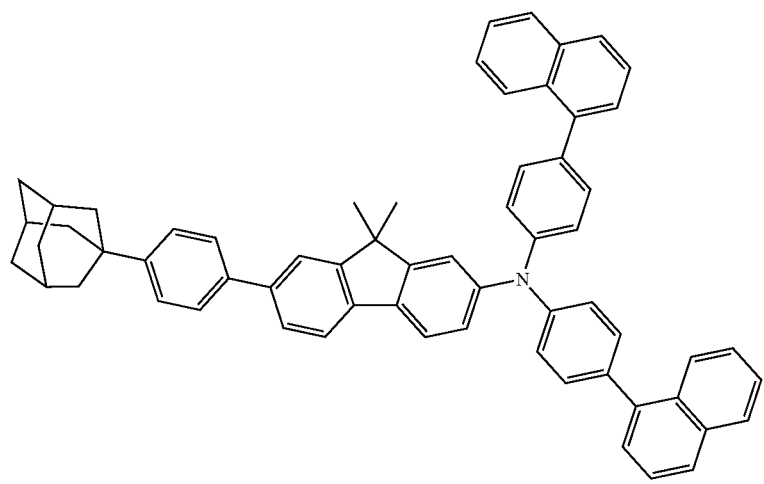

-continued
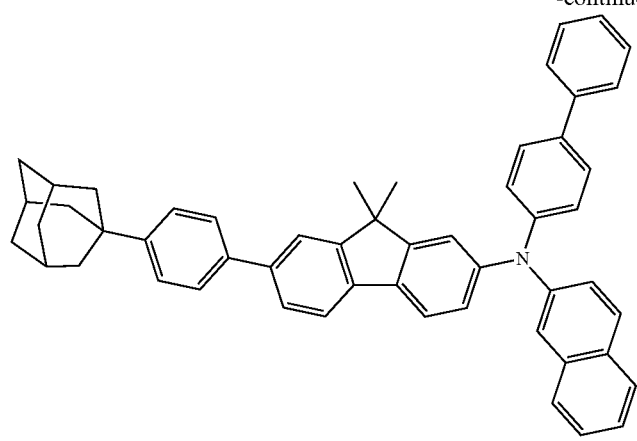
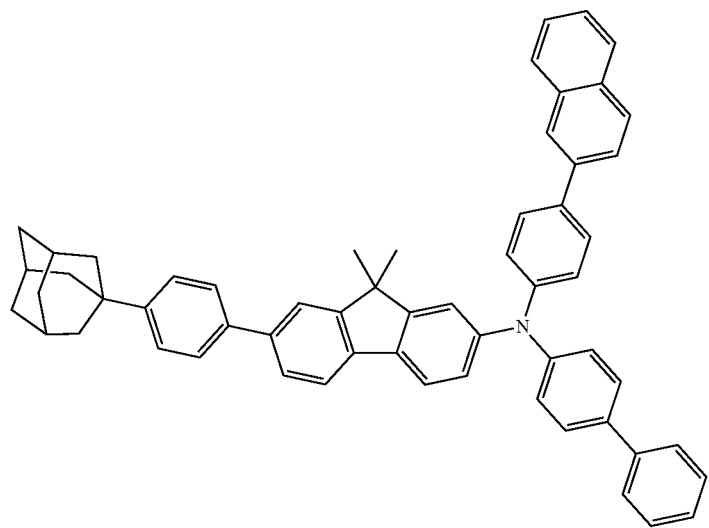
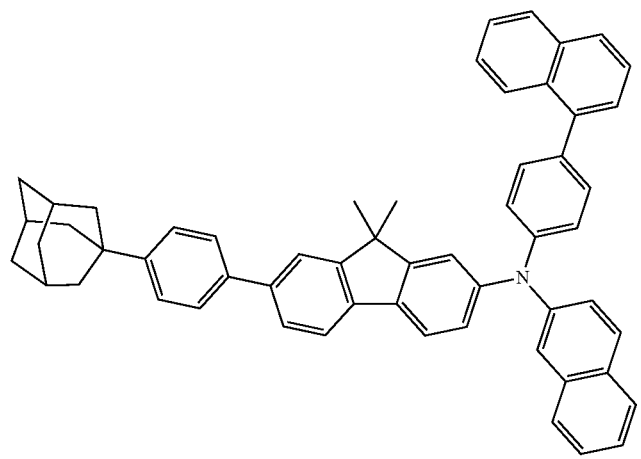

-continued
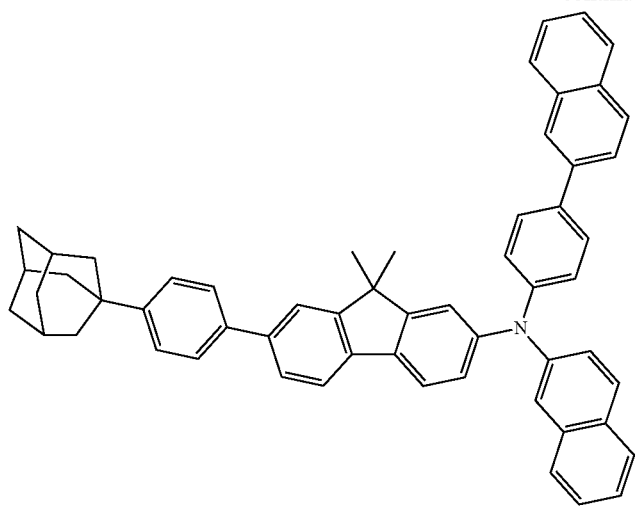
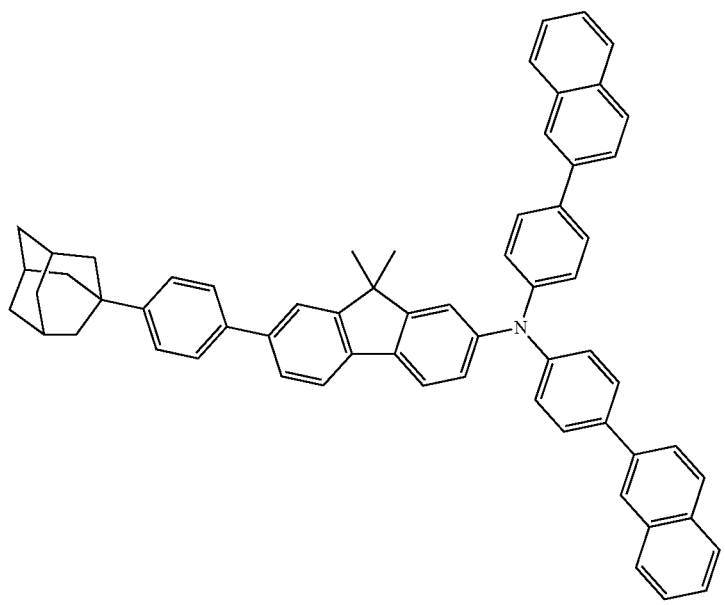
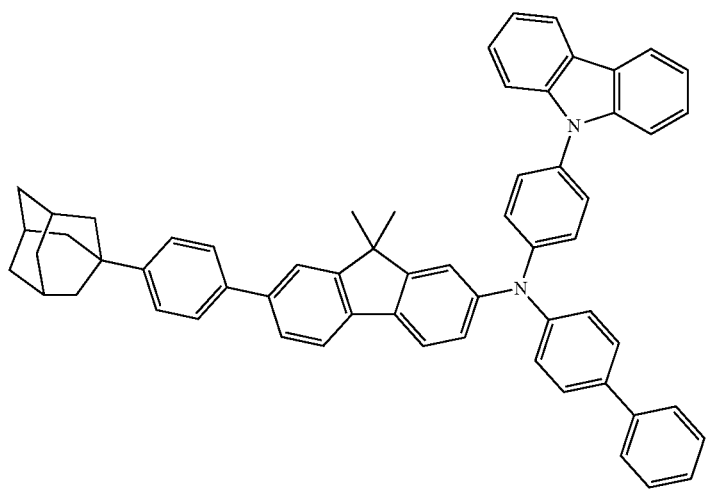

-continued
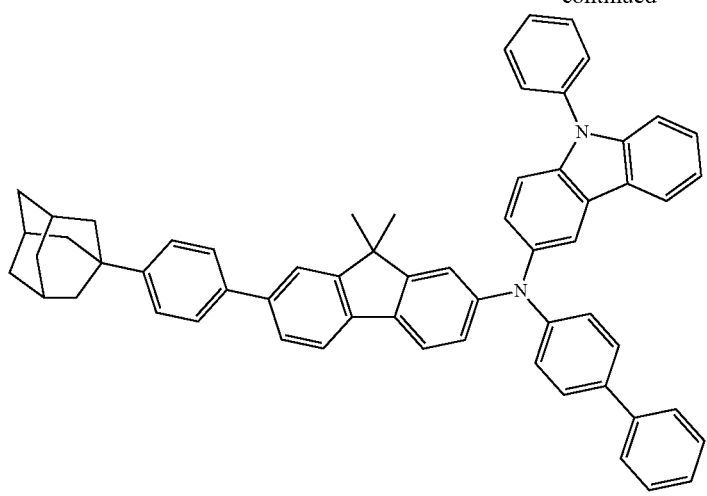
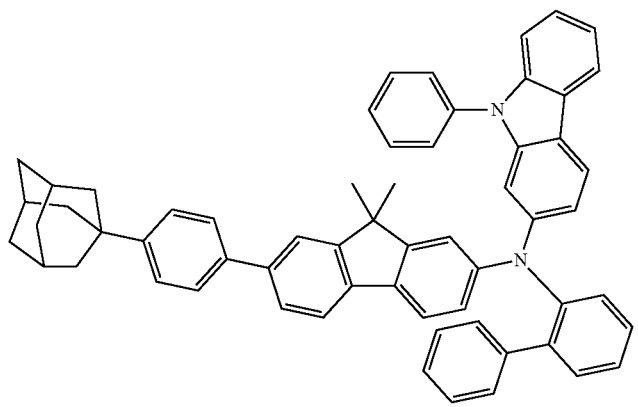
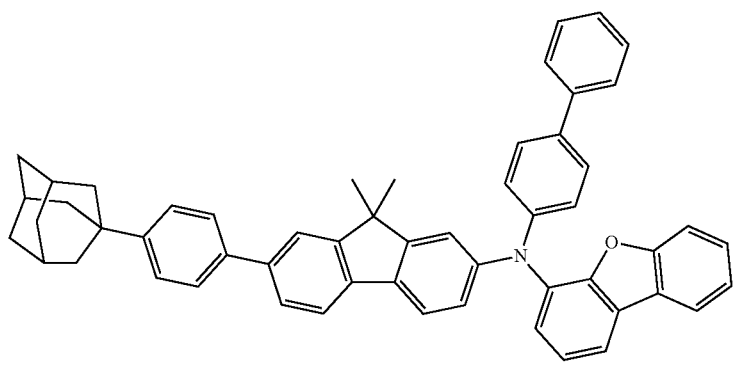
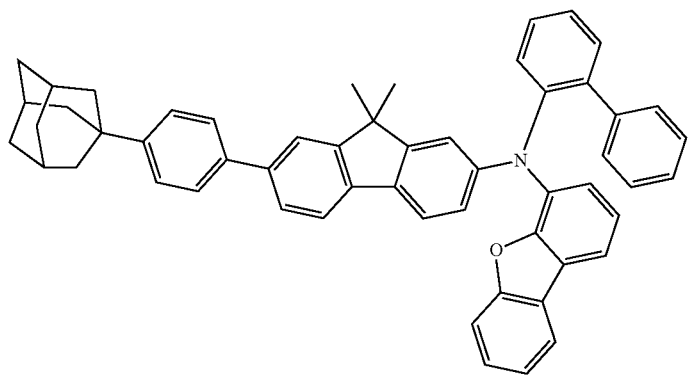

-continued
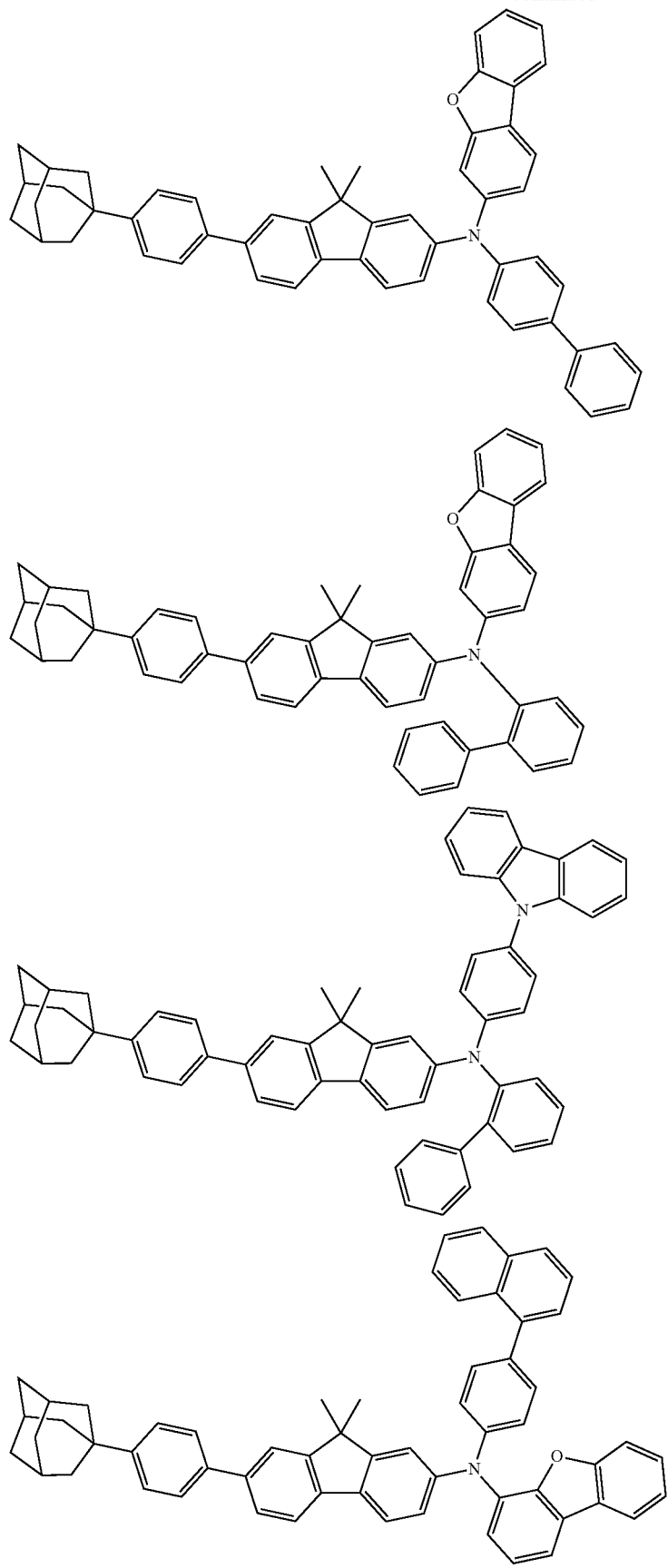

-continued
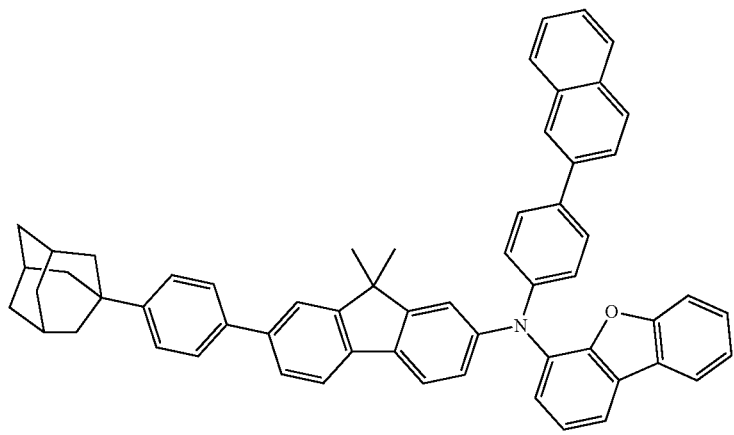
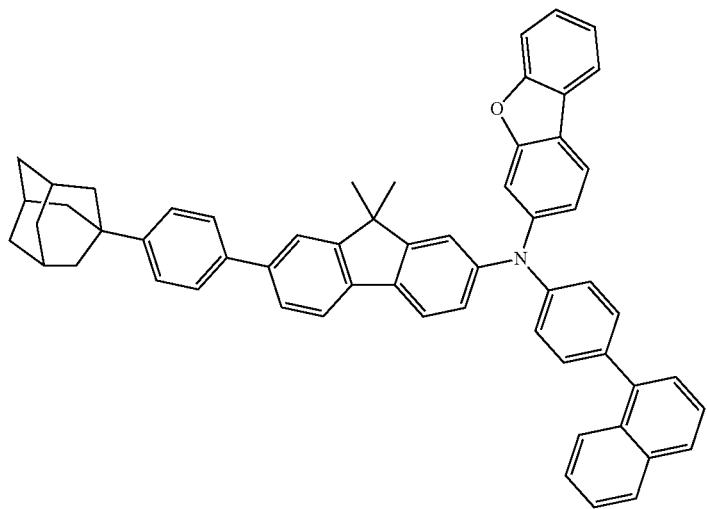
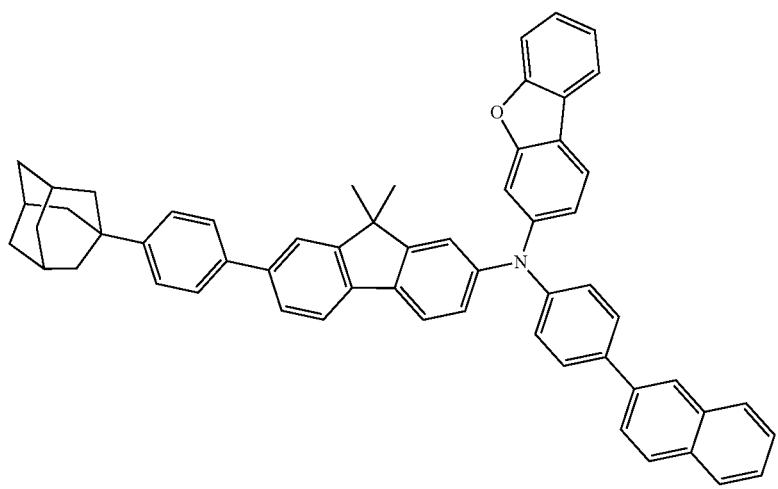

-continued
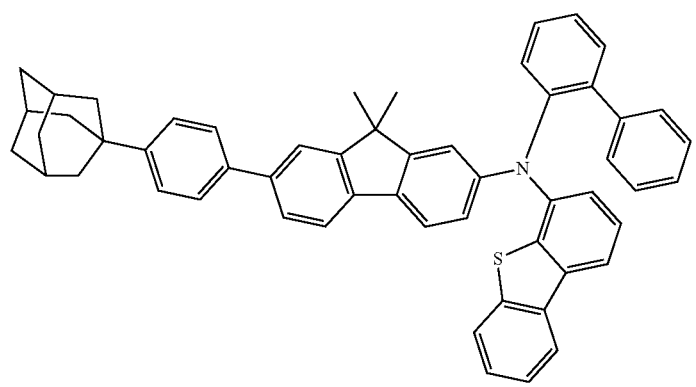
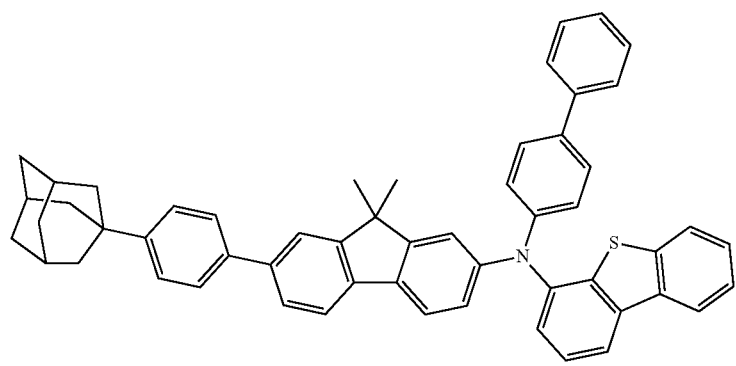
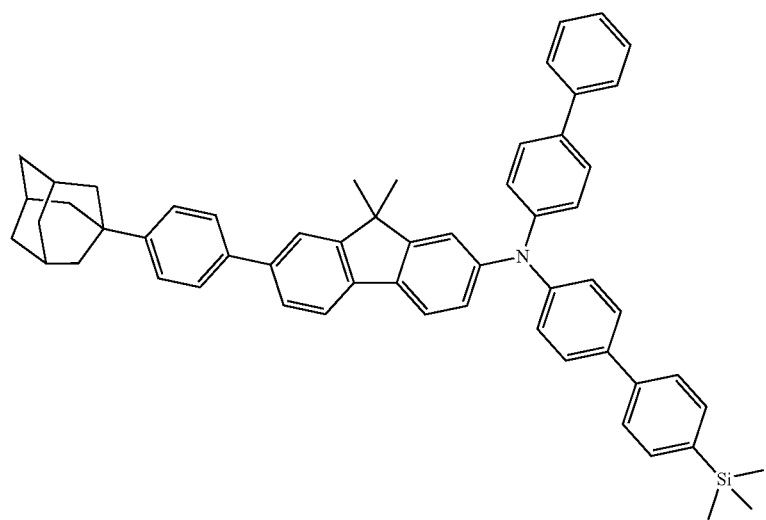

-continued
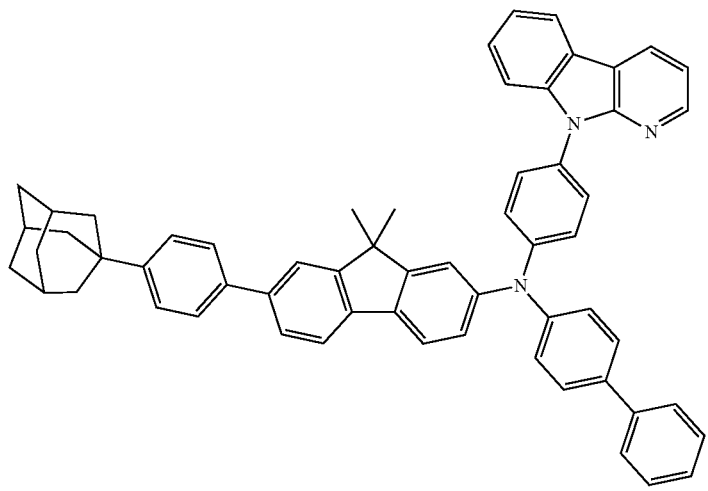
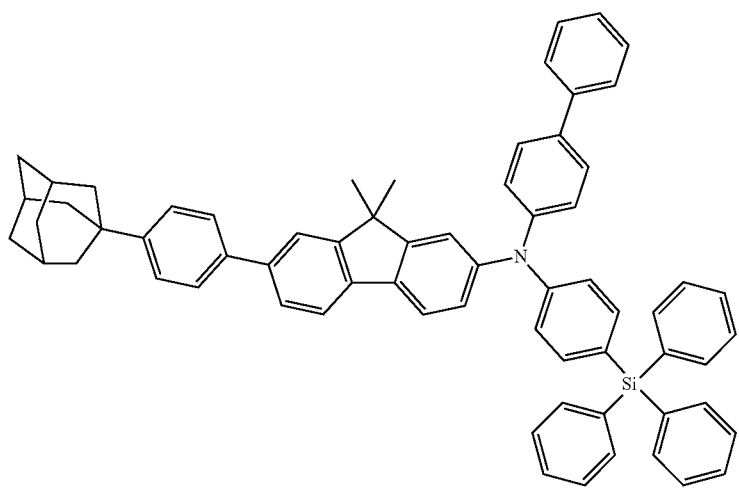
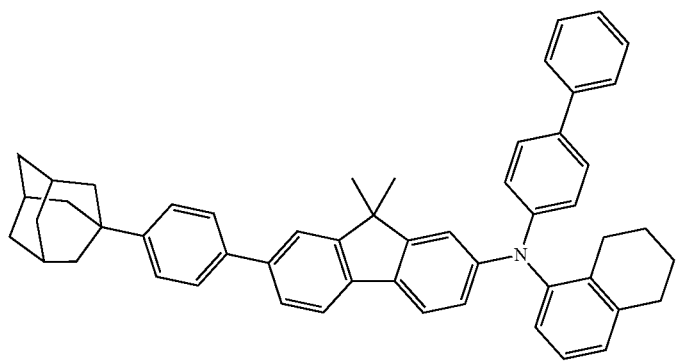

-continued
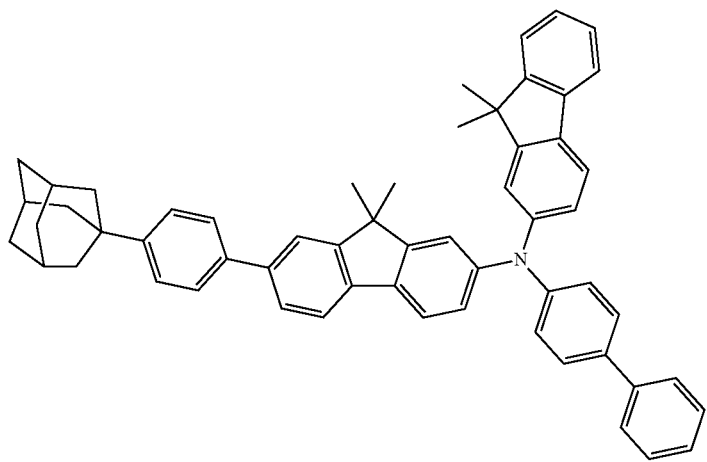
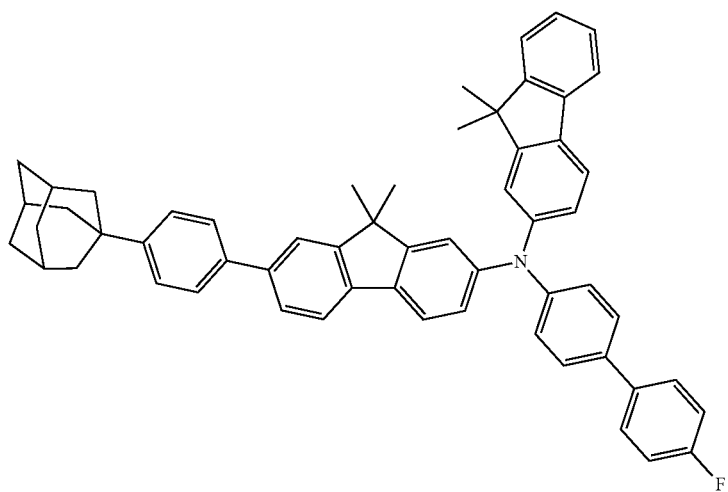
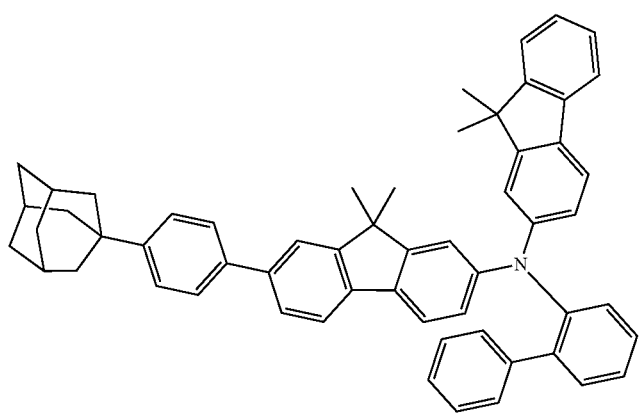

-continued
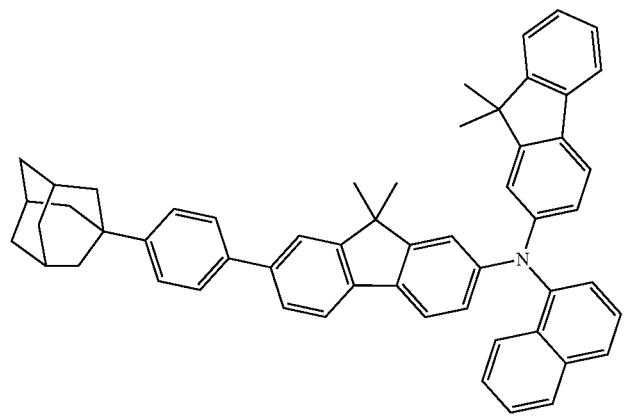
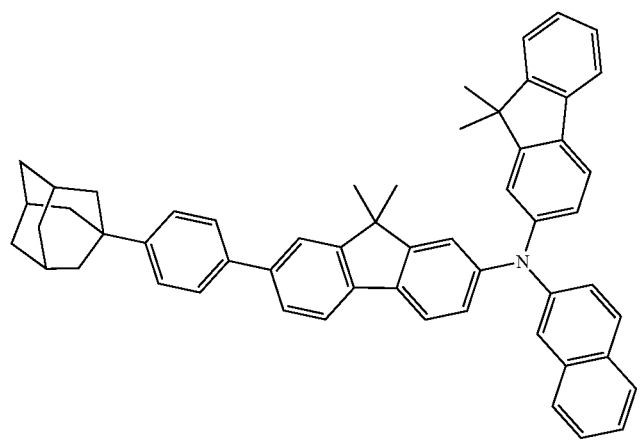
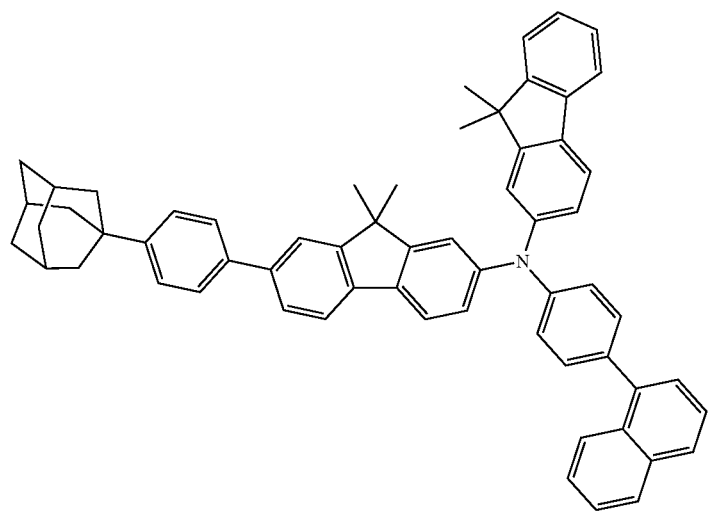

-continued
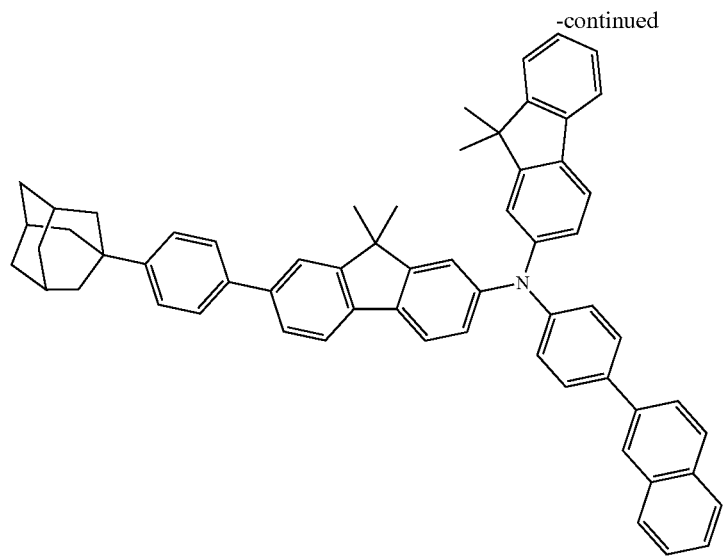
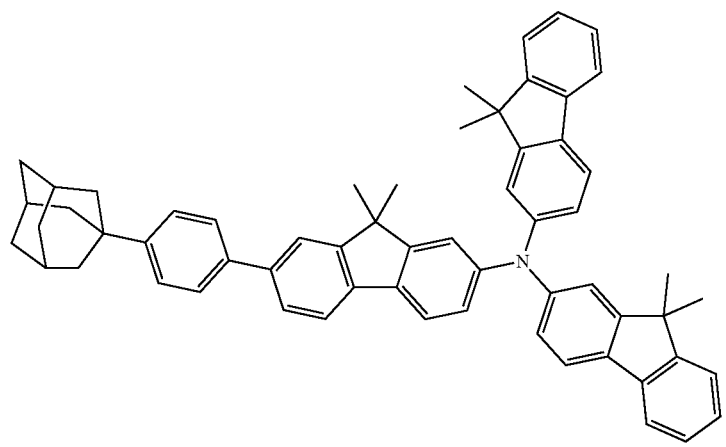
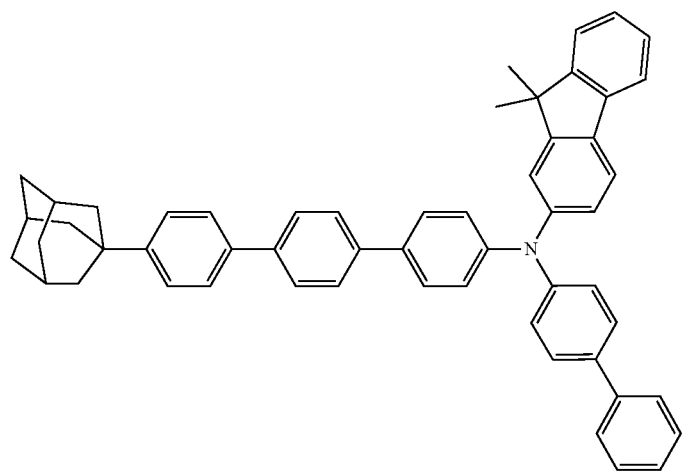

-continued
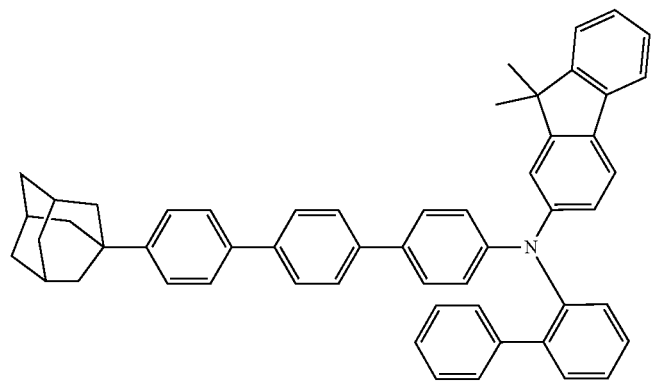
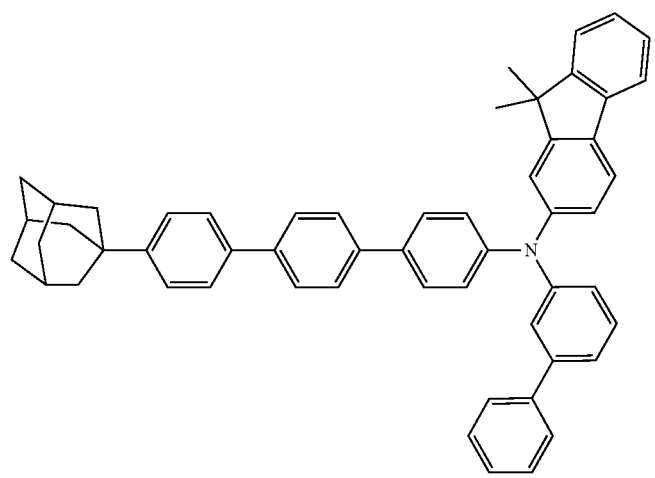
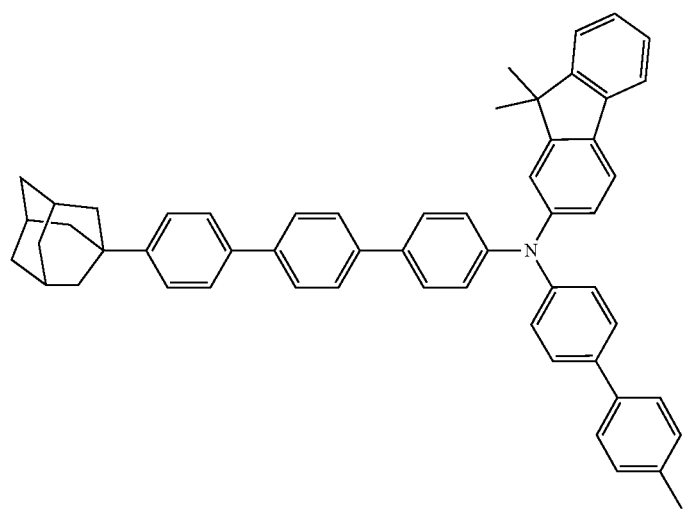

-continued
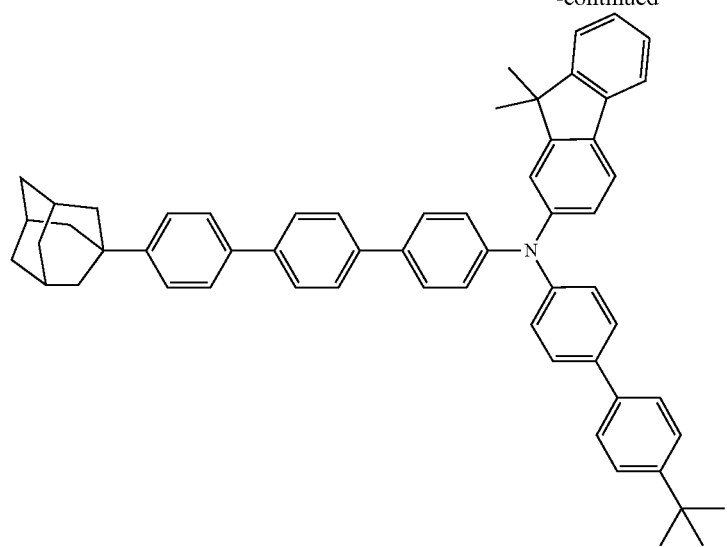
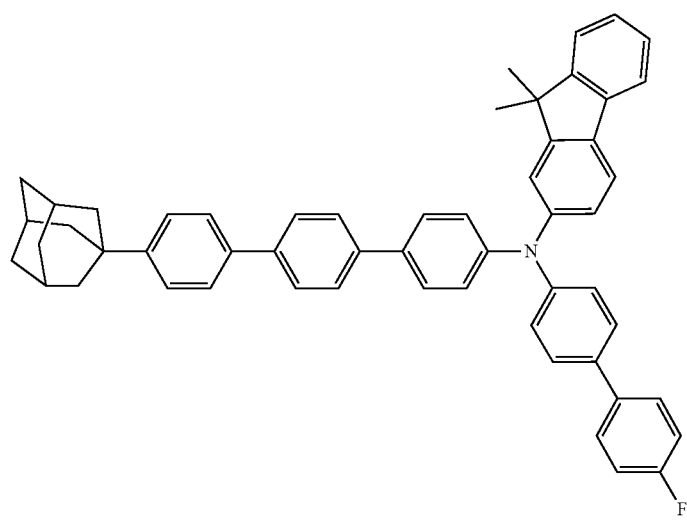
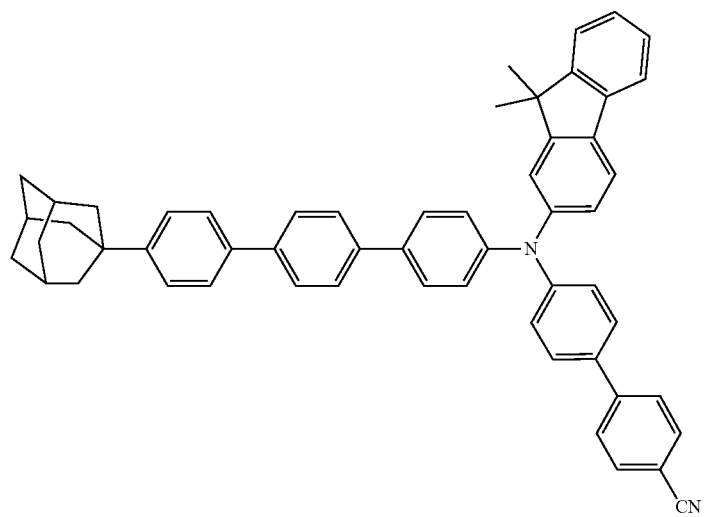

-continued
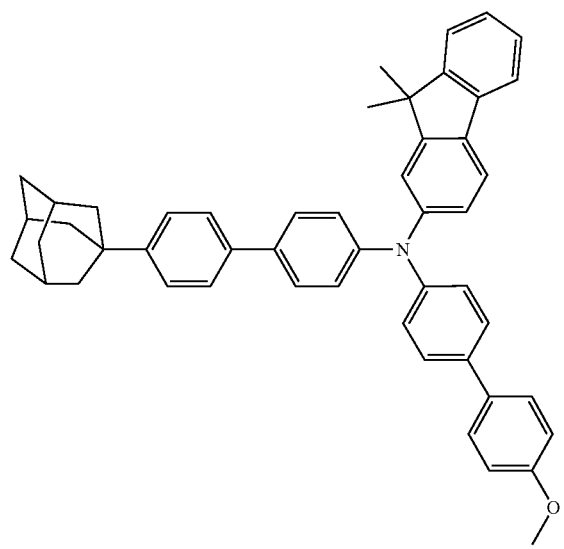
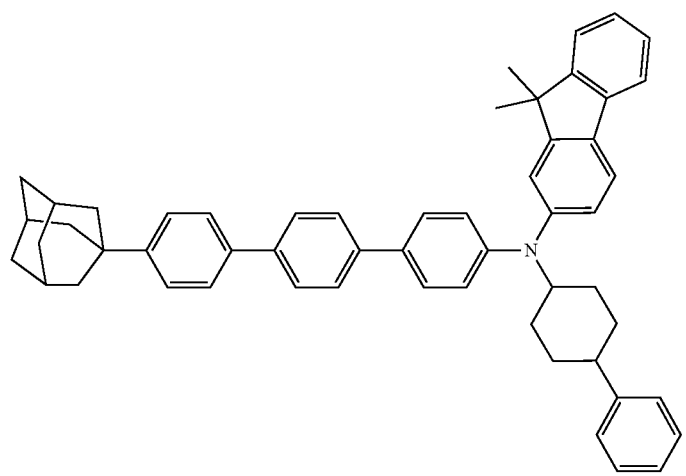
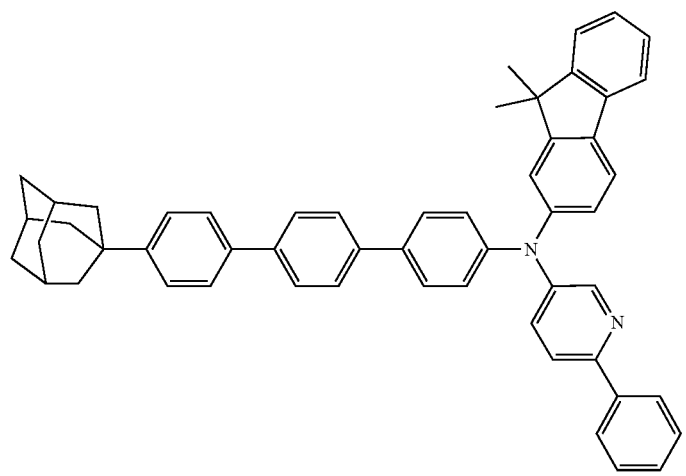

-continued
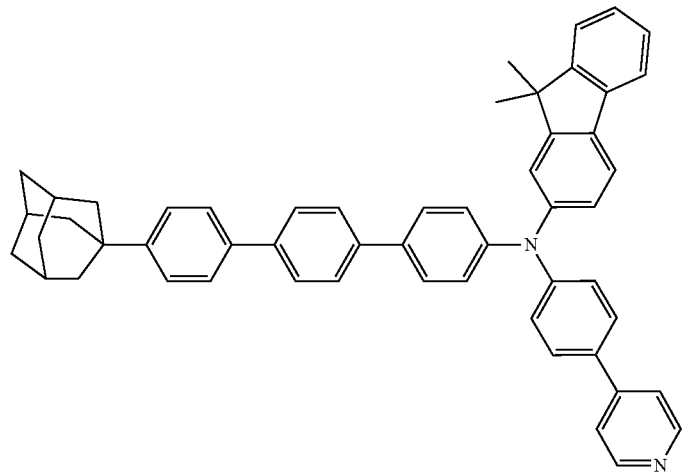
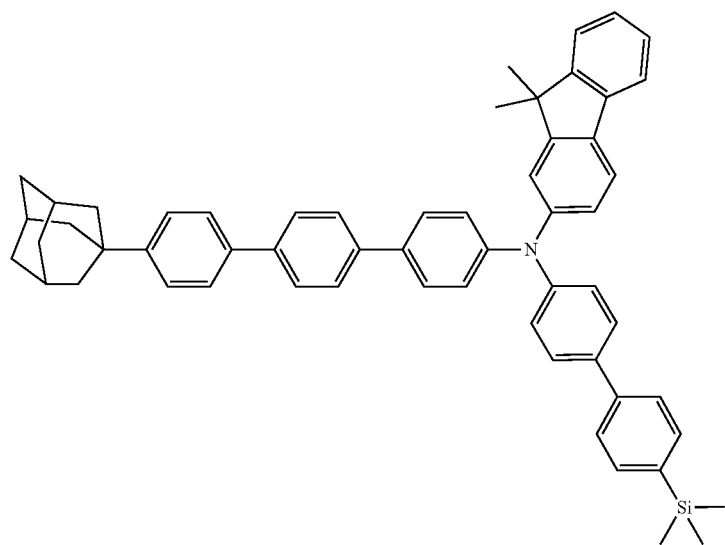
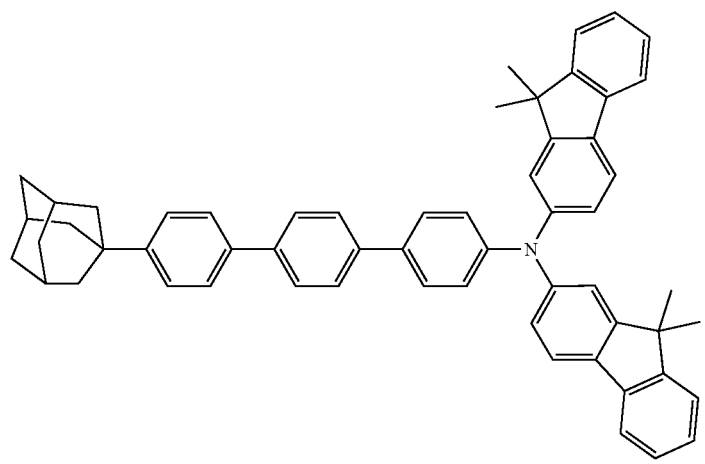
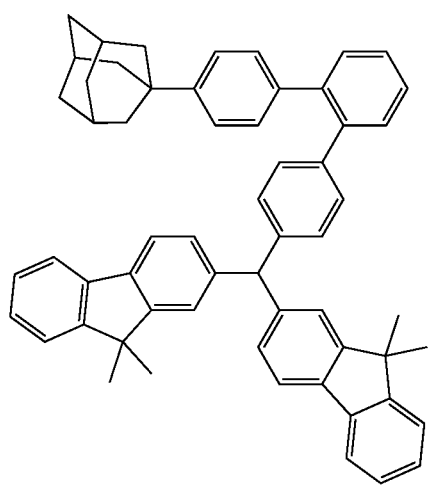

-continued
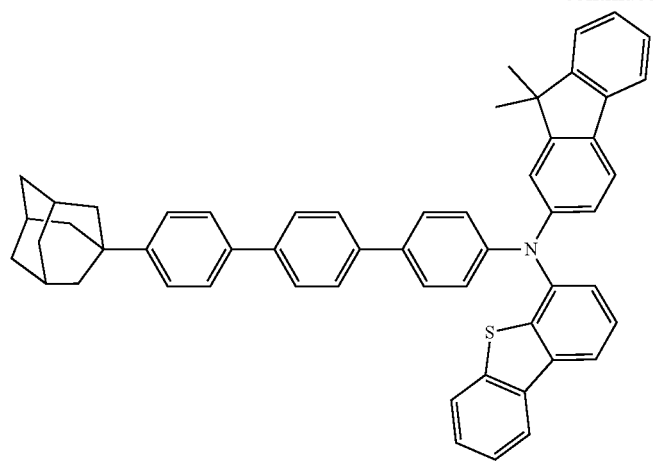
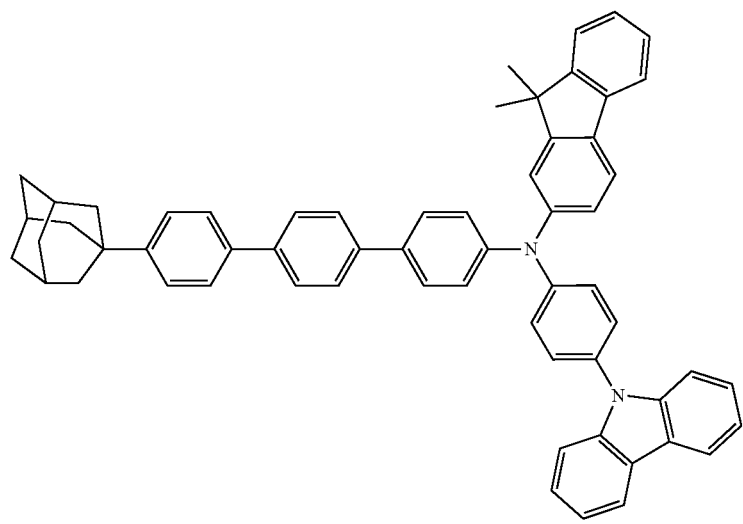
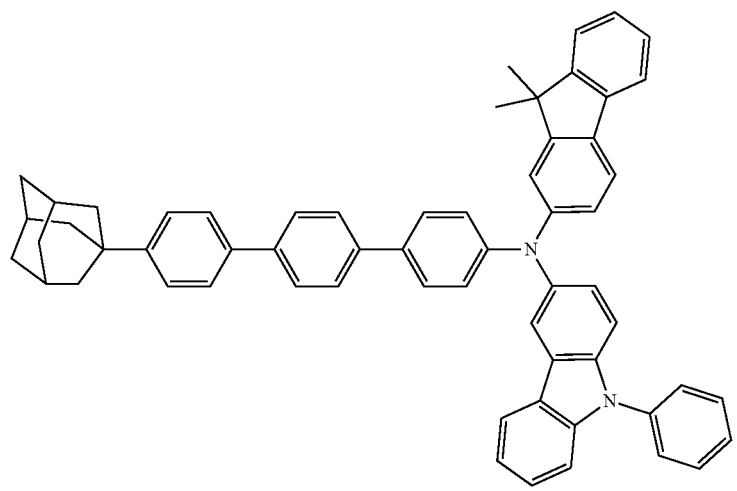

-continued
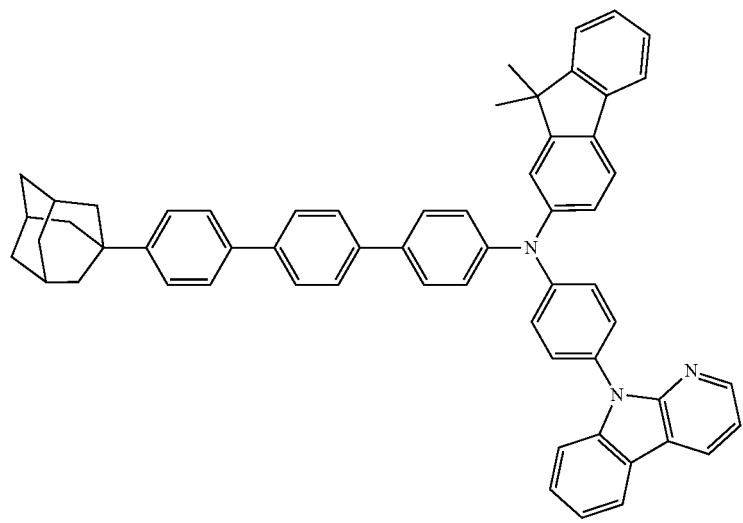
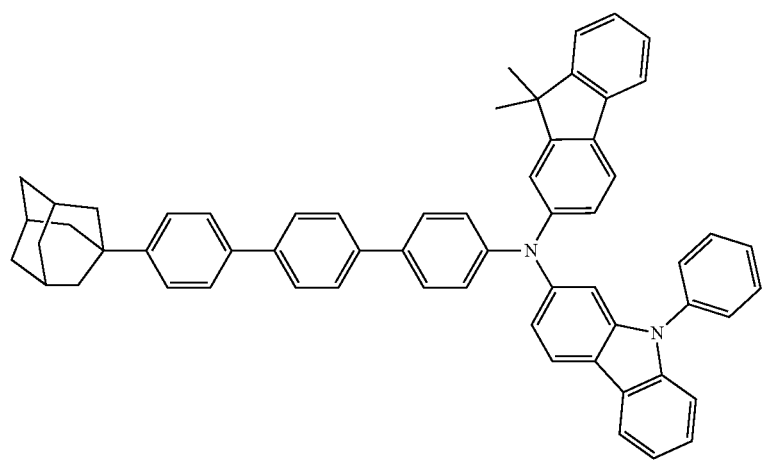
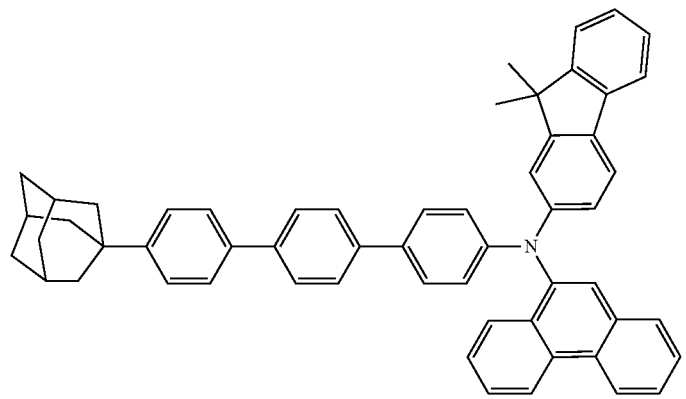

-continued
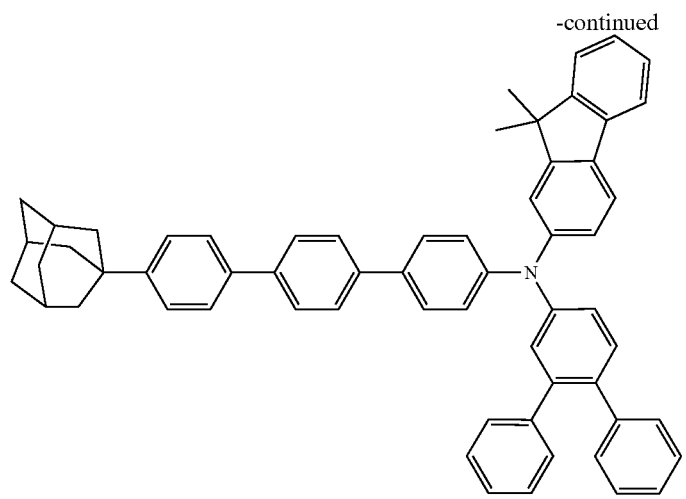
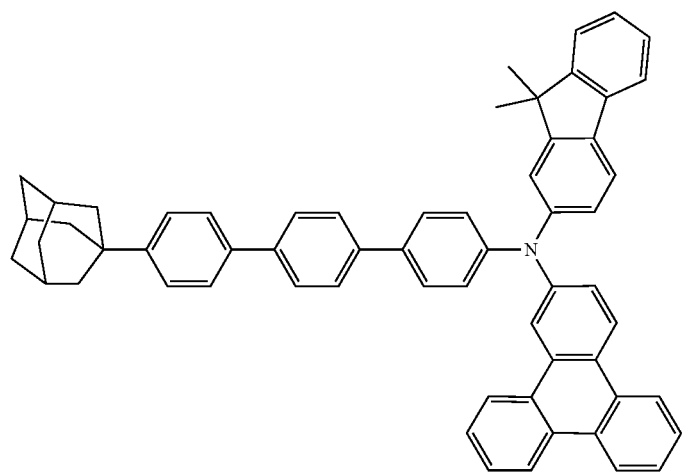
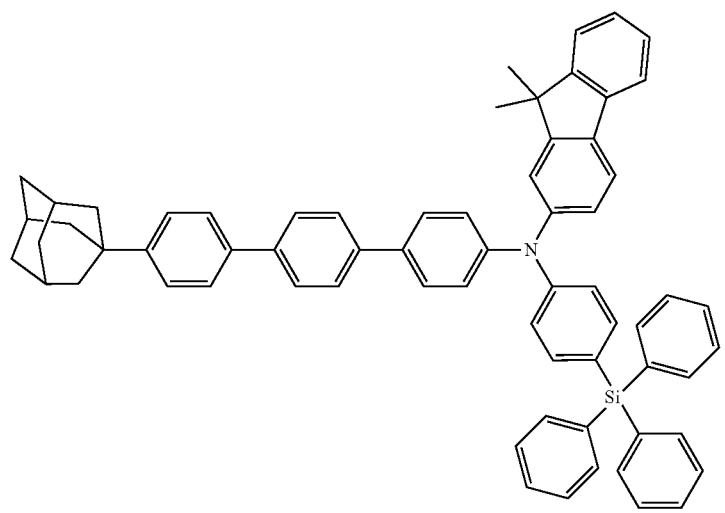

-continued
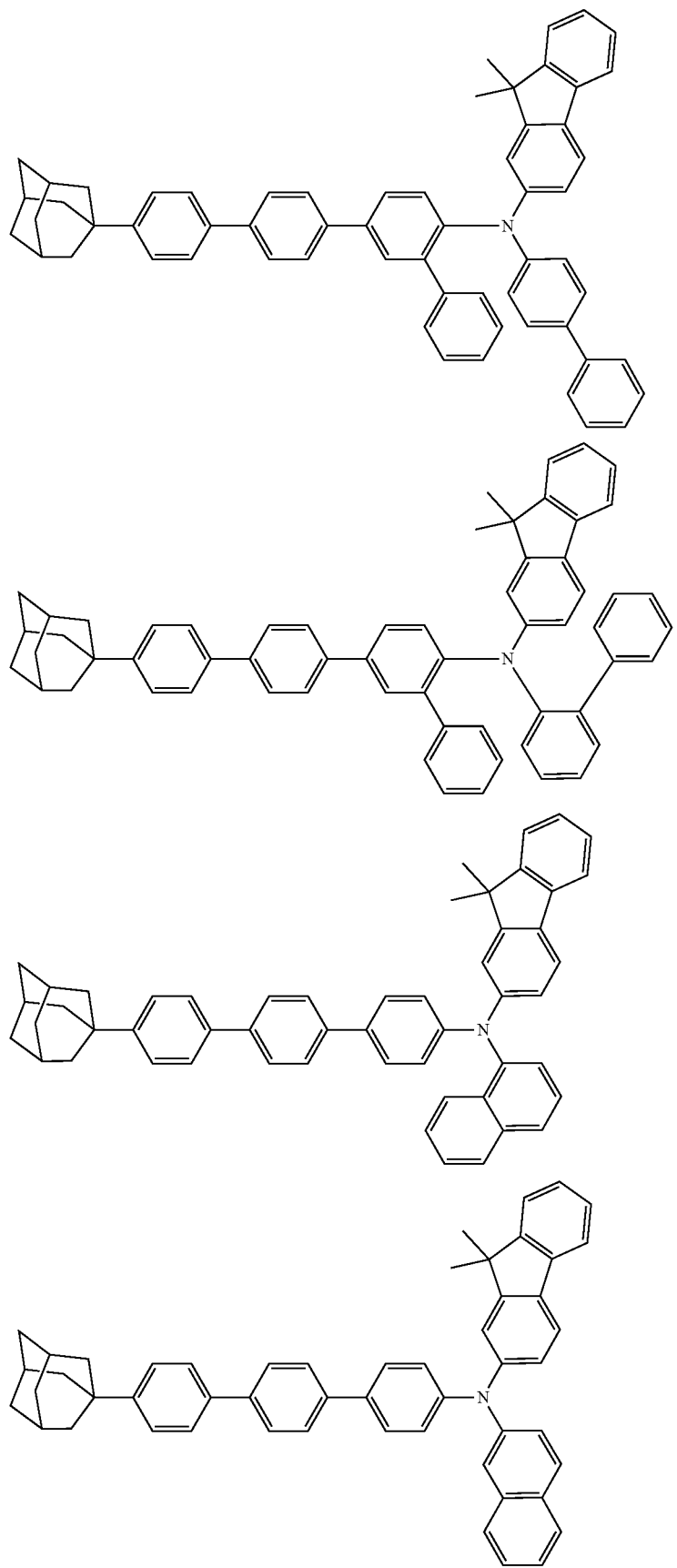

-continued
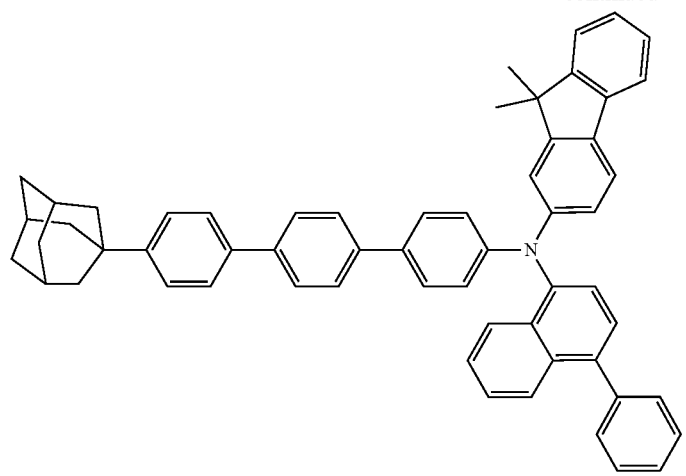
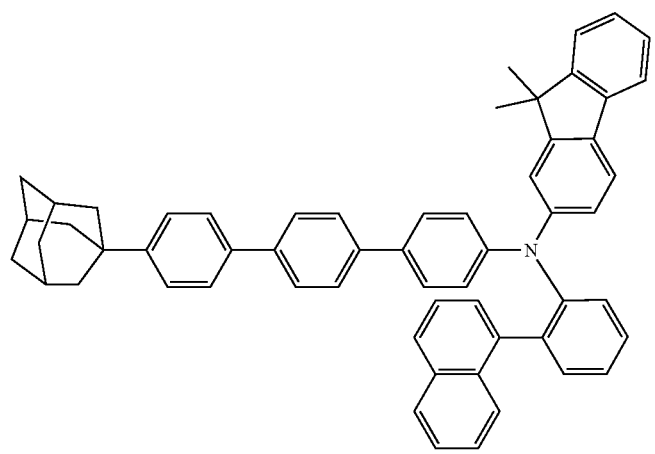
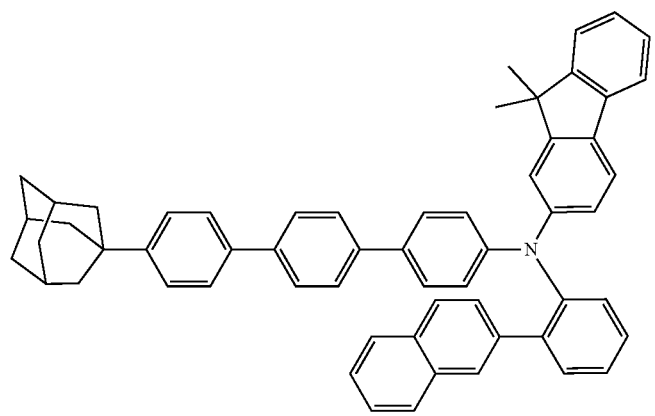

-continued
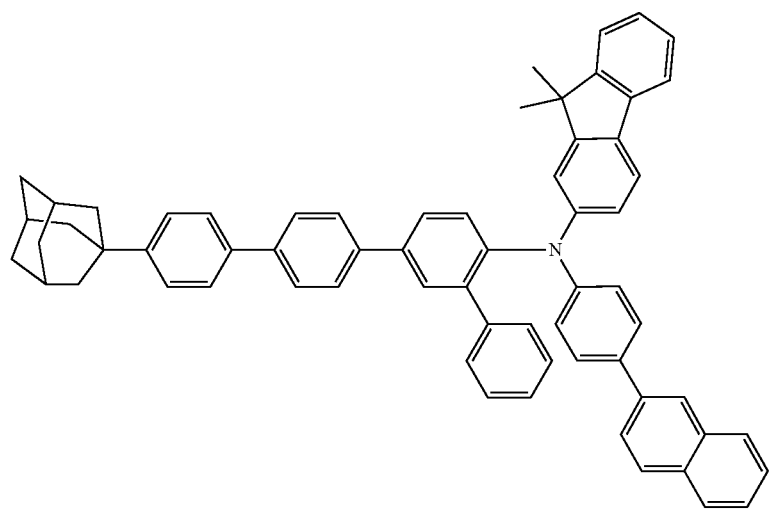
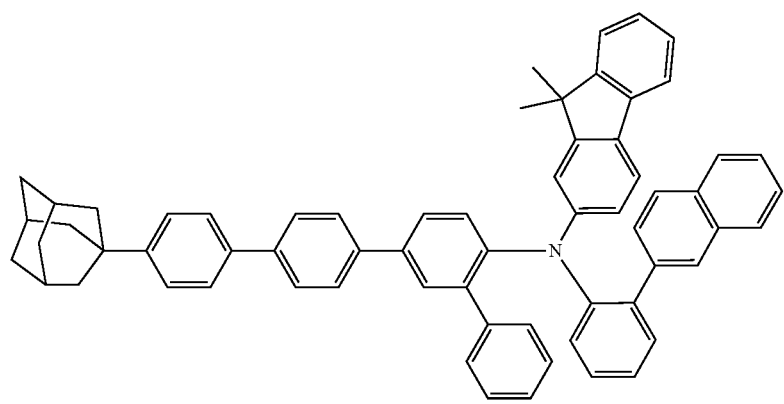
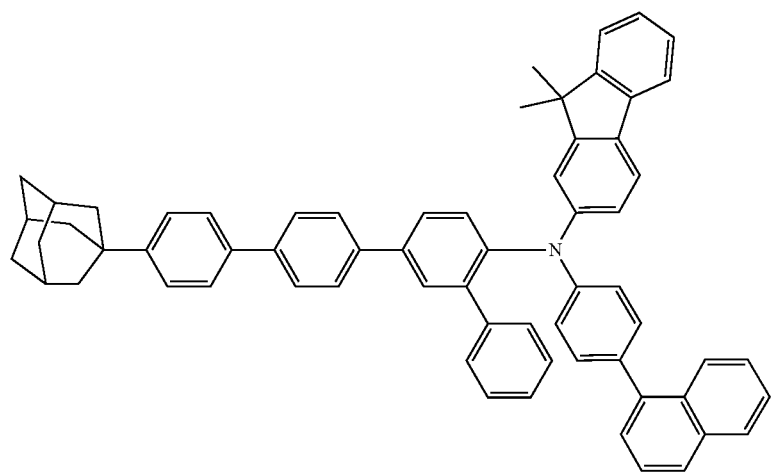

-continued
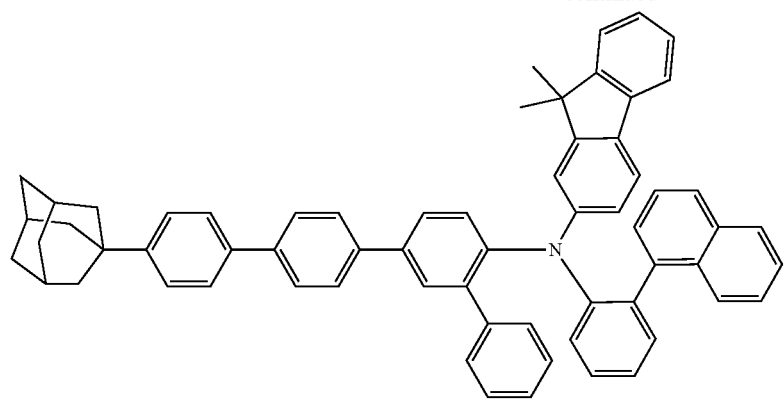
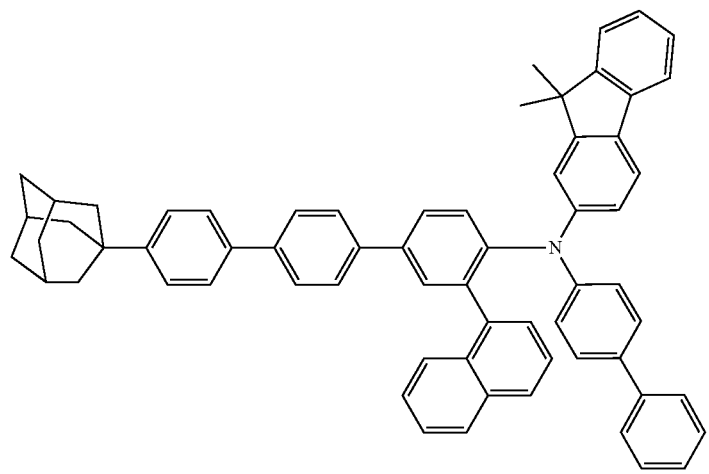
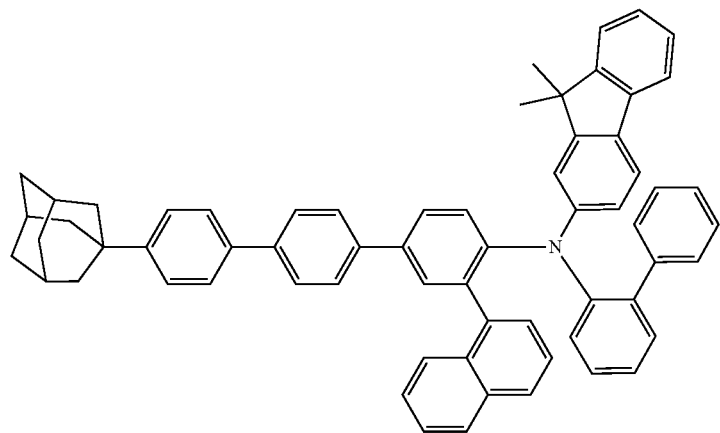

-continued
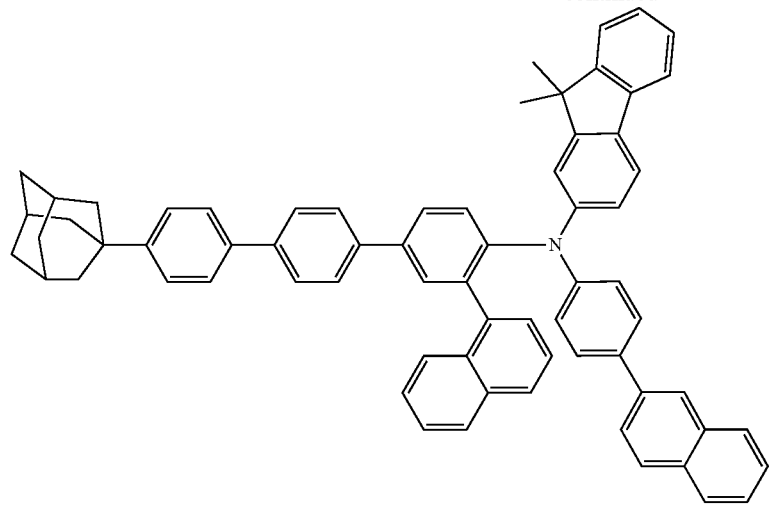
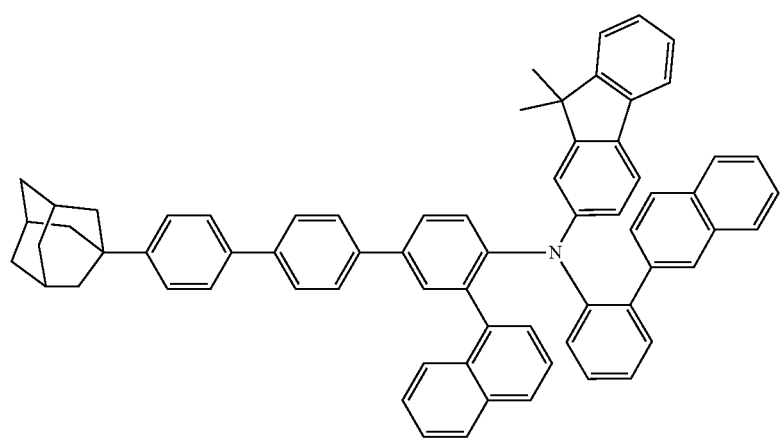
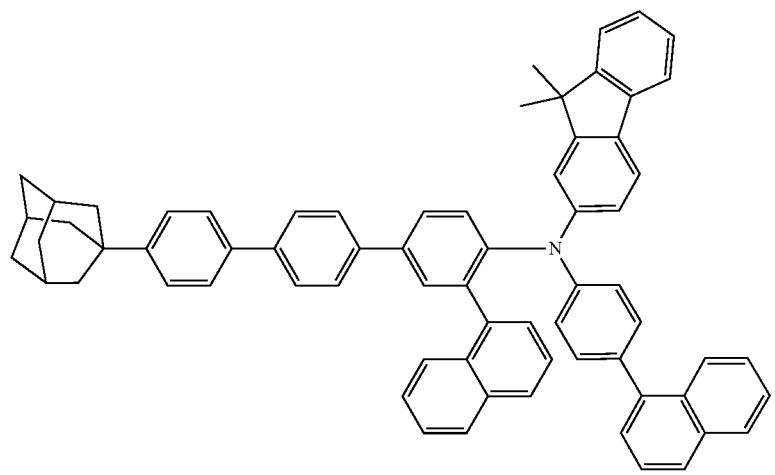

-continued
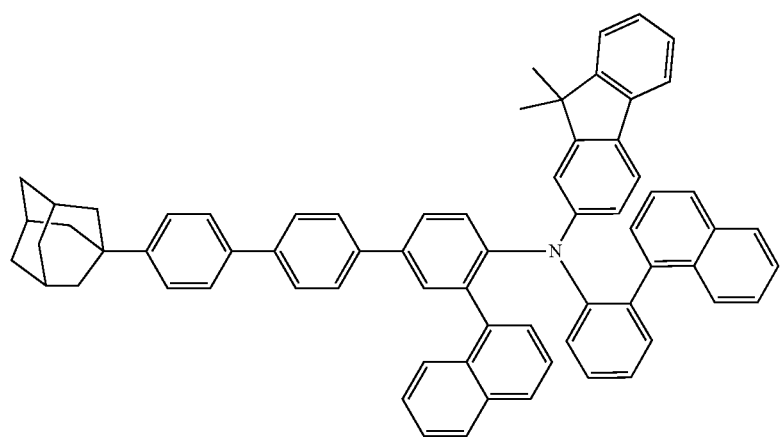
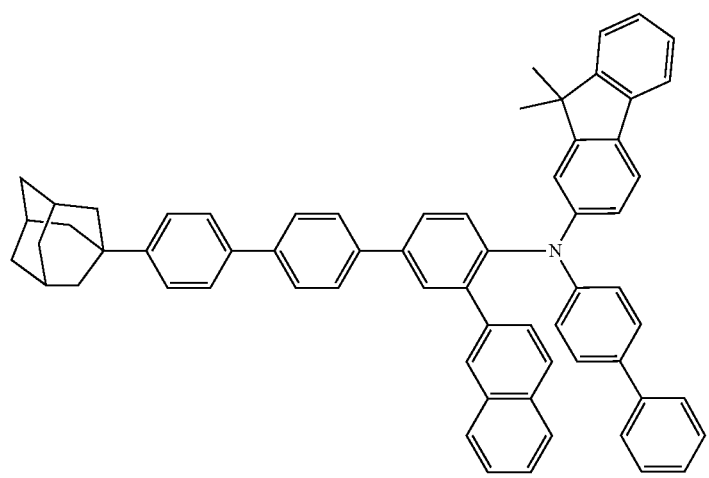
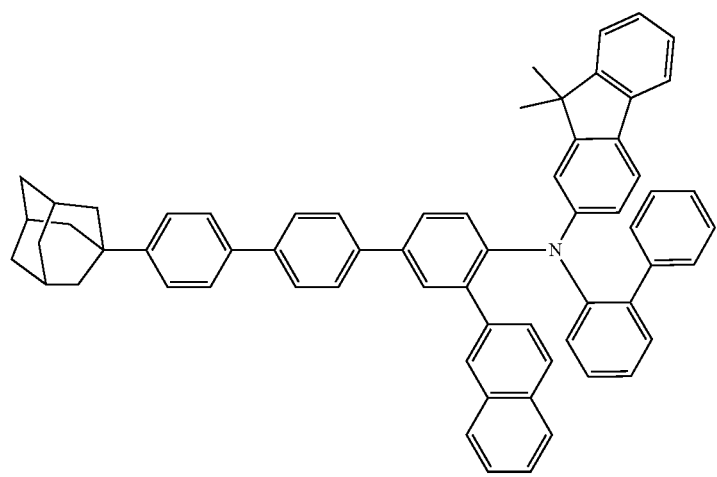

-continued
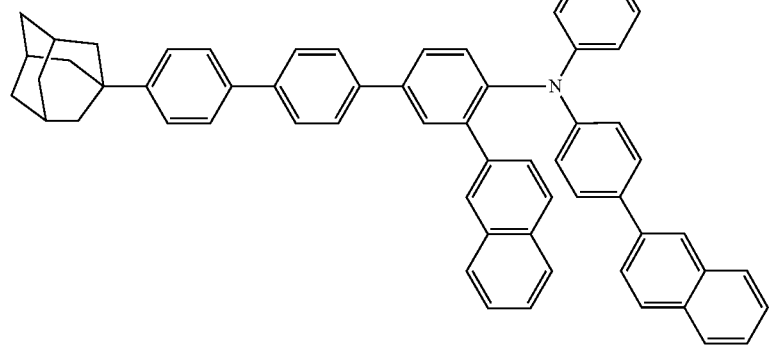
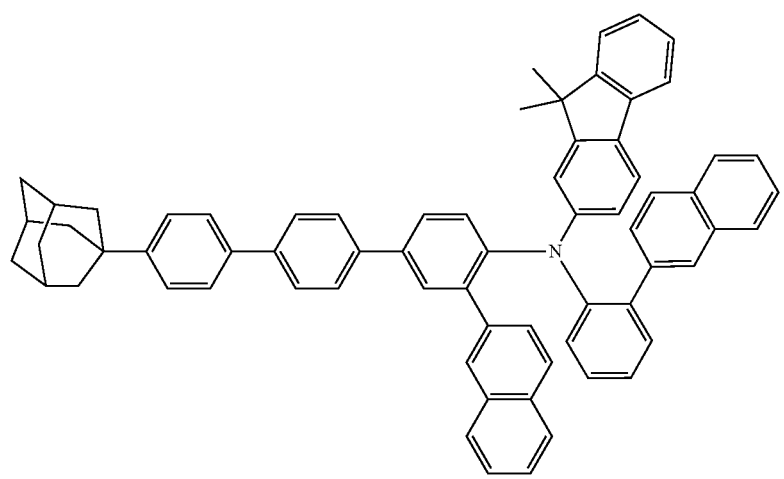
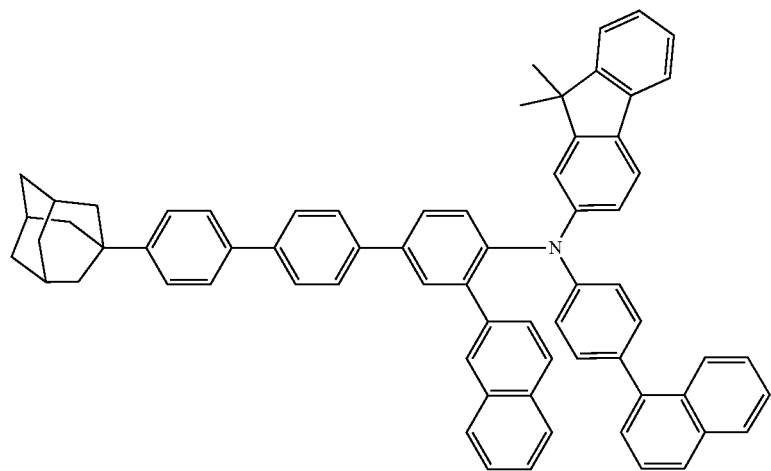

-continued
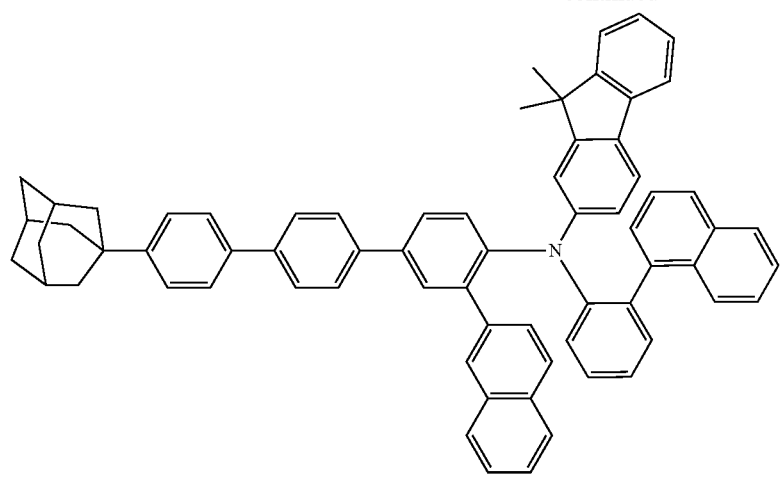
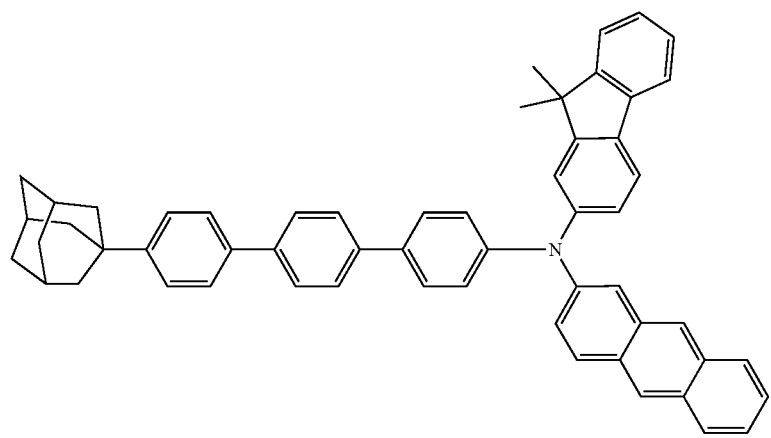
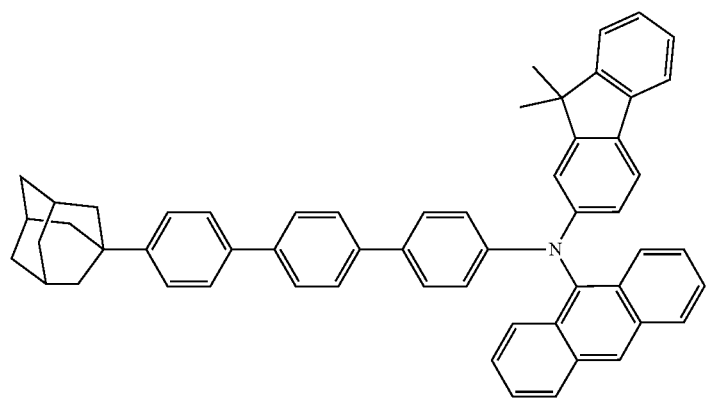

-continued
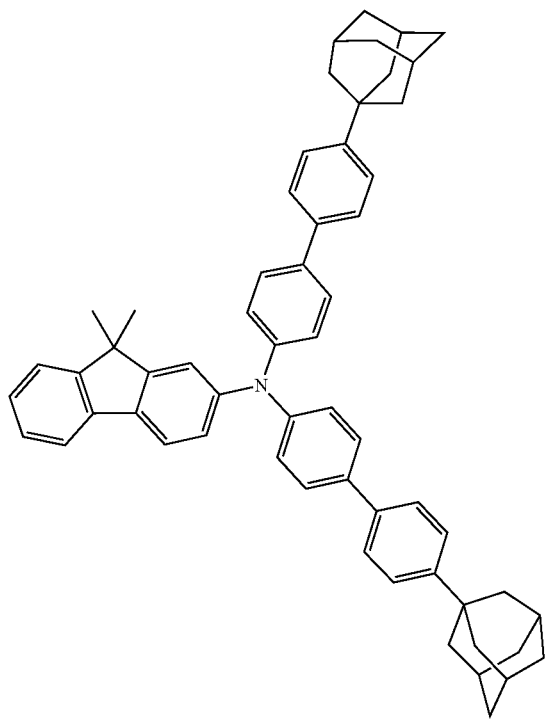
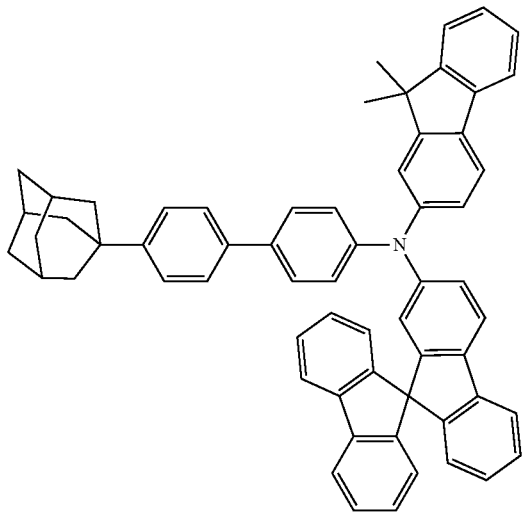
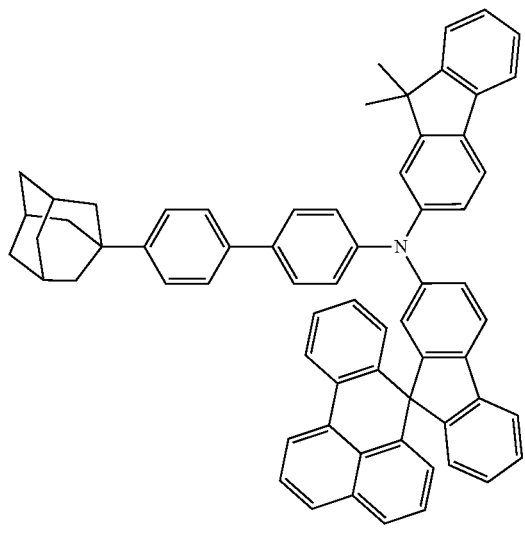
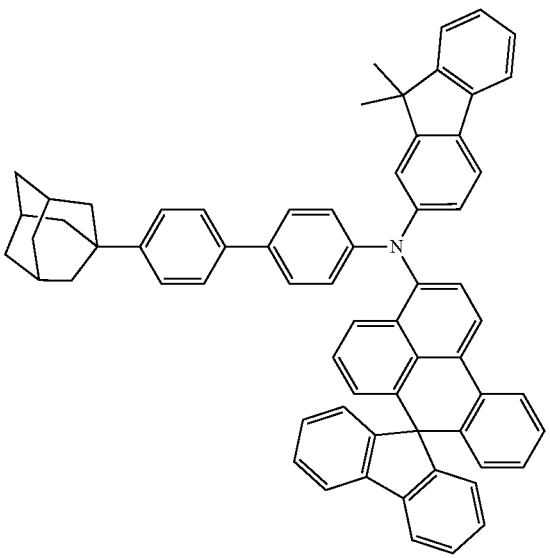

-continued
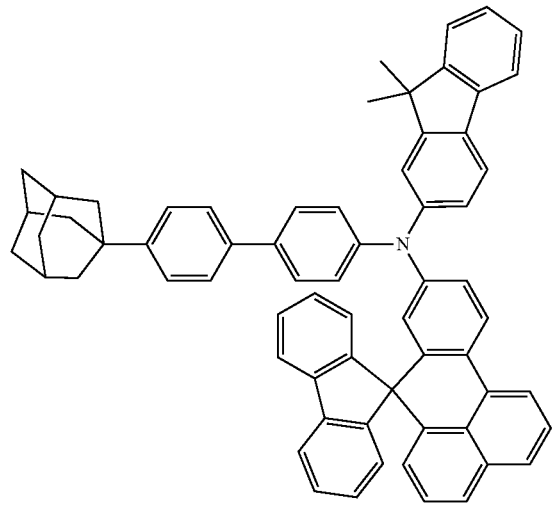
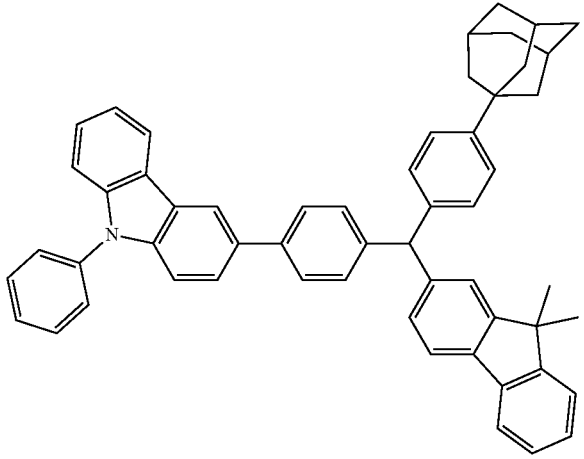
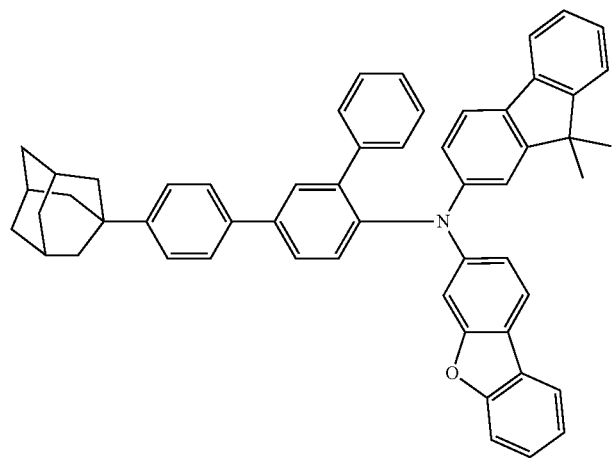
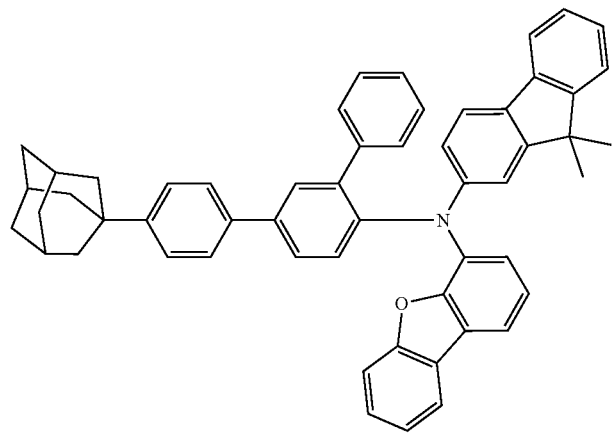

-continued

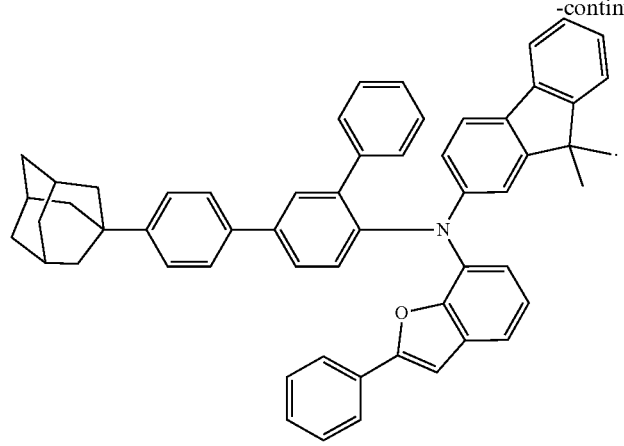

8. An organic light-emitting diode (OLED), comprising: a first electrode; and a second electrode placed opposite to the first electrode; and one or more organic material layers placed between the first electrode and the second electrode,
wherein at least one of the one or more organic material layers includes the compound of claim 1.

9. The OLED of claim 8, wherein the organic material layer is selected from the group consisting of a hole injection layer, a hole transfer layer, a light emitting layer, a hole blocking layer, an electron transport layer and an electron injection layer.

10. The OLED of claim 8, wherein the organic material layer is a light emitting layer.

11. The OLED of claim 8, wherein the organic material layer is a hole injection layer, a hole transfer layer or an electron blocking layer.

* * * * *